United States Patent
Gerber et al.

(10) Patent No.: US 12,186,590 B2
(45) Date of Patent: Jan. 7, 2025

(54) IMMUNE MODULATORS IN COMBINATION WITH RADIATION TREATMENT FOR ADVANCED PANCREATIC CANCER

(71) Applicant: UNIVERSITY OF ROCHESTER, Rochester, NY (US)

(72) Inventors: Scott Andrew Gerber, Penfield, NY (US); Dominick Auci, Buffalo, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 507 days.

(21) Appl. No.: 17/286,013

(22) PCT Filed: Oct. 18, 2019

(86) PCT No.: PCT/US2019/056927
§ 371 (c)(1),
(2) Date: Apr. 16, 2021

(87) PCT Pub. No.: WO2020/081929
PCT Pub. Date: Apr. 23, 2020

(65) Prior Publication Data
US 2021/0387020 A1   Dec. 16, 2021

Related U.S. Application Data

(60) Provisional application No. 62/747,830, filed on Oct. 19, 2018.

(51) Int. Cl.
*A61N 5/10* (2006.01)
*A61K 38/20* (2006.01)

(52) U.S. Cl.
CPC .......... *A61N 5/1048* (2013.01); *A61K 38/208* (2013.01); *A61N 2005/1098* (2013.01)

(58) Field of Classification Search
CPC ...... A61K 38/19; A61K 38/20; A61K 38/208; A61N 2005/1098; A61N 5/00; A61N 5/1048
See application file for complete search history.

(56) References Cited

U.S. PATENT DOCUMENTS

| | | | | |
|---|---|---|---|---|
| 6,051,428 A | * | 4/2000 | Fong | C12N 15/86 435/456 |
| 6,143,211 A | | 11/2000 | Mathiowitz | |

(Continued)

FOREIGN PATENT DOCUMENTS

| | | | | |
|---|---|---|---|---|
| CN | 105848649 A | * | 8/2016 | ......... A61K 31/4178 |
| JP | 2002518341 A | | 6/2002 | |

(Continued)

OTHER PUBLICATIONS

Brunda, M. J., Luistro, L., Warrier, R. R., Wright, R. B., Hubbard, B. R., Murphy, M., Wolf, S. F., & Gately, M. K. (1993). Antitumor and antimetastatic activity of interleukin 12 against murine tumors. Journal of Experimental Medicine, 178(4), 1223-1230. https://doi.org/10.1084/jem.178.4.1223 (Year: 1993).*

(Continued)

*Primary Examiner* — Christine H Matthews
*Assistant Examiner* — Marc D. Honrath
(74) *Attorney, Agent, or Firm* — Riverside Law LLP

(57) ABSTRACT

The invention provides methods of treating metastatic or unresectable pancreatic cancer through the administration of a combination of an immune modulator and radiation therapy.

12 Claims, 37 Drawing Sheets

(56) References Cited

U.S. PATENT DOCUMENTS

| | | | |
|---|---|---|---|
| 6,420,335 B1* | 7/2002 | Weichselbaum | A61K 38/363 514/19.2 |
| 2003/0166277 A1* | 9/2003 | Zauderer | A61P 15/18 530/391.1 |
| 2013/0243722 A1* | 9/2013 | Basile | A61K 38/208 424/85.2 |

FOREIGN PATENT DOCUMENTS

| | | |
|---|---|---|
| JP | 2007511507 A | 5/2007 |
| JP | 2017524743 A | 8/2017 |
| JP | 2018516256 A | 6/2018 |

OTHER PUBLICATIONS

Eglimez, N. K., Jong, Y. S., Sabel, M. S., Jacob, J. S., Mathiowitz, E., & Bankert, R. B. (2000). In Situ Tumor Vaccination with Interleukin-12-encapsulated Biodegradable Microspheres: Induction of Tumor Regression and Potent Antitumor Immunity. Cancer Research, (60), 3832-3837. PMI10919657 (Year: 2000).*

Coveler, A. L., Herman, J. M., Simeone, D. M., & Chiorean, E. G. (2016). Localized pancreatic cancer: Multidisciplinary management. American Society of Clinical Oncology Educational Book, (36), 217-236. https://doi.org/10.1200/edbk_160827 (Year: 2016).*

Kang, J., Demaria, S., & Formenti, S. (2016). Current clinical trials testing the combination of immunotherapy with radiotherapy. Journal for ImmunoTherapy of Cancer, 4(1). https://doi.org/10.1186/s40425-016-0156-7 (Year: 2016).*

Naghavi, A. O., Johnstone, P. A. S., & Kim, S. (2016). Clinical trials exploring the benefit of immunotherapy and radiation in cancer treatment: A review of the past and a look into the future. Current Problems in Cancer, 40(1), 38-67. https://doi.org/10.1016/j.currproblcancer.2015.10.002 (Year: 2016).*

Wu, C.-J., Tsai, Y.-T., Lee, I.-J., Wu, P.-Y., Lu, L.-S., Tsao, & Tao, M.-H. (2018). Combination of radiation and interleukin 12 eradicates large orthotopic hepatocellular carcinoma through immunomodulation of tumor microenvironment. Oncolmmunology, 7(9). https://doi.org/10.1080/2162402x.2018.1477459 (Year: 2018).*

Connolly, K. A. (2017). Targeting the radiotherapy-induced immune response leads to increased efficacy and survival in preclinical tumor models (thesis). (Year: 2017).*

Franziska Eckert, Ivan Jelas, Moritz Oehme, et al. (2017) Tumor-targeted IL-12 combined with local irradiation leads to systemic tumor control via abscopal effects in vivo, Oncolmmunology, 6:6, e1323161, DOI:10.1080/2162402X.2017.1323161 (Year: 2017).*

Kaur, P., & Asea, A. (2012). Radiation-induced effects and the immune system in cancer. Frontiers in Oncology, 2. https://doi.org/10.3389/fonc.2012.00191 (Year: 2012).*

Tozzi, A., Comito, T., & Alongi, F. (2013). SBRT in unresectable advanced pancreatic cancer: Preliminary results of a mono-institutional experience. Radiation Oncology, 8(1). https://doi.org/10.1186/1748-717x-8-148 (Year: 2013).*

Floros, T., & Tarhini, A. A. (2015). Anticancer cytokines: Biology and clinical effects of interferon-α2, interleukin (IL)-2, IL-15, IL-21, and il-12. Seminars in Oncology, 42(4), 539-548. https://doi.org/10.1053/j.seminoncol.2015.05.015 (Year: 2015).*

Crane, C. H. (2016). Hypofractionated ablative radiotherapy for locally advanced pancreatic cancer. Journal of Radiation Research, 57(S1), i53-i57. https://doi.org/10.1093/jrr/rrw016 (Year: 2016).*

Guo, N., Wang, W.-Q., & Gong, X.-J. (2017). Study of rhil-12 for treatment of complications after radiotherapy for tumor patients. World Journal of Clinical Oncology, 8(2), 158-167. https://doi.org/10.5306/wjco.v8.12.158 (Year: 2017).*

Wang, P., Li, X., & Wang, J. (2017). Re-designing interleukin-12 to enhance its safety and potential as an anti-tumor immunotherapeutic agent. Nature Communications, 8(1). https://doi.org/10.1038/s41467-017-01385-8 (Year: 2017).*

Al-Haddad M, Eloubeidi MA. Interventional EUS for the diagnosis and treatment of locally advanced pancreatic cancer. JOP. Jan. 8, 2010;11(1):1-7. PMID: 20065544.

Barberà-Cremades M, Baroja-Mazo A, Pelegrín P. Purinergic signaling during macrophage differentiation results in M2 alternative activated macrophages. J Leukoc Biol. Feb. 2016;99(2):289-99. doi: 10.1189/jlb.1A0514-267RR. Epub Sep. 17, 2015. PMID: 26382298.

Benci JL, Xu B, Qiu Y, Wu TJ, Dada H, Twyman-Saint Victor C, Cucolo L, Lee DSM, Pauken KE, Huang AC, Gangadhar TC, Amaravadi RK, Schuchter LM, Feldman MD, Ishwaran H, Vonderheide RH, Maity A, Wherry EJ, Minn AJ. Tumor Interferon Signaling Regulates a Multigenic Resistance Program to Immune Checkpoint Blockade. Cell. Dec. 1, 2016;167(6):1540-1554.e12. doi: 10.1016/j.cell.2016.11.022. PMID: 27912061; PMCID: PMC5385895.

Champion JA, Walker A, Mitragotri S. Role of particle size in phagocytosis of polymeric microspheres. Pharm Res. Aug. 2008;25(8):1815-21. doi: 10.1007/s11095-008-9562-y. Epub Mar. 2, 20089. PMID: 18373181; PMCID: PMC2793372.

Connolly KA, Belt BA, Figueroa NM, Murthy A, Patel A, Kim M, Lord EM, Linehan DC, Gerber SA. Increasing the efficacy of radiotherapy by modulating the CCR2/CCR5 chemokine axes. Oncotarget. Dec. 27, 2016;7(52):86522-86535. doi: 10.18632/oncotarget.13287. PMID: 27852031; PMCID: PMC5349932.

Feig C, Gopinathan A, Neesse A, Chan DS, Cook N, Tuveson DA. The pancreas cancer microenvironment. Clin Cancer Res. Aug. 15, 2012;18(16):4266-76. doi: 10.1158/1078-0432.CCR-11-3114. PMID: 22896693; PMCID: PMC3442232.

Freemerman AJ, Johnson AR, Sacks GN, Milner JJ, Kirk EL, Troester MA, Macintyre AN, Goraksha-Hicks P, Rathmell JC, Makowski L. Metabolic reprogramming of macrophages: glucose transporter 1 (GLUT1)-mediated glucose metabolism drives a proinflammatory phenotype. J Biol Chem. Mar. 14, 2014;289(11):7884-96. doi: 10.1074/jbc.M113.522037. Epub Feb. 3, 2014. PMID: 24492615; PMCID: PMC3953299.

Gillen S, Schuster T, Meyer Zum Büschenfelde C, Friess H, Kleeff J. Preoperative/neoadjuvant therapy in pancreatic cancer: a systematic review and meta-analysis of response and resection percentages. PLoS Med. Apr. 20, 2010;7(4):e1000267. doi: 10.1371/journal.pmed.1000267. PMID: 20422030; PMCID: PMC2857873.

Hammel P, Huguet F, van Laethem JL, Goldstein D, Glimelius B, Artru P, Borbath I, Bouché O, Shannon J, André T, Mineur L, Chibaudel B, Bonnetain F, Louvet C; LAP07 Trial Group. Effect of Chemoradiotherapy vs Chemotherapy on Survival in Patients With Locally Advanced Pancreatic Cancer Controlled After 4 Months of Gemcitabine With or Without Erlotinib: The LAP07 Randomized Clinical Trial. JAMA. May 3, 2016;315(17):1844-53. doi: 10.1001/jama.2016.4324. PMID: 27139057.

Hidalgo M, Cascinu S, Kleeff J, Labianca R, Löhr JM, Neoptolemos J, Real FX, Van Laethem JL, Heinemann V. Addressing the challenges of pancreatic cancer: future directions for improving outcomes. Pancreatology. Jan. 2015-Feb. 15(1):8-18. doi: 10.1016/j.pan.2014.10.001. Epub Oct. 17, 2014. PMID: 25547205.

Jenkins RW, Barbie DA, Flaherty KT. Mechanisms of resistance to immune checkpoint inhibitors. Br J Cancer. Jan. 2018;118(1):9-16. doi: 10.1038/bjc.2017.434. Epub Jan. 2, 2018. PMID: 29319049; PMCID: PMC5765236.

Jenks S. After initial setback, IL-12 regaining popularity. J Natl Cancer Inst. May 1, 1996;88(9):576-7. doi: 10.1093/jnci/88.9.576. PMID: 8609654.

Jones S, Zhang X, Parsons DW, Lin JC, Leary RJ, Angenendt P, Mankoo P, Carter H, Kamiyama H, Jimeno A, Hong SM, Fu B, Lin MT, Calhoun ES, Kamiyama M, Walter K, Nikolskaya T, Nikolsky Y, Hartigan J, Smith DR, Hidalgo M, Leach SD, Klein AP, Jaffee EM, Goggins M, Maitra A, Iacobuzio-Donahue C, Eshleman JR, Kern SE, Hruban RH, Karchin R, Papadopoulos N, Parmigiani G, Vogelstein B, Velculescu VE, Kinzler KW. Core signaling pathways in human pancreatic cancers revealed by global genomic analyses. Science. Sep. 26, 2008;321(5897):1801-6. doi.

Kalia V, Penny LA, Yuzefpolskiy Y, Baumann FM, Sarkar S. Quiescence of Memory CD8(+) T Cells Is Mediated by Regulatory T Cells through Inhibitory Receptor CTLA-4. Immunity. Jun. 16, 2015;42(6):1116-29. doi: 10.1016/j.immuni.2015.05.023. PMID: 26084026.

(56) References Cited

OTHER PUBLICATIONS

Kerkar SP, Goldszmid RS, Muranski P, Chinnasamy D, Yu Z, Reger RN, Leonardi AJ, Morgan RA, Wang E, Marincola FM, Trinchieri G, Rosenberg SA, Restifo NP. IL-12 triggers a programmatic change in dysfunctional myeloid-derived cells within mouse tumors. J Clin Invest. Dec. 2011;121(12):4746-57. doi: 10.1172/JCI58814. Epub Nov. 7, 2011. PMID: 22056381; PMCID: PMC3226001.

Lugade AA, Sorensen EW, Gerber SA, Moran JP, Frelinger JG, Lord EM. Radiation-induced IFN-gamma production within the tumor microenvironment influences antitumor immunity. J Immunol. Mar. 1, 2008;180(5):3132-9. doi: 10.4049/jimmunol.180.5.3132. PMID: 18292536.

MacMicking J, Xie QW, Nathan C. Nitric oxide and macrophage function. Annu Rev Immunol. 1997;15:323-50. doi: 10.1146/annurev. immunol.15.1.323. PMID: 9143691.

Mu X, Shi W, Xu Y, Xu C, Zhao T, Geng B, Yang J, Pan J, Hu S, Zhang C, Zhang J, Wang C, Shen J, Che Y, Liu Z, Lv Y, Wen H, You Q. Tumor-derived lactate induces M2 macrophage polarization via the activation of the ERK/STAT3 signaling pathway in breast cancer. Cell Cycle. 2018;17(4):428-438. doi: 10.1080/15384101. 2018.1444305. Epub Mar. 27, 2018. PMID: 29468929; PMCID: PMC5927648.

Neoptolemos JP, Stocken DD, Friess H, Bassi C, Dunn JA, Hickey H, Beger H, Fernandez-Cruz L, Dervenis C, Lacaine F, Falconi M, Pederzoli P, Pap A, Spooner D, Kerr DJ, Büchler MW; European Study Group for Pancreatic Cancer. A randomized trial of chemoradiotherapy and chemotherapy after resection of pancreatic cancer. N Engl J Med. Mar. 18, 2004;350(12):1200-10. doi: 10.1056/NEJMoa032295. Erratum in: N Engl J Med. Aug. 12, 2004;351(7):726. PMID: 15028824.

Norris PC, Dennis EA. A lipidomic perspective on inflammatory macrophage eicosanoid signaling. Adv Biol Regul. Jan. 2014;54:99-110. doi: 10.1016/j.jbior.2013.09.009. Epub Sep. 25, 2013. PMID: 24113376; PMCID: PMC3946543.

Oun R, Moussa YE, Wheate NJ. Correction: The side effects of platinum-based chemotherapy drugs: a review for chemists. Dalton Trans. Jun. 12, 2018;47(23):7848. doi: 10.1039/c8dt90088d. Erratum for: Dalton Trans. May 15, 2018;47(19):6645-6653. PMID: 29808879.

Oyler-Yaniv J, Oyler-Yaniv A, Shakiba M, Min NK, Chen YH, Cheng SY, Krichevsky O, Altan-Bonnet N, Altan-Bonnet G. Catch and Release of Cytokines Mediated by Tumor Phosphatidylserine Converts Transient Exposure into Long-Lived Inflammation. Mol Cell. Jun. 1, 2017;66(5):635-647.e7. doi: 10.1016/j.molcel.2017.05.011. PMID: 28575659; PMCID: PMC6611463.

Park SJ, Lee KP, Kang S, Lee J, Sato K, Chung HY, Okajima F, Im DS. Sphingosine 1-phosphate induced anti-atherogenic and atheroprotective M2 macrophage polarization through IL-4. Cell Signal. Oct. 2014;26(10):2249-58. doi: 10.1016/j.cellsig.2014.07.009. Epub Jul. 14, 2014. PMID: 25035231.

Pfirschke C, Engblom C, Rickelt S, Cortez-Retamozo V, Garris C, Pucci F, Yamazaki T, Poirier-Colame V, Newton A, Redouane Y, Lin YJ, Wojtkiewicz G, Iwamoto Y, Mino-Kenudson M, Huynh TG, Hynes RO, Freeman GJ, Kroemer G, Zitvogel L, Weissleder R, Pittet MJ. Immunogenic Chemotherapy Sensitizes Tumors to Checkpoint Blockade Therapy. Immunity. Feb. 16, 2016;44(2):343-54. doi: 10.1016/j.immuni.2015.11.024. Epub Feb. 9, 2016. PMID: 26872698; PMCID: PMC4758865.

Quéméneur L, Beloeil L, Michallet MC, Angelov G, Tomkowiak M, Revillard JP, Marvel J. Restriction of de novo nucleotide biosynthesis interferes with clonal expansion and differentiation into effector and memory CD8 T cells. J Immunol. Oct. 15, 2004;173(8):4945-52. doi: 10.4049/jimmunol.173.8.4945. PMID: 15470036.

Rech AJ, Dada H, Kotzin JJ, Henao-Mejia J, Minn AJ, Twyman-Saint Victor C, Vonderheide RH. Radiotherapy and CD40 Activation Separately Augment Immunity to Checkpoint Blockade in Cancer. Cancer Res. Aug. 1, 2018;78(15):4282-4291. doi: 10.1158/0008-5472.CAN-17-3821. Epub May 29, 2018. PMID: 29844122; PMCID: PMC6415684.

Rich T, Harris J, Abrams R, Erickson B, Doherty M, Paradelo J, Small W Jr, Safran H, Wanebo HJ. Phase II study of external irradiation and weekly paclitaxel for nonmetastatic, unresectable pancreatic cancer: RTOG-98-12. Am J Clin Oncol. Feb. 2004;27(1):51-6. doi: 10.1097/01.coc.0000046300.88847.bf. PMID: 14758134.

Schrek R. Qualitative and quantitative reactions of lymphocytes to x rays. Ann N Y Acad Sci. Nov. 13, 1961;95:839-48. doi: 10.1111/j.1749-6632.1961.tb50080.x. PMID: 13909294.

Sevenich L, Joyce JA. Pericellular proteolysis in cancer. Genes Dev. Nov. 1, 2014;28(21):2331-47. doi: 10.1101/gad.250647.114. PMID: 25367033; PMCID: PMC4215179.

Strasly M, Cavallo F, Geuna M, Mitola S, Colombo MP, Forni G, Bussolino F. IL-12 inhibition of endothelial cell functions and angiogenesis depends on lymphocyte-endothelial cell cross-talk. J Immunol. Mar. 15, 2001;166(6):3890-9. doi: 10.4049/jimmunol. 166.6.3890. PMID: 11238633.

Suzuki S, Umezu Y, Saijo Y, Satoh G, Abe Y, Satoh K, Nukiwa T. Exogenous recombinant human IL-12 augments MHC class I antigen expression on human cancer cells in vitro. Tohoku J Exp Med. Jul. 1998;185(3):223-6. doi: 10.1620/tjem.185.223. PMID: 9823783.

Thind K, Padrnos LJ, Ramanathan RK, Borad MJ. Immunotherapy in pancreatic cancer treatment: a new frontier. Therap Adv Gastroenterol. Jan. 2017;10(1):168-194. doi: 10.1177/1756283X16667909. Epub Oct. 17, 2016. PMID: 28286568; PMCID: PMC5330603.

Timmerman RD, Herman J, Cho LC. Emergence of stereotactic body radiation therapy and its impact on current and future clinical practice. J Clin Oncol. Sep. 10, 2014;32(26):2847-54. doi: 10.1200/JCO.2014.55.4675. Epub Aug. 11, 2014. PMID: 25113761; PMCID: PMC4152712.

Trinchieri G, Wysocka M, D'Andrea A, Rengaraju M, Aste-Amezaga M, Kubin M, Valiante NM, Chehimi J. Natural killer cell stimulatory factor (NKSF) or interleukin-12 is a key regulator of immune response and inflammation. Prog Growth Factor Res. 1992;4(4):355-68. doi: 10.1016/0955-2235(92)90016-b. PMID: 1364096.

Vonderheide RH. The Immune Revolution: A Case for Priming, Not Checkpoint. Cancer Cell. Apr. 9, 2018;33(4):563-569. doi: 10.1016/j.ccell.2018.03.008. PMID: 29634944; PMCID: PMC5898647.

Walle T, Martinez Monge R, Cerwenka A, Ajona D, Melero I, Lecanda F. Radiation effects on antitumor immune responses: current perspectives and challenges. Ther Adv Med Oncol. Jan. 18, 2018;10:1758834017742575. doi: 10.1177/1758834017742575. PMID: 29383033; PMCID: PMC5784573.

Wang, B., Li, Q., Qin, L et al. Transition of tumor-associated macrophages from MHC class IIhi to MHC class IIlow mediates tumor progression in mice. BMC Immunol 12, 43 (2011). https://doi.org/10.1186/1471-2172-12-43.

Wei H, Tarling EJ, McMillen TS, Tang C, LeBoeuf RC. ABCG1 regulates mouse adipose tissue macrophage cholesterol levels and ratio of M1 to M2 cells in obesity and caloric restriction. J Lipid Res. Dec. 2015;56(12):2337-47. doi: 10.1194/jlr.M063354. Epub Oct. 21, 2015. PMID: 26489644; PMCID: PMC4655989.

White MJ, Gomer RH. Trypsin, Tryptase, and Thrombin Polarize Macrophages towards a Pro-Fibrotic M2a Phenotype. PLoS One. Sep. 25, 2015;10(9):e0138748. doi: 10.1371/journal.pone.0138748. PMID: 26407067; PMCID: PMC4583378.

Xu J, Escamilla J, Mok S, David J, Priceman S, West B, Bollag G, McBride W, Wu L. CSF1R signaling blockade stanches tumor-infiltrating myeloid cells and improves the efficacy of radiotherapy in prostate cancer. Cancer Res. May 1, 2013;73(9):2782-94. doi: 10.1158/0008-5472.CAN-12-3981. Epub Feb. 15, 2013. PMID: 23418320; PMCID: PMC4097014.

Yasmin-Karim S, Bruck PT, Moreau M, Kunjachan S, Chen GZ, Kumar R, Grabow S, Dougan SK, Ngwa W. Radiation and Local Anti-CD40 Generate an Effective in situ Vaccine in Preclinical Models of Pancreatic Cancer. Front Immunol. Sep. 7, 2018;9:2030. doi: 10.3389/fimmu.2018.02030. PMID: 30245691; PMCID: PMC6137176.

Zeh HJ 3rd, Hurd S, Storkus WJ, Lotze MT. Interleukin-12 promotes the proliferation and cytolytic maturation of immune effectors: implications for the immunotherapy of cancer. J Immunother

(56) References Cited

OTHER PUBLICATIONS

Emphasis Tumor Immunol. Aug. 1993;14(2):155-61. doi: 10.1097/00002371-199308000-00012. PMID: 7904180.

Zhong J, Patel K, Switchenko J, Cassidy RJ, Hall WA, Gillespie T, Patel PR, Kooby D, Landry J. Outcomes for patients with locally advanced pancreatic adenocarcinoma treated with stereotactic body radiation therapy versus conventionally fractionated radiation. Cancer. Sep. 15, 2017;123(18):3486-3493. doi: 10.1002/cncr.30706. Epub May 10, 2017. PMID: 28493288; PMCID: PMC5589506.

Zhou L, Chong MM, Littman DR. Plasticity of CD4+ T cell lineage differentiation. Immunity. May 2009;30(5):646-55. doi: 10.1016/j.immuni.2009.05.001. PMID: 19464987.

Zhu Y, Herndon JM, Sojka DK, Kim KW, Knolhoff BL, Zuo C, Cullinan DR, Luo J, Bearden AR, Lavine KJ, Yokoyama WM, Hawkins WG, Fields RC, Randolph GJ, DeNardo DG. Tissue-Resident Macrophages in Pancreatic Ductal Adenocarcinoma Originate from Embryonic Hematopoiesis and Promote Tumor Progression. Immunity. Aug. 15, 2017;47(2):323-338.e6. doi: 10.1016/j.immuni.2017.07.014. Erratum in: Immunity. Sep. 19, 2017;47(3):597. PMID: 28813661; PMCID: PMC5578409.

* cited by examiner

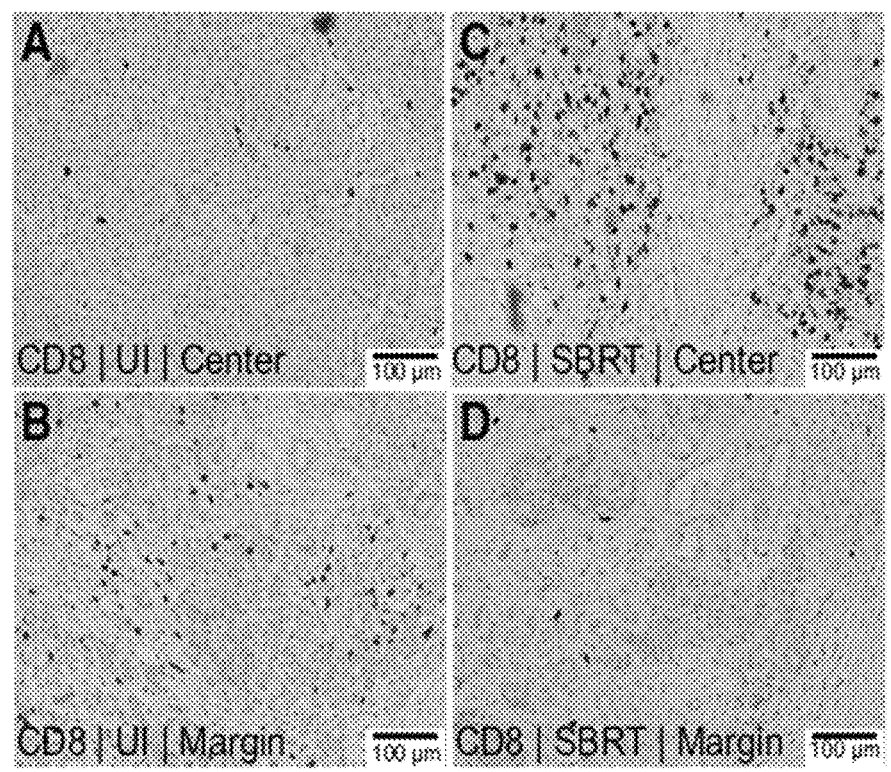
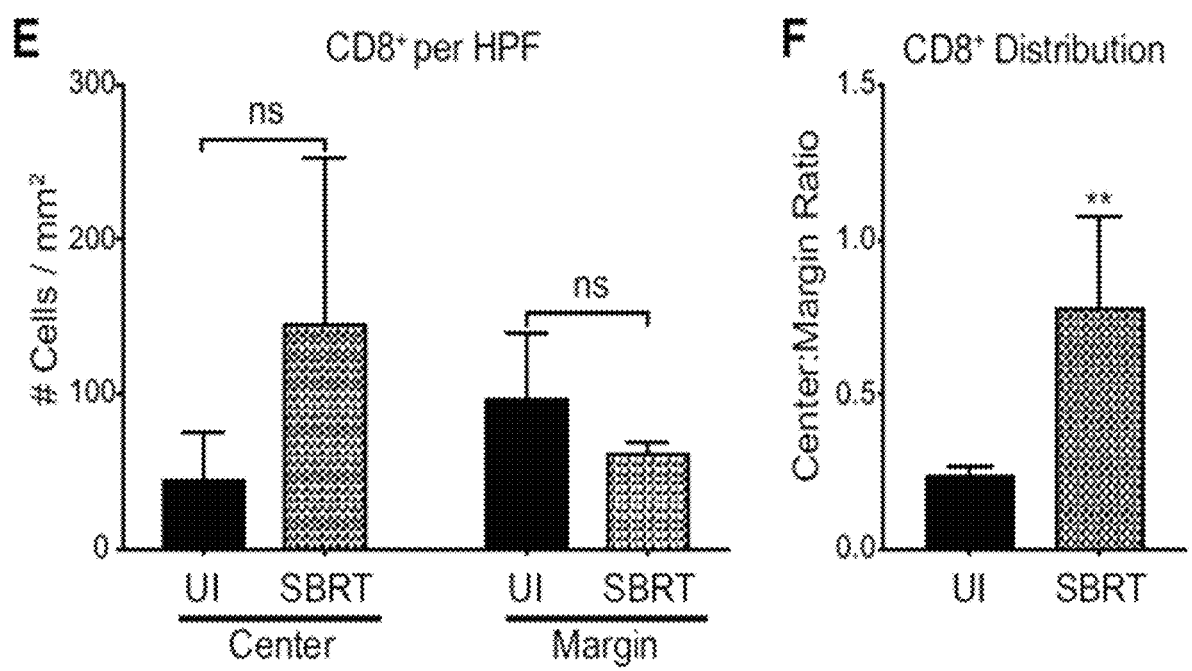
Fig. 1A – 1F

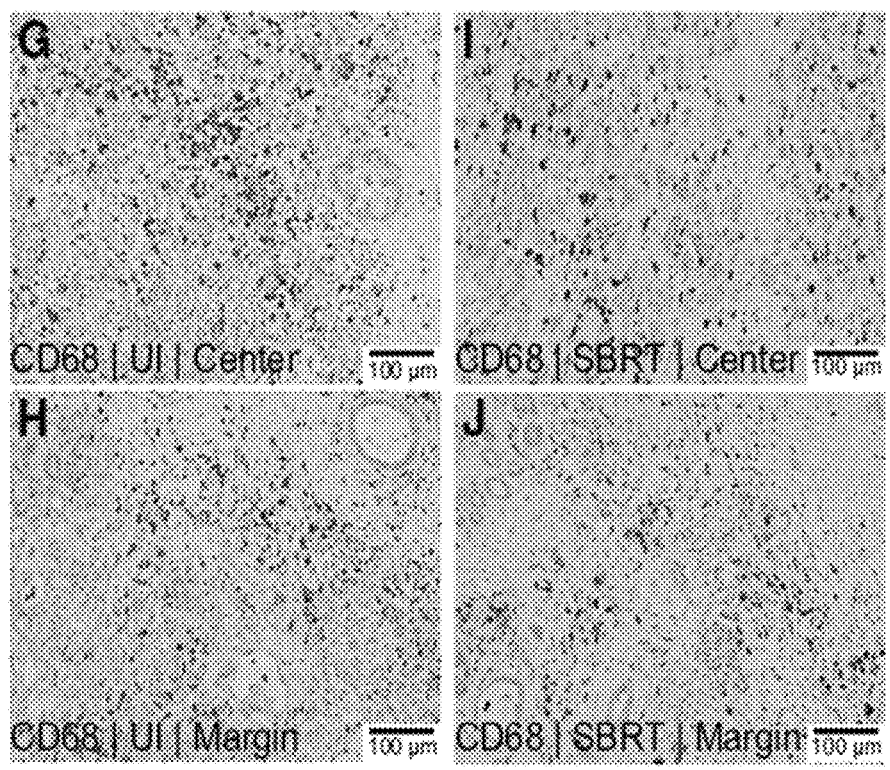
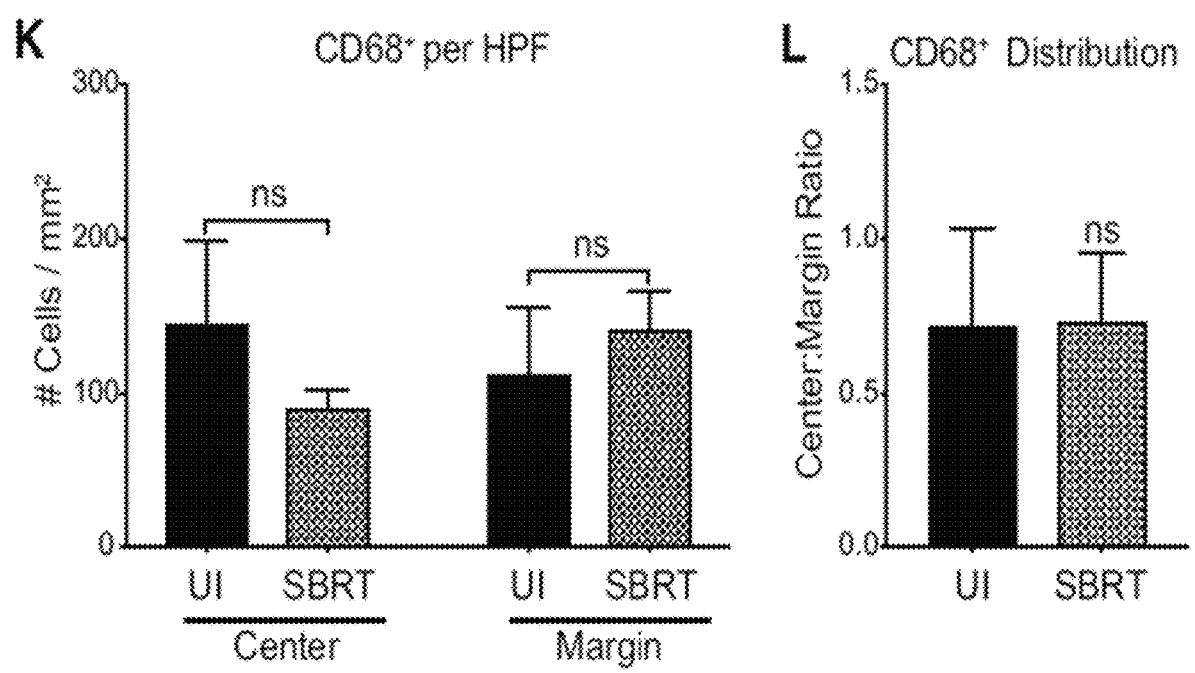
Fig. 1G – 1L

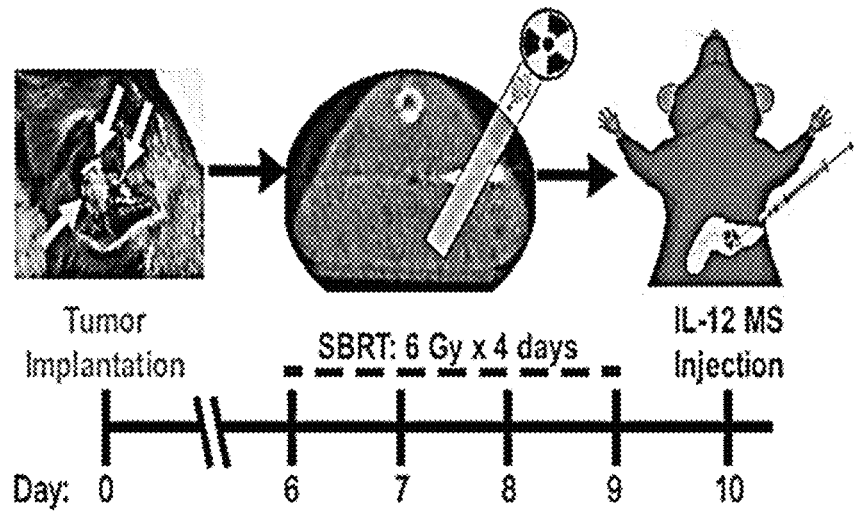
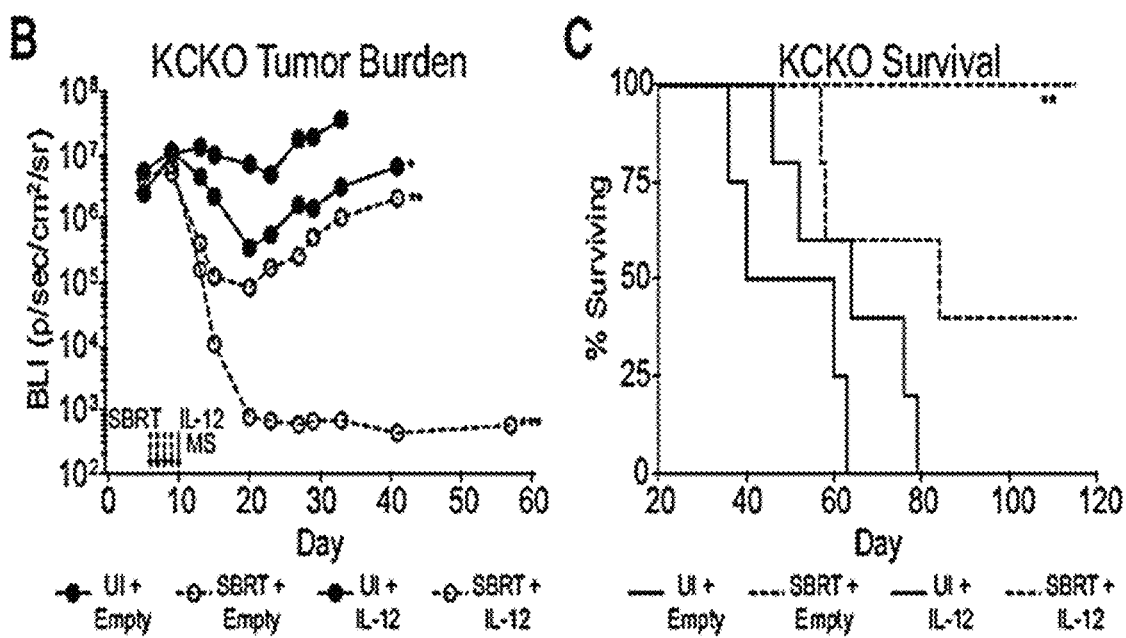
Fig. 2A -2C

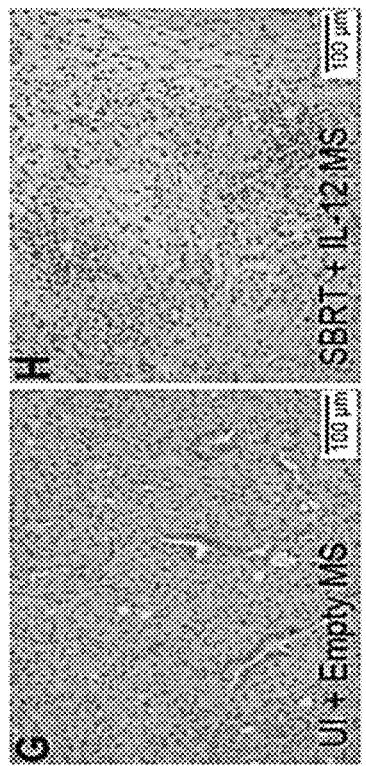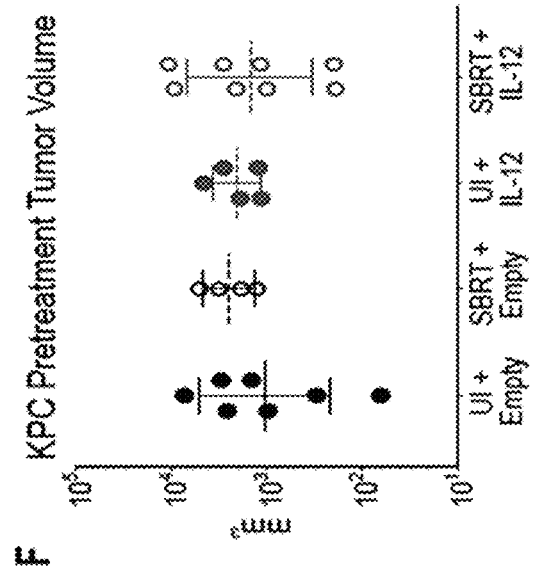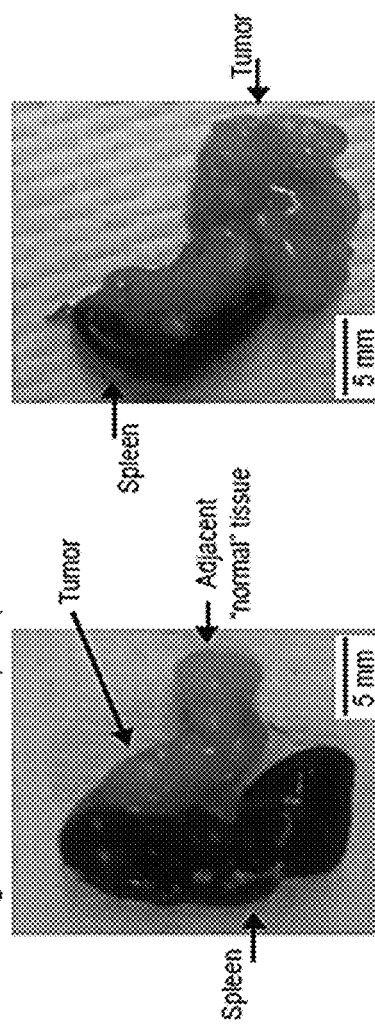
Fig. 4F – 4I

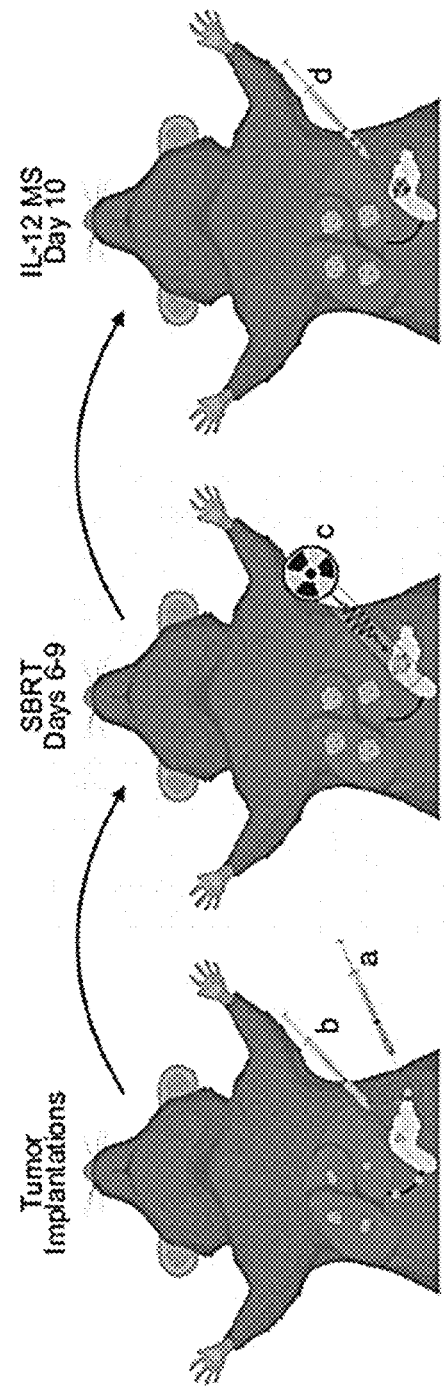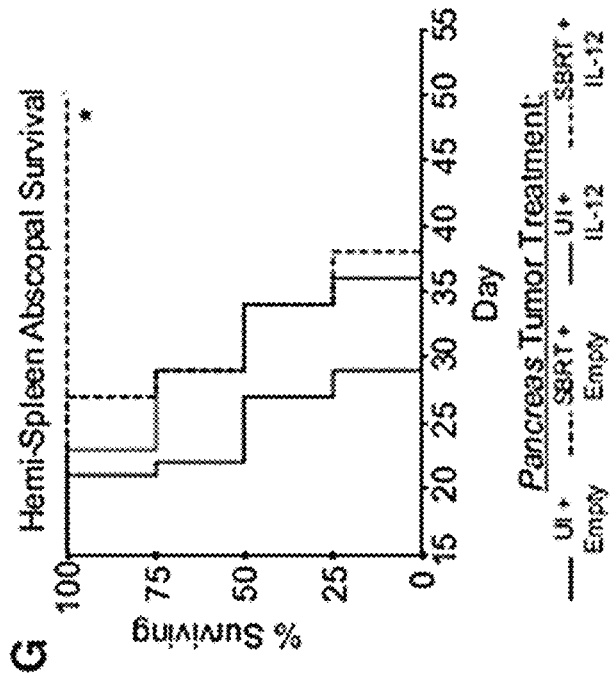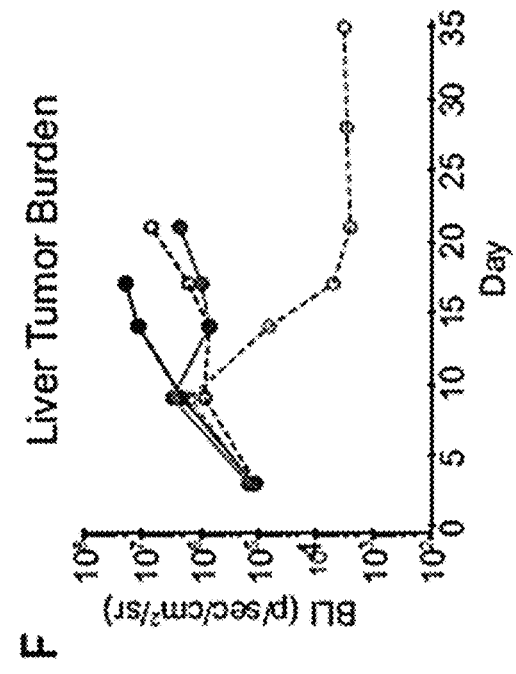
Fig. 13E – 13G

IMMUNE MODULATORS IN COMBINATION WITH RADIATION TREATMENT FOR ADVANCED PANCREATIC CANCER

CROSS REFERENCE TO RELATED APPLICATIONS

This application is a U.S. national phase application filed under 35 U.S.C. § 371 claiming benefit to International Patent Application No. PCT/US2019/056927, filed Oct. 18, 2019, which is entitled to priority under 35 U.S.C. § 119 (e) to U.S. Provisional Application No. 62/747,830, filed Oct. 19, 2018, each of which applications is hereby incorporated herein by reference in its entirety.

BACKGROUND OF THE INVENTION

Pancreatic cancer (PC) is the twelfth most common malignancy worldwide, however, it is the seventh leading cause of cancer-associated deaths due to disease aggressiveness (UK CR. Pancreatic Cancer Statistics, 2018; www.cancerresearchuk.org/health-professional/cancer-statistics/statistics-by-cancer-type/pancreatic-cancer). Poor survival statistics are the result of common dysfunctions in core signaling pathways including growth (KRAS), DNA damage control (TP53), and cell cycle regulation (CDKN2A) (Jones et al., 2008, Science, 321(5897):1801-1806). These aberrations drive rapid disease progression prior to symptom onset, increasing the prevalence of locally advanced tumors (LAPC) at the time of primary intervention (Hidalgo et al., 2015, Pancreatology, 15(1):8-18). Currently, the only cure for PC is surgical resection, however, 80-90% of newly diagnosed patients are deemed inoperable, and neoadjuvant therapy is unsuccessful in downstaging approximately 90% of advanced/unresectable lesions (Gillen et al., 2010, PLoS Med, 7(4):e1000267).

Whereas a multitude of chemotherapy/chemoradiation regimens are incapable of downsizing most LAPC malignancies, an emerging strategy, stereotactic body radiation therapy (SBRT), has shown promise (Zhong et al., 2017, Cancer, 123(18):3486-3493). Unlike conventional radiation therapy (conRT) that delivers a low dose, hyperfractionated schedule, SBRT utilizes high doses precisely targeted to the tumor using multiple beam angles. A radioequivalent dose of SBRT can be delivered in 4-5 fractions, affording greater tumoricidal capacity with less damage to surrounding normal tissue (Timmerman et al., 2014, J Clin Oncol, 32(26): 2847-2854). Additionally, by minimizing systemic leukocyte cytotoxicity, tumor neoantigens unmasked during radiation-induced necrosis can be used to prime infiltrating T cells and mount a potent immunogenic response (Order, 1977, Cancer, 39(2 Suppl):737-43). Radiation therapy can also promote leukocyte homing through modulating the intratumoral (IT) chemoattractant milieu and altering stromal architecture to promote extravasation (Lugade et al., 2008, J Immunol, 180(5):3132-3139). However, while RT can induce a potent proinflammatory response by recruiting natural killer and effector T cells, it can also attract a variety of immunosuppressive cell types including inflammatory monocytes (IMs), tumor-associated macrophages (TAMs), myeloid-derived suppressor cells (MDSCs), and regulatory T cells (Walle et al., 2018, Ther Adv Med Oncol, 10:1758834017742575).

The mixed immune-modulatory effects of RT make it an attractive combination for immunotherapy. Still in its infancy, combination immunotherapy in PC has most often utilized dual checkpoint inhibitors or checkpoint inhibition in the setting of chemotherapy, and results have yet to demonstrate notable benefit (Thind et al., 2017, Therap Adv Gastroenterol, 10(1):168-194). Whereas certain cytotoxic chemotherapies such as platinum-based agents have been shown to induce immunogenic cell death, at high dose they can also cause neutropenia and leukopenia (Pfirschke et al., 2016, Immunity, 44(2):343-354; Oun et al., 2018, Dalton Trans, 47(19):6645-6653). Furthermore, failed T cell priming and high suppressor cell distributions in immunologically "cold" tumors, such as PC, commonly lead to resistance of immune checkpoint blockade (Vonderheide, 2018, Cancer cell, 33(4):563-569; Jenkins et al., 2018, British journal of cancer, 118(1):9-16). The pleiotropic cytokine interleukin 12 (IL-12) is well known for its antitumor potential by means of stimulating T cell activation both directly, and indirectly via increased antigen presentation and immunogenic reprogramming of both lymphoid and myeloid-derived suppressor cells (Zeh et al., 1993, J Immunother Emphasis Tumor Immunol, 14(2):155-161; Suzuki et al., 1998, Tohoku J Exp Med, 185(3):223-226; Trinchieri et al., 1992, Prog Growth Factor Res, 4(4):355-368; Kerkar et al., 2011, J Clin Invest, 121(12):4746-4757). However, translational studies of IL-12 demonstrated underwhelming therapeutic effects, and trials were short-lived due to severe toxicities resulting from bolus systemic administration (Jenks, 1996, Journal of the National Cancer Institute, 88(9):576-577).

Accordingly, there exists a need for improved methods and compositions for the prevention and treatment of unresectable prostate cancer. The present invention meets this unmet need.

SUMMARY OF THE INVENTION

In one embodiment, the invention relates to a method for treating an unresectable pancreatic cancer tumor in a subject in need thereof, comprising: a) administering to said tumor an effective amount of ionizing radiation; and b) administering to said subject an effective amount of a composition comprising an immunomodulatory cytokine.

In one embodiment, said ionizing radiation comprises X-rays, gamma rays, electrons or high linear energy transfer (LET) radiation.

In one embodiment, said composition comprises a microparticle or nanoparticle.

In one embodiment, the microparticle or nanoparticle comprises a semi-crystalline matrix.

In one embodiment, the immunomodulatory cytokine is entrapped in the semi-crystalline matrix.

In one embodiment, said immunomodulatory cytokine comprises IL-12.

In one embodiment, said ionizing radiation is administered as a targeted radiation therapy.

In one embodiment, said targeted radiation therapy is hypofractionated tumor directed radiotherapy or stereotactic body radiation therapy (SBRT).

In one embodiment, the targeted radiation therapy is administered by way of a regimen consisting of: 3-8Gy/fraction given in 3-8 fractions.

In one embodiment, said composition is administered concurrently with said ionizing radiation. In one embodiment, said composition is administered subsequent to said ionizing radiation. In one embodiment, said composition is administered prior to said ionizing radiation.

In one embodiment, said composition is administered by intra-tumoral injection.

In one embodiment, a single dosage comprising 0.5 μg to 1000 mg of said composition is administered.

In one embodiment, multiple dosages of said composition, wherein each dosage comprises 0.5 μg to 1000 mg of said composition, are administered.

In one embodiment, the unresectable pancreatic cancer tumor is a locally advanced pancreatic cancer tumor (LAPC) or a metastatic advanced pancreatic cancer tumor.

In one embodiment, said subject is a mammal. In one embodiment, said subject is a human.

BRIEF DESCRIPTION OF THE DRAWINGS

The foregoing summary, as well as the following detailed description of exemplary embodiments of the invention, will be better understood when read in conjunction with the appended drawings. It should be understood, however, that the invention is not limited to the precise arrangements and instrumentalities of the embodiments shown in the drawings.

FIG. 1, comprising FIG. 1A through FIG. 1M, depicts exemplary experimental results demonstrating that SBRT recruits CD8 T cells into the center of human PDA tumors and is superior to conRT. FIG. 1A through FIG. 1L depict representative (20×) CD8 (FIG. 1A through FIG. 1D) and CD68 (FIG. 1G through FIG. 1J) immunoperoxidase stains of human PDA sections that were previously untreated (n=5 patients) or treated with SBRT only (n=7 patients). Tumor center (UI [unirradiated], FIG. 1A and FIG. 1G; SBRT, FIG. 1C and FIG. 1I) and margins (UI, FIG. 1B and FIG. 1H; SBRT, FIG. 1D and FIG. 1J) were analyzed. The number of events per 1 mm² high power field (HPF) as well as the center:margin distribution were calculated for CD8+ (FIG. 1E and FIG. 1F, respectively) and CD68+ (FIG. 1K and FIG. 1L, respectively) cells. Center:margin cell ratios were calculated within each sample prior to averaging; data shown as mean±SEM, t test. FIG. 1M and FIG. 1N depict experiments demonstrating that KCKO-luc cells were orthotopically implanted on day 0 (n=4-6) with two titanium fiducial clips for radiation therapy targeting. SBRT (6 Gy 3 4 days) or conRT (2 Gy 3 15 days) was delivered using the SARRP platform (or UI sham surgery with fiducial clip implantation). FIG. 1M depicts that bioluminescent imaging was performed using the IVIS spectrum. Values are presented as the geometric mean of maximum photon emissions (bioluminescence, BLI) within tumor regions of interest (ROIs); Holm-Sidak test, significance relative to UI/empty MS group. FIG. 1N depicts the corresponding survival curve of UI/SBRT/conRT mice; Grehan-Breslow-Wilcoxon test, UI/SBRT plots are representative of at least two independent experiments. **p<0.01.

FIG. 2, comprising FIG. 2A through FIG. 2F, depicts exemplary experimental results demonstrating that SBRT and IL-12 MS combination greatly reduces PDA tumor burden and increases survival. Tumor cells were implanted on day 0 with two metal fiducial clips for SBRT targeting. SBRT was delivered (6 Gy 3 4 days, or sham surgery with fiducial clip implantation) beginning on day 6 (day 3 for KPC GEMM), followed by i.t. microsphere injection of empty MS control or IL-12 MS on day 10 (day 7 for KPC GEMM).

FIG. 2A depicts a schematic outlining orthotopic PDA mouse model and treatment scheduling. Green arrow points to tumor; white arrows point to fiducial clips. FIG. 2B and FIG. 2C depict exemplary experimental results demonstrating that SBRT/IL-12 MS-treated KCKO-luc orthotopic tumors (n=4-5) were tracked over time using IVIS bioluminescent imaging to measure tumor growth (FIG. 2B), as well as survival analysis (FIG. 2C); representative of 2-3 independent experiments. FIG. 2D and FIG. 2E depict exemplary experimental results demonstrating IVIS growth (FIG. 2D) and survival (FIG. 2E) measurements were repeated on SBRT/IL-12 MS-treated Pan02-luc orthotopic tumors (n=5); representative of 2 independent experiments. FIG. 2F depict exemplary experimental results demonstrating the survival analysis of the SBRT/IL-12 MS-treated KPC GEMM. KPC mice (n=4-8) were manually palpated for pancreatic lesions beginning at 5 weeks of age, and all treatments were initiated when mice reached approximately 6 to 8 weeks of age; mice were dichotomized into treatment groups based on initial tumor weights (day 0=clip implantation). "LTS" designates the long-term survivor further described in the supplement. Representative of 4-6 pooled independent experiments. For each IVIS imaging analysis, values are presented as the geometric mean of maximum photon emissions within ROIs; Holm-Sidak tests. For survival analyses, Grehan-Breslow-Wilcoxon tests were performed. All significance relative to UI/empty MS group. *p<0.05, p<0.01, *p<0.001.

FIG. 3, comprising FIG. 3A depicts IVIS representative heatmaps of tumor-bearing mice 2-hours post-injection. FIG. 3B and FIG. 3D depict exemplary experimental results demonstrating that plasma was collected from tumor-bearing mice prior to sacrifice at 2-hours post-injection. FIG. 3B depicts that tumors were whole-mounted on coverslips for fluorescence microscopy. Plasma was stained for CD45 and CD11b markers prior to imaging flow cytometric analysis. Representative images (FIG. 3C) and quantitation (FIG. 3D) illustrate free flowing AF594 MS in the plasma and engulfment by CD45+/CD11b+ myeloid cells.

FIG. 4 comprising FIG. 4A through FIG. 4E depict exemplary data demonstrating that tumor cells were implanted on day 0 (1×10⁵ cells in 50 μL 1:1 PBS/Matrigel) with two metal fiducial clips for SBRT targeting. SBRT was delivered (6 Gy×4 days, or sham surgery with fiducial clip implantation) beginning on day 6, followed by i.t. microsphere injection of Empty MS control (2 mg beads in 20 μL PBS) or IL-12 MS (2 mg beads containing 0.5 μg recombinant IL-12 in 20 μL PBS) on day 10 (n=1). For IVIS imaging (FIG. 4A), SBRT/IL-12 MS-treated tumor-bearing mice were administered 2.5 mg D-luciferin s.c., (in 100 μL PBS) and representative heatmaps of maximum photon emissions and target ROIs (red circles) are presented for each treatment group (day 13). Hematoxylin and eosin staining was performed on tumors at day 11 and 20× representative images of each treatment group (FIG. 4A through FIG. 4E) are presented. Representative of 1 experiment. (FIG. 4F through FIG. 4I) KPC mice (n=4-8) were manually palpated for pancreatic lesions beginning at five weeks of age, and all treatments were initiated when mice reached approximately six to eight weeks of age. Mice were dichotomized into treatment groups based on initial tumor weights (day 0=clip implantation). SBRT was delivered (6 Gy×4 days, or sham surgery with fiducial clip implantation) beginning on day 3, followed by i.t. microsphere injection of Empty MS control (2 mg beads in 20 µL PBS) or IL-12 MS (2 mg beads containing 0.5 µg recombinant IL-12 in 20 µL PBS) on day 7. Caliper measurements (FIG. 4F) were used to determine tumor volume (during fiducial clip implantation) for dichotomization into treatment groups; Holm-Sidak test. Hematoxylin and eosin staining was performed on tumors at day 10-11 and 20× representative images of UI/Empty MS and SBRT/IL-12 MS treatment groups (FIG. 4G and FIG. 4H, respectively) are presented. Representative images of spleens and pancreatic tumors (FIG. 4I) at time of death. Left: SBRT/IL-12 MS-treated long-term survivor (LTS) demonstrating splenomegaly and minimal tumor burden. Right: Average KPC tumor at autopsy; nearly double the pretreatment volume. Representative of 4-6 pooled independent experiments.

FIG. 5, comprising FIG. 5A through FIG. 5B, depicts exemplary data demonstrating that SBRT/IL-12 MS therapeutic efficacy is dependent upon IFNγ function (FIG. 5A) SBRT/IL-12 MS-treated KCKO-luc orthotopic tumors (n=3) were harvested on days 11/12/13 and homogenized prior to Luminex cytokine multiplex assay analysis. Data values (pg/mL) were normalized to total protein content and are presented in pg/mg protein; Holm-Sidak test, representative of at least 2 independent experiments. FIG. 5B and FIG. 5C depict SBRT/IL-12 MS-treated KCKO-luc orthotopic tumors (n=5) were harvested on day 11 and digested into single cell suspensions for flow cytometric analysis. Fluorescence minus one (FMO) controls were used to identify IFNγ$^+$ cells from CD45$^+$ (FIG. 5B) and CD45$^+$CD4$^+$ (FIG. 5C) immune cell populations. Values are presented as percent IFNγ+ of total CD45$^+$ cells identified (right panels); Holm-Sidak test, representative of at least 2 independent experiments.

FIG. 6, comprising FIG. 6A depicts a representative flow cytometry gating strategy used to identify IM and TAM populations. FIG. 6B depicts that IM and TAM population densities were assessed using flow cytometry and are presented as a percentage of total CD45$^+$ cells identified; Holm-Sidak tests, representative of 2 independent experiments. FIG. 6C depicts that FMO controls were used to gate MHCII$^+$ (left panel: wild-type [WT] host; right panel: Ifng$^{-/-}$ host) IMs. Dotplot values represent mean fluorescence intensity (WT), and percentages of positive cells are represented in the upper right corner of each plot; Holm-Sidak tests, representative of at least two independent experiments. FIG. 6D and FIG. 6E depict IM (D, n=3) and TAM (E, n=2-3) populations were flow sorted prior to RNA-seq analyses. SBRT/IL-12 MS DEGs (versus UI/empty MS controls) were compared to monocyte, classical M1, and alternative M2 macrophage genesets from the Broad Institute MSigDB (MSigDB: GSE5099), and gene matches are presented in volcano plots. Blue, downregulated; red, upregulated. Representative of one experiment. FIG. 6G depicts that transplanted tumors were measured over time by using IVIS bioluminescent imaging to track tumor growth. The geometric means of maximum photon emissions within ROIs were normalized to KCKO-luc-only control tumors and presented as fold change relative to day 3 tumor size; Holm-Sidak test, all significance relative to UI/empty MS group, except UI/empty MS, which is relative to KCKO-luc-only control. Representative of one experiment. *p<0.05, p<0.01, *p<0.001, ****p<0.0001.

FIG. 7, comprising FIG. 7A depicts a flow cytometry gating strategy used to identify TANs (top panel), and TAN population density as a percentage of total CD45+ cells (bottom panel). FIG. 7B depicts that FMO controls were used to gate MHCII+ TAMs. Dotplot values represent mean fluorescence intensity (MFI) and percentages of positive cells are represented in the lower right corner of each plot; Holm-Sidak tests; representative of at least two independent experiments. FIG. 7C depicts IM and TAM populations were flow sorted prior to RNA-seq analyses. DEGs (vs. UI/Empty MS controls) were clustered using Ingenuity Pathway Analysis. Significantly altered pathways are documented and activation z-scores are presented for each comparison in heatmap format.

FIG. 8, comprising

FIG. 9, comprising FIG. 9A depicts representative flow cytometry gating strategy used to identify CD8 and CD4 T cell, and Treg populations. FIG. 4B depicts that CD8 and CD4 T cell population densities were assessed on days 11 (left panels) and 14 (right panels) by using flow cytometry and are presented as a percentage of total CD45+ cells identified; Holm-Sidak tests, representative of at least two independent experiments. FIG. 9C $T_{reg}$ cell percentages (top panels) and CD8:$T_{reg}$ ratios (bottom panels) were analyzed on day 11 in tumors grown in WT (left panels) and Ifng$^{-/-}$ (right panels) mice; Holm-Sidak tests, representative of at least two independent experiments. FIG. 9D depicts that SBRT/IL-12 MS-treated KCKO-luc orthotopic tumors (n=4) were administered immunoglobulin G (IgG) control or anti-CD8- or anti-CD4-depleting antibodies every three days between days 5 and 20 post-implantations. Tumor size was measured over time using IVIS bioluminescent imaging. Values are presented as the geometric mean of maximum photon emissions within ROIs; Holm-Sidak test, significance relative to UI/empty MS group, pooled data from two independent experiments. *$p<0.05$, $p<0.01$, *$p<0.001$, ****$p<0.0001$.

FIG. 11, comprising FIG. 11A through FIG. 11D depict the flow cytometry gating strategies and population densities (as percentages of total CD45$^+$ cells) of APCs (FIG. 11A), B cells (FIG. 11B), NK cells (FIG. 11C), and CD8+NK1.1$^+$ cells (FIG. 11D). Holm-Sidak tests; representative of at least two independent experiments. FIG. 11E depicts a flow cytometric analysis of day 14 KCKO-luc orthotopic tumors (n=4-5) for $T_{reg}$ population density as a percentage of total CD45+ cells; Holm-Sidak test, representative of at least two independent experiments. *$p<0.05$, **$p<0.01$.

FIG. 12, comprising FIG. 12A depicts FMO controls were used to gate CD44+ (far-left panel), CD107a+ (mid-left panel), CTLA4+ (mid-right panel), and PD1+ (far-right panel) CD8 T cells. Dotplot values represent mean fluorescence intensity (MFI) and percentages/MFI of positive cells are represented in the upper right corner of each plot; Holm-Sidak tests. Representative of at least two independent experiments. FIG. 12B depicts that tumors were homogenized prior to Luminex cytokine multiplex assay analysis. Data values (pg/mL) were normalized to total protein content and are presented in pg/mg protein; Holm-Sidak test. Representative of at least two independent experiments. FIG. 12C depicts CD8$^+$ T cells were flow sorted from tumors for RNA-seq analysis. DEGs (vs. UI/Empty MS controls) were clustered using Ingenuity Pathway Analysis comparing each of the 3 treatment groups to UI/Empty MS controls. Significantly altered pathways are documented and activation z-scores are presented for each comparison in heatmap format. Representative of one independent experiment. *$p<0.05$, **$p<0.01$.

FIG. 13, comprising FIG. 13A through FIG. 13G, depicts exemplary experimental data demonstrating SBRT/IL-12 MS therapy generates systemic antitumor immunity that drives an abscopal effect. FIG. 13A and FIG. 13B depict that mice cured of primary KCKO-luc tumors by SBRT/IL-12 MS treatment (n=5) were rechallenged after 6 months by delivering KCKO-luc cells to the liver by using the hemi-spleen metastatic model. Rechallenged mice did not receive any second-line therapy. Liver tumors were followed over time using IVIS bioluminescent imaging to measure growth (FIG. 13A), as well as survival analysis (FIG. 13B). For IVIS imaging analysis, the treatment-naive line plot represents the geometric mean of 5 individual mice, while SBRT/IL-12 MS line plots represent individual mice. Representative of 2 independent experiments. FIG. 13C and FIG. 13D depict that mice that survived hemi-spleen rechallenge, in addition to age-matched tumor or treatment-naive donors (n=5), were sacrificed after 3.5 months, and CD8$^+$ T cells from the spleen and lymph nodes were isolated using negative selection. Donor CD8 T cells were transplanted 1:1 into naive recipients 16 hours prior to KCKO-luc implantation. Tumor-bearing CD8 T cell recipient mice did not receive any additional treatment, and tumors were followed over time by using IVIS bioluminescent imaging (FIG. 13C) to measure growth. The transferal of partial (>10-fold decrease in bioluminescent tumor volume) and full (unidentifiable tumor by manual palpation) immunity is represented in a pie chart (FIG. 13D) as a percentage of total SBRT/IL-12 MS-cured donors. For IVIS imaging analysis, the treatment-naive line plot represents the geometric mean of 5 individual mice, while the SBRT/IL-12 MS line plots represent individual mice. Representative of one experiment. FIG. 13E through FIG. 13G depict that KCKO-luc cells were implanted on day 0 (n=5) into the liver by using the hemi-spleen model, whereas KCKO cells were simultaneously injected into the pancreas. The SBRT/IL-12 MS treatment paradigm (FIG. 13C and FIG. 13D) was followed for the treatment of primary pancreas tumors only (FIG. 13E). KCKO-luc liver metastases were tracked over time by sing IVIS bioluminescent imaging to measure metastatic growth (FIG. 13F), as well as survival analysis (FIG. 13G). For IVIS imaging analysis, values are presented as the geometric mean of maximum photon emissions within ROIs; Holm-Sidak tests, representative of two independent experiments. For each survival analysis, Grehan-Breslow-Wilcoxon tests were performed. All significance relative to UI/empty MS group. **$p<0.01$.

FIG. 14, comprising FIG. 14A depicts representative heatmaps of maximum photon emissions and ROIs are presented for each treatment group (day 14). FIG. 14B depicts KCKO-luc tumor growth as measured by IVIS bioluminescence in 6-8-week old mice. Representative of two independent experiments. FIG. 14C through FIG. 14F depicts that KCKO-luc cells were implanted on day 0 (n=5) into both the pancreas and leg of each mouse (5×10$^4$ cells per injection). The SBRT/IL-12 MS treatment paradigm was followed for the treatment of pancreas tumors only. For IVIS imaging, SBRT/IL-12 MS-treated tumor-bearing mice were administered 2.5 mg D-luciferin s.c. (in 100 μL PBS), and representative heatmaps of maximum photon emissions (FIG. 14C) are presented for each treatment group (day 13) that illustrate non-overlapping primary and secondary tumor ROIs. IVIS imaging was used to measure primary (pancreas, FIG. 14D) and secondary (leg, FIG. 14E, left panel) tumor growth over time. Caliper measurements were also used to determine mean leg tumor diameter over time (FIG. 14E, middle panel), as well as to identify the percentage of tumor-free mice (FIG. 14E, right panel) per group over time. Leg caliper measurement values represent the average of two measurements per tumor per timepoint; Holm-Sidak test, representative of one experiment. (FIG. 14F) SBRT/IL-12 MS-treated KCKO-luc orthotopic tumors (n=5) were harvested on day 11 and homogenized prior to Luminex cytokine multiplex assay analysis. Data values (pg/mL) were normalized to total protein content and are presented in pg/mg protein; Holm-Sidak test. For each IVIS imaging analysis, values are presented as the geometric mean of maximum photon emissions within ROIs; Holm-Sidak tests, representative of two independent experiments. All significance relative to UI/Empty MS group. *$p<0.05$, $p<0.01$, *$p<0.001$, ****$p<0.0001$.

FIG. 15, comprising FIG. 15A depicts that PDA tumorigenesis is highlighted by marked infiltration of immunosuppressive $T_{reg}$ cells, IMs that seed TAM populations, and a paucity of CD8 T cells in the lesion periphery. FIG. 15B depicts that SBRT initiates necrotic cell death that produces tumor antigen necessary for $T_{eff}$ formation in the DLN. Increases in intratumoral CD8 $T_{eff}$ cells have modest antitumor effects due to the ancillary recruitment of $T_{reg}$ and IM/TAM suppressors. FIG. 15C depicts that IL-12 MS treatment stimulates intratumoral T effectors to produce IFNγ, which initiates $T_h1$ repolarization of $T_{regs}$, activation of IMs (adding to IFNγ pools) and M1 reprogramming of TAMs. The actuation of $T_{eff}$ cell number and function elicits marked tumor cell apoptosis. FIG. 15D depicts that the resolution of PDA tumors is highlighted by $T_{reg}$ rebound and them formation, resulting in lasting tumor-specific immune memory.

DETAILED DESCRIPTION OF THE INVENTION

Figures 1M, 1N:
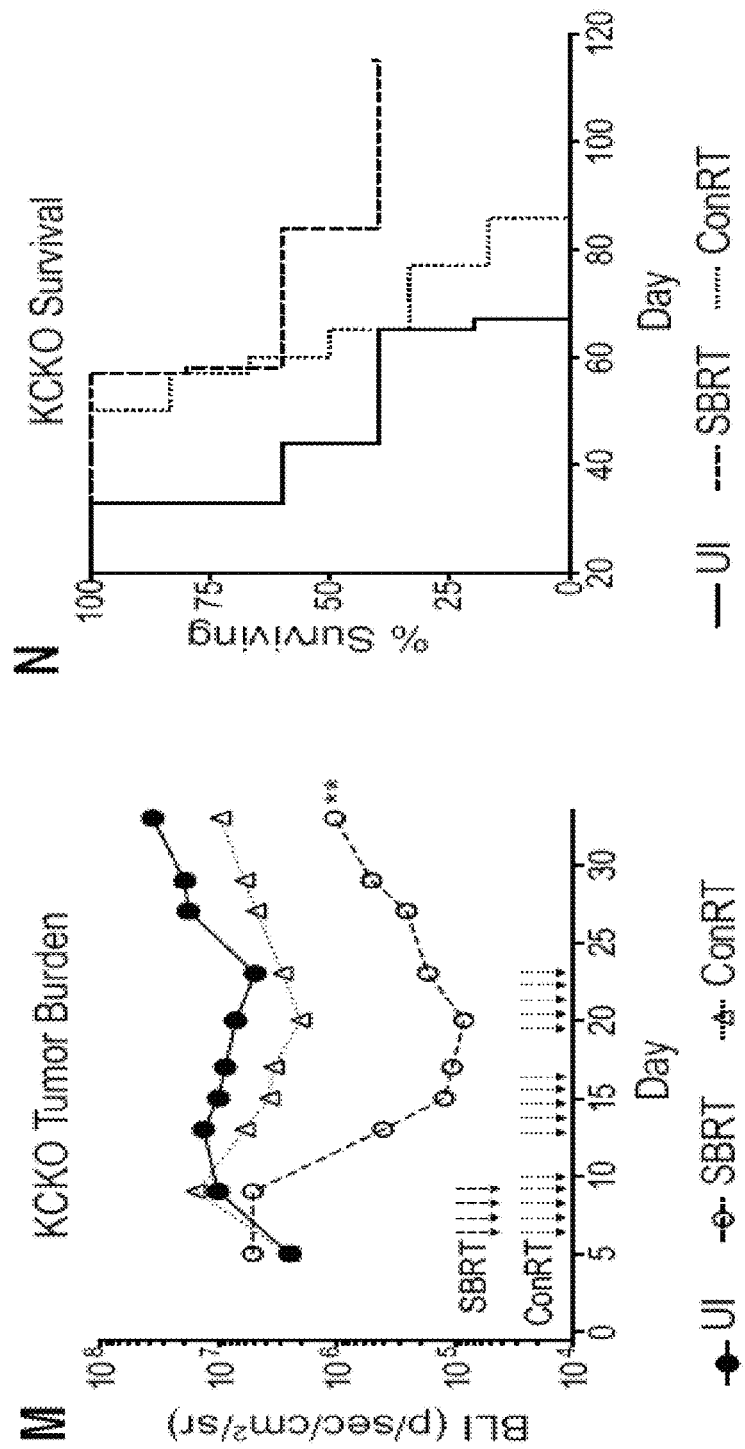

The methods described herein provide the advantages of anti-tumor efficacy and normal tissue protection when combining an immune modulator with ionizing radiation to treat unresectable pancreatic cancer. The methods described herein provide the unexpected result that ionizing radiation in combination with immune modulator therapy increases the anti-tumor response compared to treatment with radiation therapy or immune modulator therapy alone. The increase in the anti-tumor response can enhance or increase the inhibition of tumor growth that is provided by either monotherapy alone. Methods described herein can be used to treat local advanced and metastatic pancreatic cancers by administering (1) ionizing radiation therapy to deliver a highly conformal dose to the tumor, and (2) an immune modulator. The combination of radiation and immune modulator enhances the anti-cancer response, as compared to administration of either an immune modulator alone or radiation monotherapy.

Definitions

Unless defined otherwise, all technical and scientific terms used herein have the same meaning as commonly understood by one of ordinary skill in the art to which this invention belongs.

Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, NY, and Ausubel et al., 2012, Current Protocols in Molecular Biology, John Wiley & Sons, NY), which are provided throughout this document.

The nomenclature used herein and the laboratory procedures used in analytical chemistry and organic syntheses described below are those well-known and commonly employed in the art. Standard techniques or modifications thereof are used for chemical syntheses and chemical analyses.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, or ±10%, or ±5%, or ±1%, or ±0.1% from the specified value, as such variations are appropriate to perform the disclosed methods.

"Biocompatible" and "biologically compatible", as used herein, refer to materials that are, along with any metabolites or degradation products thereof, generally non-toxic to the recipient, and do not cause any significant adverse effects to the recipient, at concentrations resulting from the degradation of the administered materials. Generally speaking, biocompatible materials are materials that do not elicit a significant inflammatory or immune response when administered to a patient.

Biodegradable, as defined herein, means the composition will degrade or erode in vivo to form smaller chemical species. Degradation can result, for example, by enzymatic, chemical and physical processes.

The term "cancer" as used herein is defined as disease characterized by the abnormal growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer (e.g., melanoma), pancreatic cancer, colorectal cancer, renal cancer, liver cancer, brain cancer, lymphoma, leukemia, lung cancer, sarcoma and the like.

As used herein, "conjugated" refers to covalent attachment of one molecule to a second molecule.

As used herein, the term "derivative" includes a chemical modification of a polypeptide, polynucleotide, or other molecule. In the context of this invention, a "derivative polypeptide," for example, one modified by glycosylation, pegylation, or any similar process, retains binding activity. For example, the term "derivative" of binding domain includes binding domain fusion proteins, variants, or fragments that have been chemically modified, as, for example, by addition of one or more polyethylene glycol molecules, sugars, phosphates, and/or other such molecules, where the molecule or molecules are not naturally attached to wild-type binding domain fusion proteins. A "derivative" of a polypeptide further includes those polypeptides that are "derived" from a reference polypeptide by having, for example, amino acid substitutions, deletions, or insertions relative to a reference polypeptide. Thus, a polypeptide may be "derived" from a wild-type polypeptide or from any other polypeptide. As used herein, a compound, including polypeptides, may also be "derived" from a particular source, for example from a particular organism, tissue type, or from a particular polypeptide, nucleic acid, or other compound that is present in a particular organism or a particular tissue type.

The term "DNA" as used herein is defined as deoxyribonucleic acid.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The term "inhibit," as used herein, means to suppress or block an activity or function, for example, about ten percent relative to a control value. In one embodiment, the activity is suppressed or blocked by at least 50% compared to a control value, at least 75% compared to a control value, or at least 95% compared to a control value. "Inhibit," as used herein, also means to reduce the level of a molecule, a reaction, an interaction, a gene, an mRNA, and/or a protein's expression, stability, function or activity by a measurable amount or to prevent entirely. Inhibitors are compounds that, e.g., bind to, partially or totally block activity, decrease, prevent, delay activation, inactivate, desensitize, or down regulate a protein, a gene, and an mRNA stability, expression, function and activity, e.g., antagonists.

As used herein, the term "matrix" refers to a three-dimensional network of polymeric compounds. The polymeric compounds are arranged in such a way as to permit the inclusion of other compounds inside the three dimensional network.

The terms "modulator" and "modulation" of a molecule of interest, as used herein in its various forms, is intended to encompass antagonism, agonism, partial antagonism and/or partial agonism of an activity associated with the immune response. In various embodiments, "modulators" may inhibit or stimulate the immune response or an activity associated with the immune response. Such modulators include small molecules agonists and antagonists of a protease molecule, antisense molecules, ribozymes, triplex molecules, and RNAi polynucleotides, and others.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Isolated" means altered or removed from the natural state. For example, a nucleic acid or a peptide naturally present in its normal context in a living animal is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine. The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the term "microparticle" generally refers to a particle having a diameter, from about 1 micron to about 100 microns, for example, from about 1 to about 50 microns, from about 1 to about 30 microns, and from about 1 micron to about 10 microns. The microparticles can have any shape. Microparticles having a spherical shape may be referred to as "microspheres."

As used herein, the term "nanoparticle" generally refers to a particle having a diameter from about 1 nanometer to 1000 nanometers, for example, from about 10 nanometers to 1000 nanometers, from about 100 nanometers to 1000 nanometers, and from about 250 nanometers to 1000 nanometers. The nanoparticles can have any shape. Nanoparticles having a spherical shape may be referred to as "nanospheres."

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "conservative substitution," when describing a polypeptide, refers to a change in the amino acid composition of the polypeptide that does not substantially alter the activity of the polypeptide, i.e., substitution of amino acids with other amino acids having similar properties. Conservative substitution tables providing functionally similar amino acids are well known in the art. The following six groups each contain amino acids that are generally understood to represent conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W) (see also, Creighton, 1984, Proteins, W.H. Freeman and Company). In addition to the above-defined conservative substitutions, other modifications of amino acid residues can also result in "conservatively modified variants." For example, one may regard all charged amino acids as substitutions for each other whether they are positive or negative. In addition, conservatively modified variants can also result from individual substitutions, deletions or additions which alter, add or delete a single amino acid or a small percentage of amino acids, for example, often less than 5%, in an encoded sequence. Further, a conservatively modified variant can be made from a recombinant polypeptide by substituting a codon for an amino acid employed by the native or wild-type gene with a different codon for the same amino acid.

The term "RNA" as used herein is defined as ribonucleic acid. The term "recombinant DNA" as used herein is defined as DNA produced by joining pieces of DNA from different sources.

By "pharmaceutically acceptable" it is meant, for example, a carrier, diluent or excipient that is compatible with the other ingredients of the formulation and generally safe for administration to a recipient thereof. As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well-known conventional methods.

The terms "patient," "subject," "individual," and the like are used interchangeably herein, and refer to any animal, including a human, in need of therapy for, or susceptible to, a condition or its sequelae. Thus, the individual may include, for example, dogs, cats, pigs, cows, sheep, goats, horses, rats, monkeys, and mice and humans.

A "therapeutic" treatment is a treatment administered to a subject who exhibits signs of pathology, for the purpose of diminishing or eliminating those signs.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "treat," "treating," and "treatment," refer to therapeutic or preventative measures described herein. The methods of "treatment" employ administration to a subject, in need of such treatment, a composition of the present invention, for example, a subject afflicted a disease or disorder, including pancreatic cancer, or a subject who ultimately may acquire such a disease or disorder, including pancreatic cancer, in order to prevent, cure, delay, reduce the severity of, or ameliorate one or more symptoms of the disorder or recurring disorder, or in order to prolong the survival of a subject beyond that expected in the absence of such treatment.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present disclosure describes methods for treating a metastatic or unresectable pancreatic cancer in a subject by administering ionizing radiation in combination with one or more immune modulators. Methods described herein can be used to treat local advanced and metastatic pancreatic cancers by administering ionizing radiation therapy to the tumor, and an immune modulator. In one embodiment, the immune modulator is administered intratumorally.

In one aspect, a method for treating a tumor in a subject with cancer comprising administering ionizing radiation and an immune modulator to the tumor is provided. The immune modulator can be selected from the group consisting of an inhibitor to an inhibitory checkpoint molecule, an activator of a stimulatory checkpoint molecule, a chemokine inhibitor, an inhibitor of macrophage migration inhibitory factor (MIF), a growth factor, a cytokine, an interleukin, an interferon, an antibody that binds to an immune system cell, such as a bispecific antibody that binds to T-cells and a tumor antigen, a cellular immune modulator such as a CAR-T cell, a vaccine, an oncolytic virus, and any combination thereof. In some embodiments, the immune modulator is an immunomodulatory cytokine. In one embodiment, the immunomodulatory cytokine is IL-12.

In certain instances, the ionizing radiation is administered as a hypofractionated radiation treatment. The ionizing radiation and the immune modulator can be administered concomitantly. Alternatively, the ionizing radiation and the immune modulator can be administered sequentially.

In another aspect, provided herein is a method of treating a tumor in a subject with cancer comprising: administering to the tumor in the subject a treatment comprising ionizing radiation and an immune modulator. In some instances, the method further comprises contacting the tumor with a radiosensitizer. The ionizing radiation can be administered as a hypofractionated radiation treatment The methods described herein can also include performing functional imaging of the tumor prior to administering the ionizing radiation and the immune modulator. In some embodiments, imaging of the tumor, such as functional imaging is used to identify or select a cancer patient who should receive the combination therapy described herein. Non-limiting examples of functional imaging include single-photon emission computed tomography, optical imaging, ultrasonography, positron emission tomography (PET), computed tomography (CT), perfusion computed tomography, magnetic resonance imaging (MRI), functional magnetic resonance imaging, magnetic resonance sectroscopic imaging, dynamic contrast-enhanced imaging, diffusion-weighted imaging, blood-oxygenation level dependent imaging, magnetic resonance spectroscopy, magnetic resonance lymphography, and any combination thereof. Any type of functional imaging such as multimodality imaging can be performed to characterize the tumor, to determine the delineation of the tumor, the extent of the tumor, the tumor volume, and/or to assess the tumor microenvironment (e.g., the environment surrounding the tumor). Functional imaging can aid in selecting the best treatment option and/or in monitoring response to the treatment.

In some embodiments, the treatment comprises administering ionizing radiation to the tumor in the subject. In some embodiments, the ionizing radiation can be administered to the entire subject, especially if the tumor is dispersed or mobile. In some embodiments, the ionizing radiation can be administered locally to a tumor for example by hypofractionated tumor directed radiotherapy or stereotactic body radiation therapy (SBRT).

In some embodiments, the treatment further comprises contacting the tumor with a radiosensitizer. In some embodiments, the treatment further comprises administering a compound or biologic drug that modulates the immune response to the subject. Thus, in some embodiments, the treatment comprises administering a standard radiation treatment protocol in combination with an immune modulator.

In some embodiments, the effective dose of ionizing radiation administered to the tumor is based on the standard of care for a subject having an unresectable pancreatic cancer, and the subject is further administered an immune modulator agent. In some embodiments involving an existing course of treatment, the effective dose of ionizing radiation is maintained at the current effective dose, and an immune modulator agent is administered to the subject in combination with the ionizing radiation.

Radiation Therapy

As is well known in the art, the effective dose of ionizing radiation varies with the type of tumor and stage of cancer that needs to be treated. The effective dose can also vary based on other treatment modalities being administered to the patient, for example chemotherapeutic treatments and surgical treatments, and whether the radiation is administered pre- or post-surgery.

The therapeutic dose can be delivered in fractions. Fractionation refers to spreading out the total dose of radiation over time, for example, over days, weeks or months. The dose delivered in each fraction can be about 1.5-2 Gy per day. The treatment plan can include a fraction treatment one or more times per day, every other day, weekly, etc. depending on the treatment needs of each patient. For example, a hypofractionation schedule comprises dividing the total dose into several relatively large doses, and administering the doses at least one day apart. Exemplary hypofraction doses are 3 Gy to 20 Gy per fraction. An exemplary fractionation schedule that can be used to treat unresectable pancreatic cancer is 3 Gy to 8 Gy per fraction administered in 3-8 fractions. For example, in one embodiment, 3 Gy of radiation is administered per fraction in 3 fractions, in 4 fractions, in 5 fractions, in 6 fractions, in 7 fractions, in 8 fractions, or in more than 8 fractions. In one embodiment, 4 Gy of radiation is administered per fraction in 3 fractions, in 4 fractions, in 5 fractions, in 6 fractions, in 7 fractions, in 8 fractions, or in more than 8 fractions. In one embodiment, 5 Gy of radiation is administered per fraction in 3 fractions, in 4 fractions, in 5 fractions, in 6 fractions, in 7 fractions, in 8 fractions, or in more than 8 fractions. In one embodiment, 6 Gy of radiation is administered per fraction in 3 fractions, in 4 fractions, in 5 fractions, in 6 fractions, in 7 fractions, in 8 fractions, or in more than 8 fractions. In one embodiment, 7 Gy of radiation is administered per fraction in 3 fractions, in 4 fractions, in 5 fractions, in 6 fractions, in 7 fractions, in 8 fractions, or in more than 8 fractions. In one embodiment, 8 Gy of radiation is administered per fraction in 3 fractions, in 4 fractions, in 5 fractions, in 6 fractions, in 7 fractions, in 8 fractions, or in more than 8 fractions.

In some embodiments, the ionizing radiation includes contacting the tumor in the subject with a radiosensitizer. Exemplary radiosensitizers include hypoxia radiosensitizers such as misonidazole, metronidazole, and trans-sodium crocetinate, a compound that helps to increase the diffusion of oxygen into hypoxic tumor tissue. The radiosensitizer can also be a DNA damage response inhibitor interfering with base excision repair (BER), nucleotide excision repair (NER), mismatch repair (MMR), recombinational repair comprising homologous recombination (HR) and non-homologous end-joining (NHEJ), and direct repair mechanisms. SSB repair mechanisms include BER, NER, or MMR pathways whilst DSB repair mechanisms consist of HR and NHEJ pathways. Radiation causes DNA breaks that if not repaired are lethal. Single strand breaks are repaired through a combination of BER, NER and MMR mechanisms using the intact DNA strand as a template. The predominant pathway of SSB repair is the BER utilizing a family of related enzymes termed poly-(ADP-ribose) polymerases (PARP). Thus, the radiosensitizer can include DNA damage response inhibitors such as Poly (ADP) ribose polymerase (PARP) inhibitors.

The combination treatment of the invention can be incorporated into a treatment plan. The treatment plan can include visualizing or measuring the tumor volume that needs to be irradiated, the optimal or effective dose of radiation administered to the tumor, and the maximum dose to prevent damage to nearby healthy tissue or organs at risk. Algorithms can used in treatment planning, and include dose calculation algorithms based on the particular radiotherapy technique parameters employed, e.g., gantry angle, MLC leaf positions, etc., and search algorithms which use various techniques to adjust system parameters between dose calculations to optimize the effectiveness of the treatment. Exemplary dose calculation algorithms include various Monte Carlo ("MC") techniques and pencil beam convolution ("PBC"). Exemplary search algorithms include various simulated annealing ("SA") techniques, algebraic inverse treatment planning ("AITP"), and simultaneous iterative inverse treatment planning ("SIITP"). Such techniques, and others, are well known in the art, and are included within the scope of this disclosure.

Treatment planning algorithms may be implemented as part of an integrated treatment planning software package which provides additional features and capabilities. For example, a dose calculation algorithm and search algorithm may be used to optimize a set of fluence maps at each gantry angle, with a separate leaf sequencer used to calculate the leaf movements needed to deliver them. Alternatively, a dose calculation algorithm and search algorithm may be used to directly optimize leaf movements and other machine parameters.

Radiation therapy techniques that can be employed in the methods of the invention include, but are not limited to, external-beam radiotherapy ("EBRT") and Intensity Modulated Radiotherapy ("IMRT"), which can be administered by a radiotherapy system, such as a linear accelerator, equipped with a multileaf collimator ("MLC"). The use of multileaf collimators and IMRT allows the patient to be treated from multiple angles while varying the shape and dose of the radiation beam, thereby avoiding excess irradiation of nearby healthy tissue. Other exemplary radiation therapy techniques include stereotactic body radiotherapy (SBRT), volumetric modulated arc therapy, three-dimensional conformal radiotherapy ("3D conformal" or "3DCRT"), image-guided radiotherapy (IGRT). The radiation therapy techniques can also include Adaptive radiotherapy (ART), a form of IGRT that can revise the treatment during the course of radiotherapy in order to optimize the dose distribution depending on patient anatomy changes, and organ and tumor shape. Another radiation therapy technique is brachytherapy. In brachytherapy, a radioactive source is implanted within the body of the subject, such that the radioactive source is near the tumor. As used herein, the term radiotherapy should be broadly construed and is intended to include various techniques used to irradiate a patient, including use of photons (such as high energy x-rays and gamma rays), particles (such as electron and proton beams), and radiosurgical techniques. Further, any method of providing conformal radiation to a target volume is intended to be within the scope of the present disclosure.

Immune Modulators

The radiation therapy can be administered in combination with one or more immune modulators. The combination therapy can provide an increased anti-tumor response (a positive clinical response) compared to administration of either treatment as monotherapy. In some cases, the immune modulator can be selected from the group consisting of an inhibitor to an inhibitory checkpoint molecule, an activator of a stimulatory checkpoint molecule, a chemokine inhibitor, an inhibitor of macrophage migration inhibitory factor (MIF), a growth factor, a cytokine, an interleukin, an interferon, an antibody that binds to an immune system cell, such as a bispecific antibody that binds to T-cells and a tumor antigen, a cellular immune modulator such as a CAR-T cell, a vaccine, an oncolytic virus, and any combination thereof.

Immune modulators can include small molecules and biologic therapies (e.g., antibodies, fragments thereof, and derivatives thereof) that bind molecules expressed on the surface of immune system cells, such as antigen presenting cells and T-cells. Immune modulators also can include small molecules that inhibit or stimulate the immune system. In some instances, the immune modulator stimulates the production of IFNγ. In one embodiment, the immune modulator is an immunomodulatory cytokine. Immunomodulatory cytokines include, but are not limited to, IL-12 and IL-2.

Peptides

In one embodiment, the immune modulator of the invention may be a protein, peptide, a variant of an immunomodulatory protein, a peptidomimetic or a functional fragment of a protein or peptide. For example, in one embodiment, the immune modulator may be an IL-12 protein, an IL-12 variant, an IL-12 peptidomimetic or a functional fragment of IL-12.

The peptide of the present invention may be made using chemical methods. For example, peptides can be synthesized by solid phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

The peptide may alternatively be made by recombinant means or by cleavage from a longer polypeptide. The composition of a peptide may be confirmed by amino acid analysis or sequencing.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two polypeptides is determined by comparing the amino acid sequence and its conserved amino acid substitutes of one polypeptide to a sequence of a second polypeptide. Variants are defined to include polypeptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to bind to ubiquitin or to a ubiquitylated protein. The present invention includes amino acid sequences that are at least 60%, 65%, 70%, 72%, 74%, 76%, 78%, 80%, 90%, or 95% similar or identical to the original amino acid sequence. The degree of identity between two polypeptides is determined using computer algorithms and methods that are widely known for the persons skilled in the art. For example, the identity between two amino acid sequences can be determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The polypeptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The polypeptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA (tRNALYS), could be modified with an amine specific photoaffinity label.

The term "functionally equivalent" as used herein refers to a polypeptide according to the invention that preferably retains at least one biological function or activity of the specific amino acid sequence of an immunomodulatory protein (e.g., IL-12).

An immune modulator of the invention may be phosphorylated using conventional methods such as the method described in Reedijk et al. (The EMBO Journal 11(4):1365, 1992).

Fusion and Chimeric Polypeptides

An immune modulator of the invention may be conjugated with other molecules, such as proteins, to prepare fusion proteins. This may be accomplished, for example, by the synthesis of N-terminal or C-terminal fusion proteins provided that the resulting fusion protein retains the functionality of the immune modulator.

Cyclic derivatives of the peptides or chimeric proteins of the invention are also part of the present invention. Cyclization may allow the peptide or chimeric protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

(a) Tags

In a particular embodiment of the invention, an immune modulator polypeptide of the invention further comprises the amino acid sequence of a tag. The tag includes but is not limited to: polyhistidine tags (His-tags) (for example H6 and H10, etc.) or other tags for use in IMAC systems, for example, Ni2+ affinity columns, etc., GST fusions, MBP fusions, streptavidine-tags, the BSP biotinylation target sequence of the bacterial enzyme BIRA and tag epitopes that are directed by antibodies (for example c-myc tags, FLAG-tags, among others). As will be observed by a person skilled in the art, the tag peptide can be used for purification, inspection, selection and/or visualization of the fusion protein of the invention. In a particular embodiment of the invention, the tag is a detection tag and/or a purification tag. It will be appreciated that the tag sequence will not interfere in the function of the immune modulator of the invention.

(b) Leader and Secretory Sequences

Accordingly, the immune modulators of the invention can be fused to another polypeptide or tag, such as a leader or secretory sequence or a sequence which is employed for purification or for detection. For example, in one embodiment, the immune modulator of the invention comprises the glutathione-S-transferase protein tag which provides the basis for rapid high-affinity purification of the polypeptide of the invention. Indeed, this GST-fusion protein can then be purified from cells via its high affinity for glutathione. Agarose beads can be coupled to glutathione, and such glutathione-agarose beads bind GST-proteins. Thus, in a particular embodiment of the invention, the polypeptide of the invention is bound to a solid support. In a preferred embodiment, if the polypeptide of the invention comprises a GST moiety, the polypeptide is coupled to a glutathione-modified support. In a particular case, the glutathione modified support is a glutathione-agarose bead. Additionally, a sequence encoding a protease cleavage site can be included between the affinity tag and the polypeptide sequence, thus permitting the removal of the binding tag after incubation with this specific enzyme and thus facilitating the purification of the corresponding protein of interest.

(c) Targeting Sequences

In one embodiment, the immune modulator of the invention comprises, a target protein, and/or a targeting domain capable of directing the immune modulator to a desired cellular component or cell type or tissue. The immune modulators may also contain additional amino acid sequences or domains. In one embodiment, the immune modulators of the invention are recombinant in the sense that the various components are from different sources, and as such are not found together in nature (i.e. are heterologous).

A target protein is a protein that is selected for degradation and for example may be a protein that is mutated or over expressed in a disease or condition. In another embodiment of the invention, a target protein is a protein that is abnormally degraded and for example may be a protein that is mutated or underexpressed in a disease or condition. The targeting domain can be a membrane spanning domain, a membrane binding domain, or a sequence directing the protein to associate with for example vesicles or with the nucleus. The targeting domain can target the immune modulator to a particular cell type or tissue. For example, the targeting domain can be a cell surface ligand or an antibody against cell surface antigens of a target tissue (e.g. neuron or tumor antigens). A targeting domain may target a an immune modulator to a cellular component.

(d) Intracellular Targeting

The immune modulator can be provided a fusion peptide along with a second peptide which promotes "transcytosis", e.g., uptake of the peptide by epithelial cells. To illustrate, the immune modulator of the present invention can be provided as part of a fusion polypeptide with all or a fragment of the N-terminal domain of the HIV protein Tat, e.g., residues 1-72 of Tat or a smaller fragment thereof which can promote transcytosis. In other embodiments, the immune modulator can be provided a fusion polypeptide with all or a portion of the antenopedia III protein.

To further illustrate, immune modulator (or peptidomimetic) can be provided as a chimeric peptide which includes a heterologous peptide sequence ("internalizing peptide") which drives the translocation of an extracellular form of an immune modulator across a cell membrane in order to facilitate intracellular localization of the immune modulator. In this regard, the immune modulator is one which is active intracellularly. The internalizing peptide, by itself, is capable of crossing a cellular membrane by, e.g., transcytosis, at a relatively high rate. The internalizing peptide is conjugated, e.g., as a fusion protein, to the immune modulator. The resulting chimeric peptide is transported into cells at a higher rate relative to the peptide alone to thereby provide a means for enhancing its introduction into cells to which it is applied.

Exemplary internalizing peptides include peptides of apolipoprotein A-1 and B; peptide toxins, such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary internalizing peptides may be modified through attachment of substituents that enhance the alpha-helical character of the internalizing peptide at acidic pH.

Yet another class of internalizing peptides suitable for use within the present invention include hydrophobic domains that are "hidden" at physiological pH, but are exposed in the low pH environment of the target cell endosome. Upon pH-induced unfolding and exposure of the hydrophobic domain, the moiety binds to lipid bilayers and effects translocation of the covalently linked polypeptide into the cell cytoplasm. Such internalizing peptides may be modeled after sequences identified in, e.g., *Pseudomonas* exotoxin A, clathrin, or Diphtheria toxin.

Pore-forming proteins or peptides may also serve as internalizing peptides herein. Pore-forming proteins or peptides may be obtained or derived from, for example, C9 complement protein, cytolytic T-cell molecules or NK-cell molecules. These moieties are capable of forming ring-like structures in membranes, thereby allowing transport of attached polypeptide through the membrane and into the cell interior.

Mere membrane intercalation of an internalizing peptide may be sufficient for translocation of the immune modulator or peptidomimetic, across cell membranes. However, translocation may be improved by attaching to the internalizing peptide a substrate for intracellular enzymes (i.e., an "accessory peptide"). It is preferred that an accessory peptide be attached to a portion(s) of the internalizing peptide that protrudes through the cell membrane to the cytoplasmic face. The accessory peptide may be advantageously attached to one terminus of a translocating/internalizing moiety or anchoring peptide. An accessory moiety of the present invention may contain one or more amino acid residues. In one embodiment, an accessory moiety may provide a substrate for cellular phosphorylation (for instance, the accessory peptide may contain a tyrosine residue).

An exemplary accessory moiety in this regard would be a peptide substrate for N-myristoyl transferase (Eubanks et al., in: Peptides, Chemistry and Biology, Garland Marshall (ed.), ESCOM, Leiden, 1988, pp. 566-69). In this construct, an internalizing peptide would be attached to the C-terminus of the accessory peptide, since the N-terminal glycine is critical for the accessory moiety's activity. This hybrid peptide, upon attachment to an E2 peptide or peptidomimetic at its C-terminus, is N-myristylated and further anchored to the target cell membrane, e.g., it serves to increase the local concentration of the immune modulator at the cell membrane.

To further illustrate use of an accessory peptide, a phosphorylatable accessory peptide is first covalently attached to the C-terminus of an internalizing peptide and then incorporated into a fusion protein with an immune modulator or peptidomimetic. The peptide component of the fusion protein intercalates into the target cell plasma membrane and, as a result, the accessory peptide is translocated across the membrane and protrudes into the cytoplasm of the target cell. On the cytoplasmic side of the plasma membrane, the accessory peptide is phosphorylated by cellular kinases at neutral pH. Once phosphorylated, the accessory peptide acts to irreversibly anchor the fusion protein into the membrane. Localization to the cell surface membrane can enhance the translocation of the polypeptide into the cell cytoplasm.

Suitable accessory peptides include peptides that are kinase substrates, peptides that possess a single positive charge, and peptides that contain sequences which are glycosylated by membrane-bound glycotransferases.

Internalizing and accessory peptides can each, independently, be added to the immune modulator or peptidomimetic by either chemical cross-linking or in the form of a fusion protein. In the instance of fusion proteins, unstructured polypeptide linkers can be included between each of the peptide moieties.

In general, the internalization peptide will be sufficient to also direct export of the polypeptide. However, where an accessory peptide is provided, it may be necessary to include a secretion signal sequence to direct export of the fusion protein from its host cell. In preferred embodiments, the secretion signal sequence is located at the extreme N-terminus, and is (optionally) flanked by a proteolytic site between the secretion signal and the rest of the fusion protein. In certain instances, it may also be desirable to include a nuclear localization signal.

In the generation of fusion polypeptides including the subject immune modulators, it may be necessary to include unstructured linkers in order to ensure proper folding of the various peptide domains. Many synthetic and natural linkers are known in the art and can be adapted for use in the present invention, including the (Gly3 Ser)4 linker.

(e) Immune Modulator Mimetics

In other embodiments, the subject compositions are peptidomimetics of the immune modulators. Peptidomimetics are compounds based on, or derived from, peptides and proteins. The immune modulator peptidomimetics of the present invention typically can be obtained by structural modification of a known immune modulator sequences using unnatural amino acids, conformational restraints, isosteric replacement, and the like. The subject peptidomimetics constitute the continum of structural space between peptides and non-peptide synthetic structures; immune modulator peptidomimetics may be useful, therefore, in delineating pharmacophores and in helping to translate peptides into nonpeptide compounds with the activity of the parent immune modulators.

Moreover, as is apparent from the present disclosure, mimetopes of the subject immune modulators can be provided. Such peptidomimetics can have such attributes as being non-hydrolyzable (e.g., increased stability against proteases or other physiological conditions which degrade the corresponding peptide), increased specificity and/or potency, and increased cell permeability for intracellular localization of the peptidomimetic. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988, p 123), C-7 mimics (Huffman et al. in Peptides: Chemistry and Biology, G. R. Marshall ed., ESCOM Publisher: Leiden, Netherlands, 1988, p. 105), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), (3-aminoalcohols (Gordon et al. (1985) Biochem Biophys Res Commun 126:419; and Dann et al. (1986) Biochem Biophys Res Commun 134:71), diaminoketones (Natarajan et al. (1984) Biochem Biophys Res Commun 124:141), and methyleneamino-modified (Roark et al. in Peptides: Chemistry and Biology, G. R. Marshall ed., ESCOM Publisher: Leiden, Netherlands, 1988, p 134). Also, see generally, Session III: Analytic and synthetic methods, in in Peptides: Chemistry and Biology, G. R. Marshall ed., ESCOM Publisher: Leiden, Netherlands, 1988)

In addition to a variety of side chain replacements which can be carried out to generate the immune modulator peptidomimetics, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

Moreover, other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds for compounds capable of binding to the immune modulator. A mimetope can also be obtained, for example, from libraries of natural and synthetic compounds, in particular, chemical or combinatorial libraries (i.e., libraries of compounds that differ in sequence or size but that have the same building blocks). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling, the predicted mimetope structures can then be produced by, for example, chemical synthesis, recombinant DNA technology, or by isolating a mimetope from a natural source (e.g., plants, animals, bacteria and fungi).

An immune modulator of the invention may be synthesized by conventional techniques. For example, the peptides or chimeric proteins may be synthesized by chemical synthesis using solid phase peptide synthesis. These methods employ either solid or solution phase synthesis methods (see for example, J. M. Stewart, and J. D. Young, Solid Phase Peptide Synthesis, 2nd Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis.) By way of example, a RLP or chimeric protein may be synthesized using 9-fluorenyl methoxycarbonyl (Fmoc) solid phase chemistry with direct incorporation of phosphothreonine as the N-fluorenylmethoxy-carbonyl-O-benzyl-L-phosphothreonine derivative.

N-terminal or C-terminal fusion proteins comprising an immune modulator or chimeric protein of the invention conjugated with other molecules may be prepared by fusing, through recombinant techniques, the N-terminal or C-terminal of the immune modulator or chimeric protein, and the sequence of a selected protein or selectable marker with a desired biological function. The resultant fusion proteins contain the immune modulator or chimeric protein fused to the selected protein or marker protein as described herein. Examples of proteins which may be used to prepare fusion proteins include immunoglobulins, glutathione-S-transferase (GST), hemagglutinin (HA), and truncated myc.

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Nucleic Acids

In one embodiment, the invention includes an isolated nucleic acid comprising a nucleotide sequence encoding an immune modulator (e.g., encoding immunomodulatory cytokines or IL-12).

The nucleotide sequence encoding an immune modulator can alternatively comprise sequence variations with respect to an original nucleotide sequence, for example, substitutions, insertions and/or deletions of one or more nucleotides, with the condition that the resulting polynucleotide encodes a polypeptide according to the invention. Therefore, the scope of the present invention includes nucleotide sequences that are substantially homologous to nucleotide sequences encoding immune modulators (e.g., encoding immunomodulatory cytokines or IL-12).

In the sense used in this description, a nucleotide sequence is "substantially homologous" to any of the nucleotide sequences describe herein when its nucleotide sequence has a degree of identity with respect to the nucleotide sequence of at least 60%, advantageously of at least 70%, preferably of at least 85%, and more preferably of at least 95%. A nucleotide sequence that is substantially homologous to a nucleotide sequence encoding an immune modulator can typically be isolated from a producer organism of the polypeptide of the invention based on the information contained in the nucleotide sequence by means of introducing conservative or non-conservative substitutions, for example. Other examples of possible modifications include the insertion of one or more nucleotides in the sequence, the addition of one or more nucleotides in any of the ends of the sequence, or the deletion of one or more nucleotides in any end or inside the sequence. The degree of identity between two polynucleotides is determined using computer algorithms and methods that are widely known for the persons skilled in the art. For example, the identity between two amino acid sequences can be determined by using the BLASTN algorithm [BLAST Manual, Altschul, S., et al., NCBI NLM NIH Bethesda, Md. 20894, Altschul, S., et al., J. Mol. Biol. 215: 403-410 (1990)].

In another aspect, the invention relates to a construct, comprising a nucleotide sequence encoding an immune modulator, or derivative thereof. In a particular embodiment, the construct is operatively bound to transcription, and optionally translation, control elements. The construct can incorporate an operatively bound regulatory sequence of the expression of the nucleotide sequence of the invention, thus forming an expression cassette.

A nucleic acid molecule encoding an immune modulator or chimeric protein may be prepared using recombinant DNA methods. Accordingly, nucleic acid molecules which encode an immune modulator or chimeric protein may be incorporated in a known manner into an appropriate expression vector which ensures good expression of the immune modulator or chimeric protein.

Therefore, in another aspect, the invention relates to a vector, comprising a nucleotide sequence encoding an immune modulator of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

Vectors suitable for the insertion of the polynucleotides are vectors derived from expression vectors in prokaryotes such as pUC18, pUC19, Bluescript and the derivatives thereof, mp18, mp19, pBR322, pMB9, ColEl, pCR1, RP4, phages and "shuttle" vectors such as pSA3 and pAT28, expression vectors in yeasts such as vectors of the type of 2 micron plasmids, integration plasmids, YEP vectors, centromere plasmids and the like, expression vectors in insect cells such as vectors of the pAC series and of the pVL, expression vectors in plants such as pIBI, pEarleyGate, pAVA, pCAMBIA, pGSA, pGWB, pMDC, pMY, pORE series and the like, and expression vectors in eukaryotic cells based on viral vectors (adenoviruses, viruses associated to adenoviruses such as retroviruses and, particularly, lentiviruses) as well as non-viral vectors such as pSilencer 4.1-CMV (Ambion), pcDNA3, pcDNA3.1/hyg, pHMCV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and PKSV-10, pBPV-1, pML2d and pTDT1.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

An isolated nucleic acid encoding an immune modulator of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method.

In certain embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter, leader and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence to which it is operatively linked when such expression is desired, or turning off the expression when expression is not desired. Examples of inducible promoters include, but are not limited to a metallothionein promoter, a glucocorticoid promoter, a progesterone promoter, and a tetracycline promoter.

Enhancer sequences found on a vector also regulate expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of the protein reporter, protein reporter fragment, or protein reporter mutant, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Chol") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots).

Delivery Vehicles

In one embodiment, the present invention provides a delivery vehicle comprising a protein reporter or a nucleic acid molecule encoding a protein reporter. Exemplary delivery vehicles include, but are not limited to, microspheres, microparticles, nanoparticles, polymersomes, liposomes, and micelles. For example, in certain embodiments, the delivery vehicle is loaded with an immune modulator or a nucleic acid molecule encoding an immune modulator of the invention. In certain embodiments, the delivery vehicle provides for controlled release, delayed release, or continual release of its loaded cargo. In certain embodiments, the delivery vehicle comprises a targeting moiety that targets the delivery vehicle to a target site. Exemplary microparticles and nanoparticles that can be used for delivery of the immune modulator of the invention include, but are not limited to, microparticles and nanoparticles as described in US Patent Publication No.: US 2017/0273909A1, the contents of which are incorporated herein in their entirety.

In one embodiment, the delivery vehicle is a scaffold or substrate composition comprising an immune modulator or a nucleic acid molecule encoding an immune modulator of the invention. The scaffold of the invention may be of any type known in the art. Non-limiting examples of such a scaffold include a hydrogel, electrospun scaffold, foam, mesh, sheet, patch, and sponge.

Formulations

The immune modulators described herein can be administered at therapeutically effective doses. Therapeutically effective doses can be determined by one of ordinary skill in the art based on the type of immune modulator administered. Dosage, routes of administration, and administration schedules described in the art can be used. Representative doses are available in the Merck Manual Professional Edition (see the internet at merckmanuals.com/professional).

Further, doses of immune modulators administered to animals can be converted to equivalent doses for humans based on the body surface area (BSA) (represented in $mg/m^2$) normalization method (see, e.g., Reagan-Shaw, S. et al., "Dose translation from animal to human studies revisited," FASEB J. 22, 659-661 (2007); and "Guidance for Industry—Estimating the Maximum Safe Starting Dose in Initial Clinical Trials for Therapeutics in Adult Healthy Volunteers," U.S. Department of Health and Human Services, Food and Drug Administration, Center for Drug Evaluation and Research (CDER), July 2005, Pharmacology and Toxicology; which are incorporated by reference herein). For example, the human equivalent dose (HED) based on BSA can be calculated by the following formula I:

HED=animal dose in mg/kg×(animal weight in kg/human weight in kg)0.33

Alternatively, the HED can be determined by the following formula II:

HED (mg/kg)=animal dose (mg/kg)×(animal $Km$/human $Km$)

In some embodiments, the immune modulators described herein are administered in therapeutically effective amounts for periods of time effective to treat a cancer or tumor. The effective amount of the immune modulators described herein can be determined by one of ordinary skill in the art and includes dosage amounts for a mammal of from about 0.5 to about 200 mg/kg, about 0.5 to about 150 mg/kg, about 0.5 to 100 mg/kg, about 0.5 to about 75 mg/kg, about 0.5 to about 50 mg/kg, about 0.01 to about 50 mg/kg, about 0.05 to about 25 mg/kg, about 0.1 to about 25 mg/kg, about 0.5 to about 25 mg/kg, about 1 to about 20 mg/kg, about 1 to about 10 mg/kg, about 20 mg/kg of body weight, about 10 mg/kg, about 5 mg/kg, about 2.5 mg/kg, about 1.0 mg/kg, or about 0.5 mg/kg of body weight of the immune modulator, or any range derivable therein. In some embodiments, the dosage amounts of the immune modulators are from about 0.01 mg/kg to about 10 mg/kg of body weight. In some embodiments, the dosage amount of the immune modulator is from about 0.01 mg/kg to about 5 mg/kg, or from about 0.01 mg/kg to about 2.5 mg/kg of body weight. The compositions described herein can be administered in a single dose or in the form of individual divided doses, such as from 1 to 4 times per day, or once every 2 days, 3 days, 4 days, 5 days, 6 days, weekly, or monthly. The compositions described herein can also be administered for various treatment cycles, such as 2, 3, 4, 5, 6, 7, 8, 9, 10 treatment cycles. The treatment cycles can be different lengths of time depending on the cancer to be treated, for example, 1, 2, 3, 4, 5, 6, 7, 8, 9, or 10 week treatment cycles. In addition, the effective amount of an immune modulator described herein can be determined during pre-clinical trials and clinical trials by methods known to physicians and clinicians.

Alternatively, administration of a specific amount of may be given which is not based upon the weight of the patient such as an amount in the range of 1 μg-100 μg, 1 mg-100 mg, or 1 gm-100 gm. For example, site specific administration may be to body compartment or cavity such as CT-guided percutaneous intratumoral injection of an effective amount of an immune modulator of the invention. In one embodiment, site specific administration of an effective amount of an immune modulator of the invention is performed through endoscopic ultrasound (EUS) guided delivery. However, the method of delivery is not limited to the above methods, and includes the delivery of at least one or more treatment element to a target site with the aid of a device for example including but not limited to guiding catheter, catheter, endoscope, trocar, introducer, endoscope working channel, endoscope with ultrasound probe, sheath introducer, sleeve, stepper, port, or the like as is known in the art.

The immune modulator of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle. Additional pharmaceutical methods may be employed to control the duration of action. Controlled release preparations may be achieved through the use of polymers to complex or absorb the compounds. Another possible method to control the duration of action by controlled release preparations is to incorporate the compounds of the present invention into particles of a polymeric material such as polyesters, polyamino acids, hydrogels, poly(lacticacid) or ethylene vinylacetate copolymers. Alternatively, instead of incorporating these agents into polymeric particles, it is possible to entrap these materials in microcapsules prepared, for example, by interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions. Exemplary microparticles and nanoparticles that can be used to encapsulate in immune modulator of the invention include, but are not limited to, microparticles and nanoparticles as described in US Patent Publication No.: US 2017/0273909A1, the contents of which are incorporated herein in their entirety. Therefore, in one embodiment, the immune modulatory agent of the invention is encapsulated in a crystalline or semi-crystalline matrix which confers enhanced stability to the agent.

The microparticles of this invention may have a size range from about 1 to 250 microns diameter, 10 to 200 microns diameter, 10 to 130 microns diameter, or about 10 to 90 microns diameter. The amount of immune modulator present in the formulation depends on the desired daily release dosage and thus on the biodegradation rate of the encapsulating matrix. The exact amount of immune modulator may be ascertained by bioavailability trials.

The treatment may be given in a single dose schedule, or as a multiple dose schedule in which a primary course of treatment may be with 1-100 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

Sustained Release Formulations

The immune modulator of the invention may be formulated for sustained release. A sustained release of an immune modulator is a release which results in measurable serum levels of the immune modulator over a period longer than that obtained following direct administration of the immune modulator. In one embodiment, a sustained release is a release of the immune modulator for a period of about 1 day, about 2 days, about 3 days, about 4 days, about 5 days, about 6 days, about 1 week, about 2 weeks, about 3 weeks, about 4 weeks, about 1 month, about 2 months or more than 2 months.

A sustained release of an immune modulator from a polymeric matrix can be continuous or non-continuous release with relatively constant or varying rates of release. The continuity of immune modulator released and level of immune modulator released can be established by using, inter alia, one or more types of polymer compositions, immune modulator loadings, and/or selection of excipients to produce the desired effect.

Polymers suitable to form a polymeric matrix of the sustained release composition of this invention are biocompatible polymers which can be either a biodegradable or non-biodegradable polymer, or blends or copolymers thereof. A polymer, or polymeric matrix, is biocompatible if the polymer, and any degradation products of the polymer, are non-toxic to the recipient and also present no significant deleterious or untoward effects on the recipient's body, such as an immunological reaction at the injection site. Suitable biocompatible, biodegradable polymers include, for example, poly(lactides), poly(glycolides), poly(lactide-co-glycolides), poly(lactic acid)s, poly(glycolic acid)s, poly (lactic acid-co-glycolic acid)s, polycaprolactone, polycarbonates, polyesteramides, polyanhydrides, poly(amino acids), polyorthoesters, polycyanoacrylates, poly (p-dioxanone), poly(alkylene oxalate)s, biodegradable polyurethanes, blends and copolymers thereof. Biocompatible, non-biodegradable polymers suitable for the modulated release composition of this invention include non-biodegradable polymers selected from the group consisting of polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

In one embodiment, the terminal functionalities of a polymer of the polymeric matrix can be modified. For example, polyesters can be blocked, unblocked or a blend of blocked and unblocked polymers. A blocked polymer is as classically defined in the art, specifically having blocked carboxyl end groups. Generally, the blocking group is derived from the initiator of the polymerization and is typically an alkyl group. An unblocked polymer is as classically defined in the art, specifically having free carboxyl end groups.

A sustained release composition of this invention can be formed into many shapes such as a film, a pellet, a cylinder, a disc or a microparticle. Exemplary sustained release microparticles and nanoparticles that can be used to encapsulate in immune modulator of the invention include, but are not limited to, microparticles and nanoparticles as described in US Patent Publication No.: US 2017/0273909A1.

The amount of the immune modulator, which is contained in a sustained release formulation is a therapeutically or prophylactically effective amount, which can be determined by a person of ordinary skill in the art taking into consideration factors such as body weight, condition to be treated, type of polymer used, and release rate from the matrix. The sustained release composition can also contain other excipients, such as stabilizers, encapsulating agents, dyes, bulking agents, and combinations thereof. Stabilizers are added to maintain the potency of the sustained release composition over the duration of release. Suitable stabilizers include, for example, carbohydrates, amino acids, fatty acids and surfactants and are known to those skilled in the art. Bulking agents typically comprise inert materials. Suitable bulking agents are known to those skilled in the art.

Combination Therapy

The combination of an immune modulator and radiation therapy of the invention can be used in combination with another therapeutic treatment or agent to treat cancer. For example, the combination of an immune modulator and radiation therapy of the invention may be administered alone, or in combination with one or more therapeutically effective agents or treatments. The other therapeutically effective agent may be incorporated into the same composition as the immune modulator of the invention, or may be administered as a separate composition. The other therapeutically agent or treatment may be administered prior to, during and/or after the administration of the combination of immune modulator and radiation therapy of the invention.

In certain embodiments, the combination of an immune modulator and radiation therapy of the invention is co-administered with one or more other therapeutic agents or treatments. In other embodiments, the combination of an immune modulator and radiation therapy of the invention is administered independently from the administration of one or more other therapeutic agents or treatments. For example, the combination of an immune modulator and radiation therapy of the invention is administered first, followed by the administration of one or more other therapeutic agents or treatments. Alternatively, one or more other therapeutic agents are administered first, followed by the administration of the combination of an immune modulator and radiation therapy of the invention. As another example, a treatment (e.g., a surgery etc.) is carried out first, followed by the administration of the combination of an immune modulator and radiation therapy of the invention.

Other therapeutically effective agents/treatments include surgery, anti-neoplastics (including chemotherapeutic agents and radiation), anti-angiogenesis agents, antibodies to other targets, small molecules, photodynamic therapy, immunotherapy, immunity enhancing therapy, cytotoxic agents, cytokines, chemokines, growth inhibitory agents, anti-hormonal agents, kinase inhibitors, cardioprotectants, immunostimulatory agents, immunosuppressive agents, and agents that promote proliferation of hematological cells.

In one embodiment, the "another therapeutic agent," as used herein, are second, distinct therapeutic agents or anti-cancer agents, i.e., therapeutic agents or anti-cancer agents "other than" the combination of radiation and immune modulators of the invention. Any additional therapeutic agent may be used in the combination therapies of the present invention. One or more additional therapeutic agents may be selected with a view to achieving additive, greater than additive and potentially synergistic effects, according to the following guidance.

To practice combined anti-tumor therapy, one would administer to an animal or patient a combination of immune modulator and radiation therapy, of the invention in combination with another distinct anti-cancer agent in a manner effective to result in their combined anti-tumor actions within the animal or patient. The agents would therefore be provided in amounts effective and for periods of time effective to result in their combined, or concurrent, presence within the tumor or tumor vasculature and their combined actions in the tumor environment. To achieve this goal, the immune modulator and one or more additional, distinct anti-cancer agents may be administered to the animal substantially simultaneously, either in a single composition, or as two distinct compositions using different administration routes.

In one embodiment, administration of an immune modulator of the invention may precede, or follow, administration of one or more additional anti-cancer agent by an interval ranging from seconds, to minutes, to hours, to days, to weeks.

The one or more additional therapeutic agents for separately timed combination therapies may be selected based upon certain criteria, including those discussed elsewhere herein. However, the selection of one or more distinct anti-cancer agents for prior or subsequent administration does not preclude their use in substantially simultaneous administration if desired.

Additional, distinct anti-cancer agents selected for administration "prior to" or "subsequent to" the primary therapeutic agents of the present invention, and designed to achieve increased and potentially synergistic effects, include agents that benefit from the effects of the primary therapeutic agent. Accordingly, effective second, distinct anti-cancer agents for subsequent administration include anti-angiogenic agents, which inhibit metastasis; agents targeting necrotic tumor cells, such as antibodies specific for intracellular binding partner molecules that become accessible from malignant cells in vivo (U.S. Pat. Nos. 5,019,368, 4,861,581 and 5,882,626, each specifically incorporated herein by reference); chemotherapeutic agents; and anti-tumor cell immunoconjugates, which attack any tumor cells.

The immune modulator, of the invention can also be administered in combination with one or more additional cancer immunotherapy. The cancer immunotherapy can be one designed to elicit a humoral immune response against the subject's cancer cells, or a cell-mediated immune response against the subject's cancer cells, or a combination of a humoral response and a cell-mediated response against the subject's cancer cells. Non-limiting examples of cancer immunotherapy useful in combination with the combination of radiation therapy and immune modulator of the invention include a cancer vaccine, a DNA cancer vaccine, adoptive cellular therapy, adoptive immunotherapy, CAR T-cell therapy, antibodies, immunity enhancing compounds, cytokines, interleukins (e.g., IL-2, etc.), interferons (IFN-α, etc.), and checkpoint inhibitors (e.g., PD-1 inhibitor, PDL-1 inhibitor, CTLA-4 inhibitor, etc.).

In some situations, it may be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administrations. This would be advantageous in circumstances where one treatment was intended to substantially destroy the tumor, such as the primary therapeutic agent of the present invention, and another treatment was intended to prevent metastasis or tumor re-growth, such as the administration of an anti-angiogenic agent. Anti-angiogenics should be administered at a careful time after surgery, however, to allow effective wound healing. Anti-angiogenic agents may then be administered for the lifetime of the patient.

It is also envisioned that more than one administration of either the immune modulator of the invention or radiation therapy will be utilized. The immune modulator of the invention and the radiation therapy may be administered interchangeably, on alternate days or weeks; or a sequence of radiation therapy may be given, preceded or followed by one or more administration of the immune modulator. In any event, to achieve a combined therapy, all that is required is to deliver both an immune modulator and radiation therapy in a combined amount effective to exert an anti-tumor effect, irrespective of the times for administration.

Chemotherapeutic drugs can be used in combination with the combination of the immune modulator and radiation therapy of the invention. Chemotherapeutic drugs can kill proliferating tumor cells, enhancing the necrotic areas created by the overall treatment.

One aspect of the invention provides a method of treating pancreatic cancer using the combination of radiation therapy and immune modulator of the invention. The skilled artisan will understand that treating cancer in a patient includes, by way of non-limiting examples, killing and destroying a cancer cell, as well as reducing the proliferation of or cell division rate of a cancer cell. The skilled artisan will also understand that a cancer cell can be, by way of non-limiting examples, a primary cancer cell, a cancer stem cell, or a metastatic cancer cell.

In one embodiment, the invention provides a method to treat cancer comprising treating the subject prior to, concurrently with, or subsequently to the administration of the immune modulator of the invention, with a radiation therapy for the cancer. In various embodiments, one or more additional therapies for the cancer can be administered to the subject prior to, concurrently with, or subsequently to at least one of administration of an immune modulator of the invention and administration of a radiation therapy.

Examples of additional therapies that can be administered in addition to the combination of the immune modulator of the invention and radiation therapy include, but are not limited to, chemotherapeutic agents, antiproliferative agents, cytotoxic/antineoplastic agents, anti-angiogenic agents, and other anti-cancer agents.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta), retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the disclosed compounds include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; albumin-bound paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; rioprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; j asplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyna; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromely sin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; imilimumab; mirtazapine; BrUOG 278; BrUOG 292; RAD0001; CT-011; folfirinox; tipifarnib; R115777; LDE225; calcitriol; AZD6244; AMG 655; AMG 479; BKM120; mFOLFOX6; NC-6004; cetuximab; IM-C225; LGX818; MEK162; BBI608; MEDI4736; vemurafenib; ipilimumab; ivolumab; nivolumab; panobinostat; leflunomide; CEP-32496; alemtuzumab; bevacizumab; ofatumumab; panitumumab; pembrolizumab; rituximab; trastuzumab; STAT3 inhibitors (e.g., STA-21, LLL-3, LLL12, XZH-5, S31-201, SF-1066, SF-1087, STX-0119, cryptotanshinone, curcumin, diferuloylmethane, FLLL11, FLLL12, FLLL32, FLLL62, C3, C30, C188, C188-9, LYS, OPB-31121, pyrimethamine, OPB-51602, AZD9150, etc.); hypoxia inducing factor 1 (HIF-1) inhibitors (e.g., LW6, digoxin, laurenditerpenol, PX-478, RX-0047, vitexin, KC7F2, YC-1, etc.) and zinostatin stimalamer.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Stereotactic Body Radiation and Interleukin 12 Combination Therapy Eradicates Pancreatic Tumors by Composite Repolarization of the Tumor Microenvironment In this study, sustained delivery of adjuvant IL12 is demonstrated to enhance the antitumor potency of SBRT in LAPC. The data presented herein demonstrate that the addition of intratumoral delivery of IL12 encapsulated in sustained-release microspheres (IL12 MS) to SBRT demonstrated robust antitumor activity and resulted in the reduction of tumors in preclinical orthotopic models of PC. The combination immunotherapy resulted in synergistic production of the proinflammatory cytokine interferon gamma (IFNγ), and the therapeutic efficacy was dependent upon this induction. Subsequent analyses demonstrated that IFNγ expression was necessary for the immunogenic reprogramming of T regulatory and myeloid suppressor cells. Furthermore, increased CD8+ T cell to suppressor cell ratios coincided with significantly increased CD8+ T cell activation. Beyond the scope of local control, SBRT/IL12 MS combination also conferred systemic tumor immunity which provides rationale follow-up studies in advanced metastatic disease.

The materials and methods used in this example are now described.

Orthotopic Tumor Implantation

Mice were anesthetized using an isoflurane anesthetic vaporizer (Scivena Scientific) and a 10-mm laparotomy incision was made to expose the spleen and pancreas. Cell lines were detached with 0.25% trypsin/EDTA (Gibco) and resuspended in a 1:1 PBS:Matrigel (BD Biosciences) solution. Fifty-thousand cells (100 □) were injected into the pancreatic tail and two 4-mm titanium fiducial markers (Horizon) to assist in SBRT targeting were implanted adjacent to the tumor bubble. For 1 minute immediately following tumor cell injection, a cotton swab was placed over the injection site to prevent peritoneal leakage. IVIS bioluminescent imaging verified successful implantations with no peritoneal studding, and provided baseline measurements for standardizing pre-treatment groups.

Radiation

All radiation was delivered using the Small Animal Radiation Research Platform (SARRP, XStrahl) with a 5-mm collimator. Mice were anaesthetized with vaporized isoflurane during all radiation treatments. Tumor-bearing mice that underwent conventional radiotherapy (ConRT) were dosed with 2 Gy in 15 fractions yielding a biological effective dose (BED) of 36 for tumor tissue and 50 for normal tissue (a/b ratio 10/3 tumor/normal tissue). Stereotactic body radiation therapy (SBRT) was administered to tumor-bearing mice following a schedule of 6 Gy radiation in 4 fractions on days 6-9 post-implantation, yielding a BED of 38.4 for tumor tissue and 72 for normal tissue. Localized delivery was targeted using previously mentioned titanium fiducial markers; markers were visualized with pre-treatment computed tomography (CT) scans. The dosing isocenter was positioned using a beam angle designed to circumvent major organs. In each case, a dose volume histogram (DVH) was generated to confirm full dose deposition to the tumor and negligible amounts to surrounding organs (e.g. liver).

Bioluminescent Imaging

In vivo tumor growth was measured using the IVIS Spectrum Imaging System (IVIS, PerkinElmer). Mice were anesthetized by vaporized isoflurane and injected subcutaneously with D-luciferin (2.5 mg, Invitrogen) in 100 µl PBS vehicle. While in the right lateral recumbent position, a series of images were taken at 2-minute intervals for 24 minutes and photon emissions were collected. Bioluminescence (p/sec/cm$^2$/sr) was calculated within matching (circular) regions of interest (ROIs) manually placed over tumors. Peak intensity was recorded for each tumor upon two sequential measurements demonstrating signal decay.

Immunohistochemistry

All SBRT-treated specimens were acquired 10-14 days following neoadjuvant intervention. Human PDAC tissue samples were fixed in 10% neutral buffered formalin, processed, and sectioned. For IHC analyses, serial sections were stained overnight at 4° C. with anti-CD8 (C8/144B, 1:100 dilution, Thermo Scientific MS-457-51), and anti-CD68 (KP1, 1:200, Thermo Scientific MS-397-PO) antibodies. A polymer-based system was used for detection (GBI Broad Spectrum Polink 2 Plus (GBI D22), DAB chromogen (GBI CO2-12) incubation). Slides were counterstained with Mayer's hematoxylin. Staining was completely absent in identical tissue sections in which a universal negative control solution was used (Enzo ADI-950-231-0025). Whole tissue sections were digitized at 20× magnification and registered. Regions of interest were defined by a licensed pathologist (blinded) as follows: "margin"—area defined by 500 μm within and outside of a manually drawn line at tumor/stroma interface; "center"—area defined by 1000 μm within the invasive front, mucosal surface, or tissue edge. Areas of tissue loss/artifacts were excluded from analysis. Random forest classification was used to enumerate the number of events, and margin index (ratio of margin:center) was calculated for entire ROIs of each case individually.

Microsphere Injection

Polylactic acid microspheres were created using phase inversion phenomena. Lyophilized microspheres were resuspended in PBS (20 μl per mouse) prior to intratumoral delivery. Twenty-four hours following the final SBRT fraction (day 10), mice were anaesthetized with vaporized isoflurane and a 10-mm laparotomy incision was made to expose pancreas tumors. Empty MS control (2 mg beads) or IL12 MS (2 mg beads containing 0.5 μg recombinant IL12) were injected intratumorally (i.t.) using an 18-guage Hamilton syringe.

TCGA Analysis

Pancreatic adenocarcinoma gene expression datasets (FPKM, upper quartile normalized) from HTSeq workflows were downloaded from The Cancer Genome Atlas (TCGA) data portal. $R^2$-values were computed between datasets using Non-Parametric Spearman correlation. For heatmap representations, data values were normalized to median expressions within each geneset. Each cell represents the average of 3 neighboring values within a dataset.

Luminex Analyte Assay

Following sacrifice, mouse tumors were dissociated with a tissue homogenizer in 100 μl 0.5× Cell Lysis Buffer 2 (R&D Systems, diluted in PBS), containing 1× Halt Protease Inhibitor Cocktail and 1× Halt Phosphatase Inhibitor Cocktail (ThermoFisher Scientific). Tissues were lysed at room temperature for 30 minutes with gentle agitation. Magnetic Luminex Assays were performed using a Mouse Premixed Cytokine/Chemokine Multi-Analyte Kit (R&D Systems). Assay procedures were carried out following manufacturer's instructions. Microplates were run on a Bio-Plex 200 system (Bio-Rad) collecting 50-100 beads per target with less than 20% aggregate. Pierce BCA Protein Assays (ThermoFisher Scientific) were performed on remaining lysates following manufacturer's instructions. Total protein concentrations for each sample were used for analyte normalization into pg/mg protein values.

Flow Cytometry

Following sacrifice, mouse tumors were mechanically dissociated followed by digestion with 30% collagenase (30 minutes, 37° C., Sigma-Aldrich). Homogenates were then passed through 40 μm filters and cells were resuspended in PAB (1 L PBS, 1 g sodium azide, 10 g BSA) at approximately $1 \times 10^6$ cells/reaction. The following conjugated antibodies were used for staining: PerCP/Cy5.5 anti-mouse CD45 (30-F11, BD Biosciences), efluor anti-mouse Cd8 (53-6.7, eBioscience), APC/Cy7 anti-mouse CD4 (GK1.5, BD Pharmingen), PE/CF594 anti-mouse NK1.1 (PK136, BD Horizon), PE/Cy7 anti-mouse CD279 (RMP1-30, BioLegend), efluor anti-mouse CD11b (M1/70, Invitrogen), APC/Cy7 anti-mouse Ly-6C (AL-21, BD Pharmingen), Brilliant Violet 605 anti-mouse Ly-6G (1A8, BD Horizon), APC anti-mouse F480 (BM8, eBioscience), PE anti-mouse IA/IE (M5/114.15.2, BD Pharmingen), APC anti-mouse/rat FoxP3 (FJK-16s, eBioscience), and PE anti-mouse IFN-γ (XMG1.2, BD Biosciences). Cell surface antigens were stained for 30 minutes at 4° C. in the dark. Samples were then washed with PAB and fixed overnight using the FOXP3 fixation/permeabilization kit (eBioscience) following manufacturer's instructions. The following day, cells were washed with FOXP3 Permeabilization Buffer (eBioscience) and stained for intracellular targets for 30 minutes at 4° C. in the dark. FMO controls were utilized for intracellular activation markers. Cells were washed and resuspended in PAB and run on a LSRII Fortessa (BD Biosciences). 50-100,000 events/sample were collected and analyzed using FlowJo software (FlowJo). The same procedure was followed for imaging flow cytometry, and samples were run on an Amnis ImageStream GenX (Luminex Corporation).

RNA-Seq

Following sacrifice, 2 mouse tumors were pooled per treatment group. Tissues were mechanically dissociated followed by digestion with 30% collagenase (30 minutes, 37° C., Sigma-Aldrich). Homogenates were passed through 40 μm filters and cells were resuspended in PAB (1 L PBS, 1 g sodium azide, 10 g BSA). Between $2 \times 10^6$ and $4 \times 10^6$ cells from each treatment group were stained for cell surface antigens for 30 minutes at 4° C. in the dark. CD8+ T cell, IM, and TAM populations were sorted on a FACSAriaII cell sorter (BD Biosciences) using a 100 μm nozzle. Cells were immediately lysed in Buffer RLT (containing β-mercaptoethanol), homogenized with QIAShredder spin columns, and RNA was purified using the RNeasy Micro Kit (Qiagen) following manufacturer's instructions. RNA sequencing and analysis was performed. RNA quality was assessed using an Agilent Bioanalyzer (Agilent), and all samples analyzed demonstrated RNA integrity values >5. CDNA libraries were constructed using the TruSeq RNA Sample Preparation Kit V2 (Illumina) following manufacturer's instructions, and sequencing was performed on an Illumina high-throughput HiSeq™ 2500 platform (Illumina). Genes differentially expressed in treatment groups relative to unirradiated+ empty MS controls were analyzed using Ingenuity Pathway Analysis (IPA) software (Qiagen).

Myeloid Transplant

Following sacrifice on day 11, KCKO-luc tumors were harvested and prepared for flow sorting following the procedure used for RNA-seq analysis. IM, and TAM populations were sorted on a FACS Aria II cell sorter (BD Biosciences) using a 100 μm nozzle into DMEM/F-12 supplemented with 10% fetal bovine serum. Sorted IMs and TAMs were counted and pooled with freshly cultured KCKO-luc cells in a 1:1:2 ratio, respectively. Cell mixtures were resuspended in a 1:1 PBS:Matrigel (BD Biosciences) solution, and 100,000 cells (50 μL) were injected into the pancreatic tail of naive mice following the standard orthotopic implantation procedure. No further treatments were administered, and IVIS bioluminescent imaging was used to measure tumor outgrowth.

Antibody Depletion

Following KCKO-luc tumor implantation on day 0, 200 μg depleting antibody (resuspended to 100 μL in PBS) was injected in mice subcutaneously every 3 days between days 5 and 20 (6 doses). The antibodies (Bio X Cell) delivered were rat isotype control (IgG2a, C1.18.4), rat anti-mouse CD8a (IgG2a, 53-6.7), and rat anti-mouse CD4 (IgG2a, GK1.5).

Hemi-Spleen Tumor Implantation

Mice cured of primary KCKO-luc tumors were rechallenged approximately 6 months following initial orthotopic tumor implantation. Vaporized isoflurane was used to anesthetize mice prior to ten-mm laparotomy incision to expose the spleen. Six-mm titanium clips (Horizon) were placed adjacent to the hepatic portal vein, and a hemisecting cut was made between ligations. KCKO-luc cells were detached with 0.25% trypsin/EDTA, resuspended in PBS, and passed through a 40 μm filter to achieve a single cell suspension. The hemi-spleen segment connected to the hepatic portal vein was injected with $5×10^5$ cells (in 100 μL PBS) slowly, over the course of 1 min. Following implantation, a third titanium clip was used to ligate the hepatic portal vein immediately adjacent to the spleen, and the injected splenic segment was resected and distal vasculature was cauterized. For bioluminescent imaging, mice were placed in the supine position.

T Cell Transplants

Mice with no evidence of tumor burden following primary orthotopic implantation and hemi-spleen rechallenge were sacrificed approximately 9 months following initial tumor challenge. Additionally, 5 age-matched tumor-naive mice were also sacrificed for controls. Spleens as well as draining, axillary, inguinal, and iliac lymph nodes were harvested and mechanically dissociated. CD8+ T cells were isolated by negative selection using the EasySep Mouse CD8+ T Cell Isolation Kit (STEMCELL Technologies), following manufacturer's instructions. Approximately $4×10^6$ CD8+ T cells per donor were purified from an input of $5×10^7$ cells per donor. $CD8^+$ T cells were resuspended in 100 mL PBS and delivered to recipient mice via tail vein injection 16 hours prior to KCKO-luc orthotopic tumor implantation (1:1 donor:recipient transferal). IVIS tumor burden measurements were used to classify the transferal of immunological memory (>10-fold decrease in tumor volume), and blinded manual palpation at day 40 was used to confirm full immunological memory (unidentifiable tumor).

Abscopal Studies

In addition to standard KCKO-luc orthotopic implantation on day 0, 50,000 cells (suspended in 100 μL PBS) or $5×10^5$ cells (suspended in 100 μL PBS) were intramuscularly injected into the left hind limb or seeded in the liver using the hemi-spleen technique, respectively. To prevent interference with SBRT targeting, Vicryl suture (Ethicon) was used for spleen and portal vein ligations. Following SBRT treatment of the primary pancreatic tumor, dose volume histograms were generated to confirm full dose deposition into the primary tumor without spillover into the secondary leg or liver tumors. For IVIS imaging, mice were administered 2.5 mg D-luciferin s.c. (in 100 μL PBS), and both primary and secondary tumor ROIs were designated for separate bioluminescent measurements. Digital calipers were used to measure leg tumor diameters in two perpendicular dimensions, and volumes were calculated using the formula: $d1×d2^2×0.52$. Blinded caliper measurements were used to identify tumor-free mice.

Quantification and Statistical Analyses

Prism 7 software (GraphPad) was used for all statistical analyses, and p values of <0.05 were considered significant. Bioluminescent tumor growth curves from ConRT/SBRT comparison and cell depletion studies were compared using nonparametric Mann-Whitney tests. All other tumor growth assays were analyzed at each timepoint using one-way ANOVA (Dunn's multiple comparisons test). For survival analyses, Mantel-Cox tests were used to assess significance. For IHC analyses, independent t tests were used to compare the mean values of untreated to SBRT-treated tumors. Laevene's test was used to evaluate equality of variances. Statistical analysis of multi-timepoint tumor weight and cytokine profiling measurements was performed using two-way ANOVA (Holm-Sidak multiple comparisons test). All flow cytometry gating was done using FlowJo 10 software (FlowJo). One-Way ANOVA statistical analyses were used to assess significance of flow cytometric cell density and geometric mean intensity measurements. Ingenuity Pathway Analysis (IPA) software (Qiagen) was used for all RNA-seq differentially-expressed gene analyses. All diagrammatic figures were created with BioRender.

The results of this example are now described.

SBRT Recruits CD8 T Cells into the Center of Human PDA Tumors and is Superior to conRT To assess the immune response to SBRT in human PDA, immunohistochemistry was performed on tumors resected 10-14 days following neoadjuvant SBRT (5 gray [Gy] 3 5 consecutive days). All tissues analyzed were diagnosed as resectable and treatment-naive prior to SBRT-only intervention. H&E staining was used to demarcate the center and margin of each tumor. Immunohistochemical analysis of unirradiated (UI) tumors illustrated few CD8 T cells in the lesion center, with the greater numbers trapped in the margin (FIGS. 1A, 1B, and 1E). Importantly, SBRT treatment resulted in a greater infiltration of CD8 T cells into central tumor regions (FIGS. 1C, 1D, and 1E) as demonstrated by significantly increased center:margin cellular ratios (FIG. 1F). An assessment of $CD68^+$ myeloid cells demonstrated a uniform distribution of immunosuppressive myeloid populations across the margins and centers of tumors in both unirradiated (FIGS. 1G, 1H, and 1K) and SBRT-treated (FIGS. 1I, 1J, and 1K) groups upon center:margin quantification (FIG. 1L). These clinical data suggest that SBRT results in a uniform dispersal of antitumor CD8 T cells throughout PDA tumors; however, treatment does not eliminate or alter the distribution of immunosuppressive $CD68^+$ cells.

Standard-of-care PC therapies including chemotherapy and conventional radiotherapy are rarely capable of downsizing locally advanced lesions, however, SBRT has been associated with overall survival superior to that of conRT in patients with LAPC (Zhong et al., 2017, Cancer, 123(18): 3486-3493). To compare SBRT and conRT schedules preclinically, an orthotopic mouse model of PC was utilized. A derivative of the KC cell line (P48-Cre; LSL-$Kras^{G12D}$) transformed with luciferase (KCKO-luc) was implanted (day 0) prior to the commencement of radiotherapy on day 6. Radioequivalent doses of SBRT (6 Gy×4 days) and conRT (2 Gy×15 days) were targeted to pancreas tumors using two fiducial metal clips inserted on either side of the tumors during implantation. Measurement of tumor bioluminescence using the in vivo imaging system (IVIS) confirmed greater reductions in tumor burden with SBRT scheduling relative to conventional, reaching significance at day 30 (FIG. 1M). Furthermore, the SBRT-treated group demonstrated the greatest survival benefit, with 2/5 mice becoming long-term survivors (>120 days) (FIG. 1N). These data support clinical observations that SBRT is more efficacious than conRT in reducing PC tumor burden.

Figures 2D, 2E, 2F:
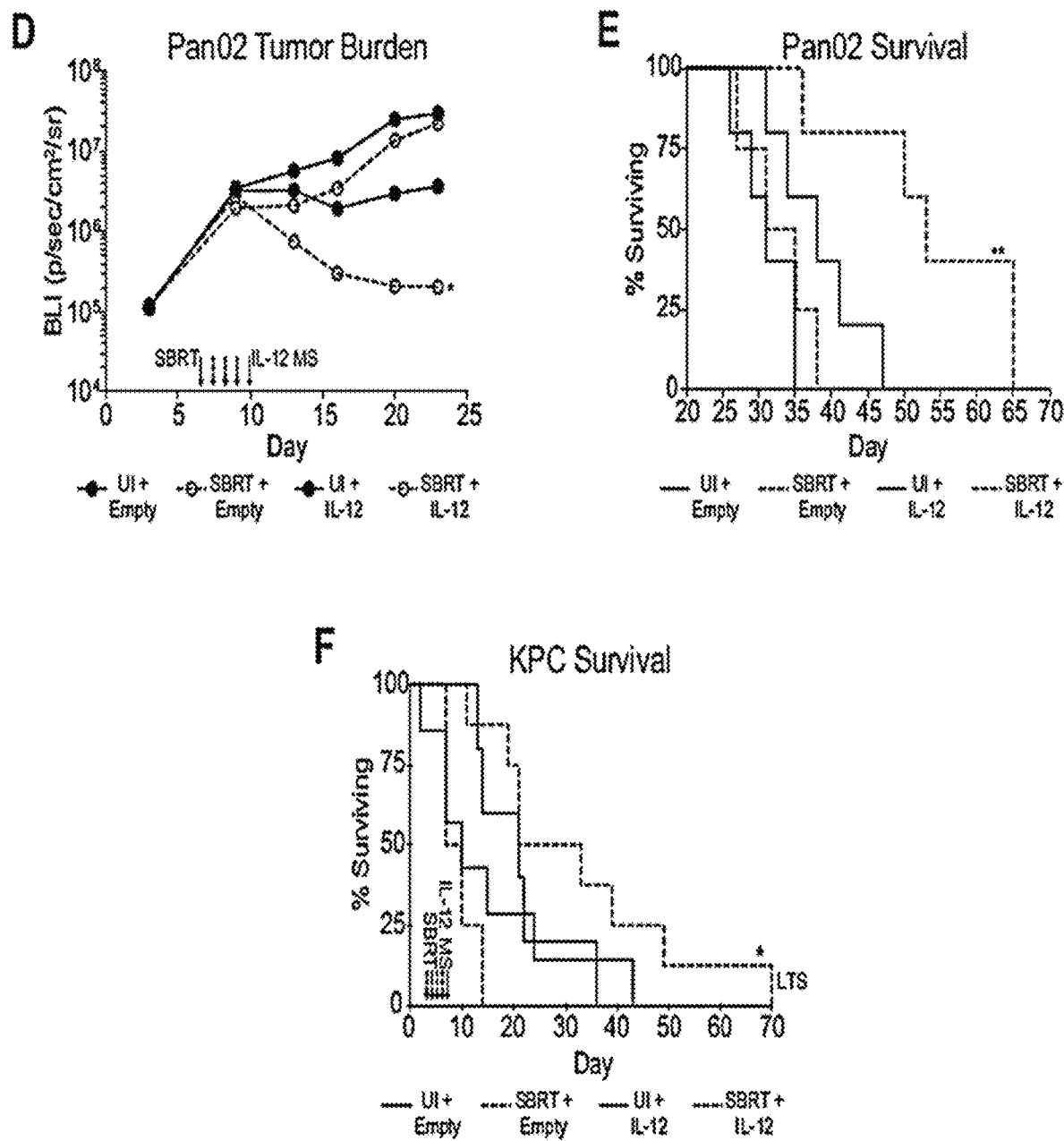
Figures 3A, 3B, 3C, 3D:
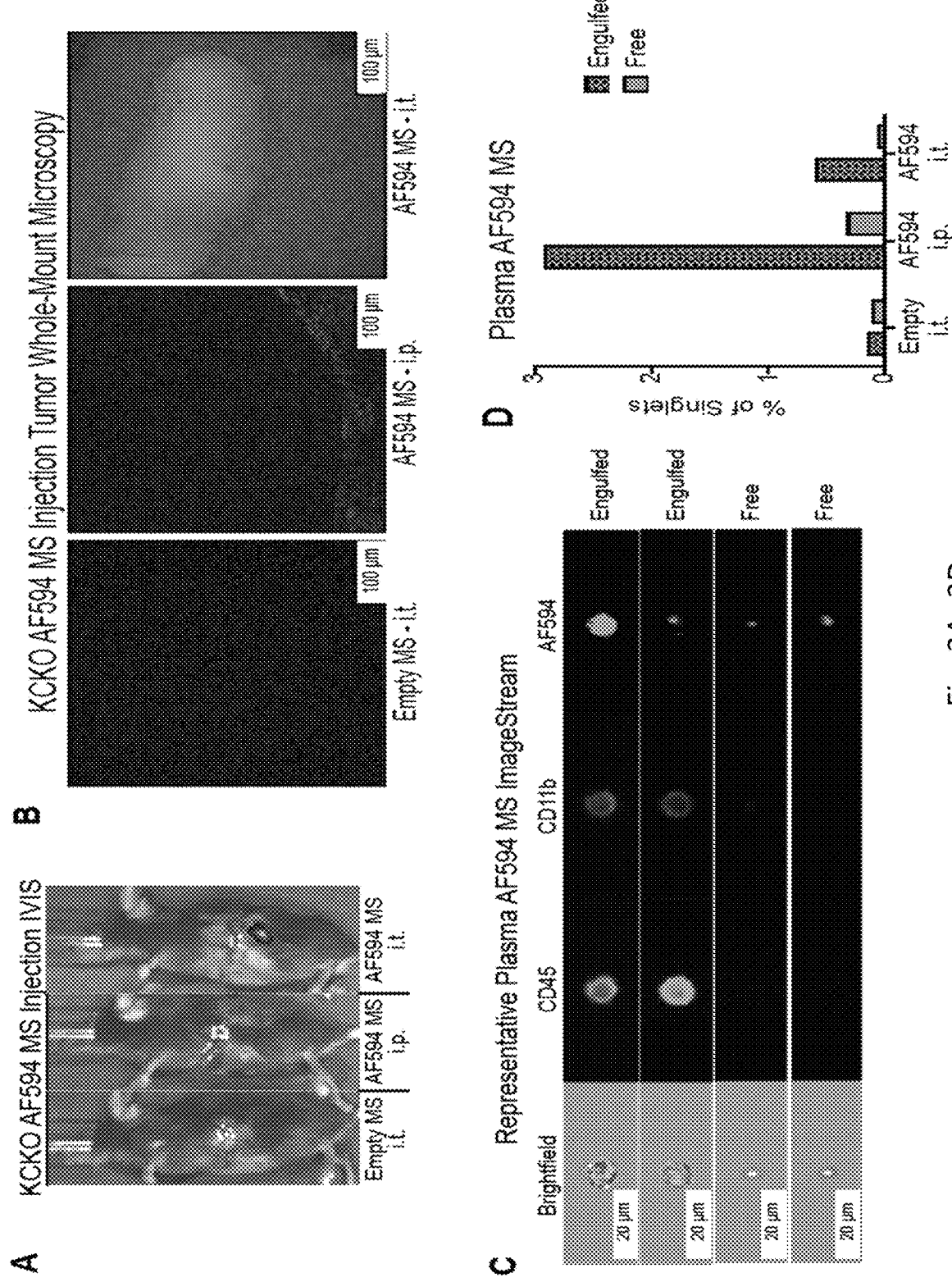
FIG. 3A through FIG. 3D, depicts exemplary data demonstrating an assessment of intratumoral microsphere injection using fluorescently-labeled AF594 MS KCKO cells, which were orthotopically implanted on day 0 (1×10⁵ cells in 50 μL 1:1 PBS/Matrigel). On day 10, Empty MS control (2 mg beads in 20 μL PBS) or fluorescently-labeled AF594 MS (2 mg beads containing 0.5 μg AF594-BSA in 20 μL PBS) were injected either i.t. or i.p. (n=1, representative of one experiment).

Combining SBRT and IL12 MS Therapies Results in Robust and Stable Anti-Tumor Responses Recent clinical investigations of neoadjuvant SBRT in PC have demonstrated moderately effective downstaging, the observation of an immunologically diverse infiltrate following SBRT suggests an avenue for synergy with immunotherapy. To test the combination of SBRT with the pleiotropic proinflammatory cytokine IL12, studies were performed in preclinical mouse models of pancreatic cancer. For increased stability and extended delivery of IL12 within the tumor microenvironment (TME), the cytokine was encapsulated in polylactic acid microspheres (MSs). Orthotopic KCKO-luc tumors were treated with a clinically relevant schedule of SBRT (6 Gy 3 4 days) delivered locally by SARRP. MSs (IL-12 or empty) were intratumorally (i.t.) injected 24 h post-SBRT (FIG. 2A) (Mathiowitz et al., U.S. Pat. No. 6,143,211). Using AF594 fluorescently labeled MS, it was demonstrated that this injection strategy results in intratumoral sequestration of MSs, whereas intraperitoneal (i.p.) injection (used to simulate MS "leakage") led to peritoneal myeloid engulfment and subsequent trafficking into the bloodstream (FIGS. 3A and 3B). Furthermore, free AF594 MSs were not found in the plasma following i.t. injection, demonstrating the absence of MS spillover during the procedure (FIGS. 3C and 3D). It was concluded that i.t. administration of MS results in local retention of the therapy.

Figures 4A, 4B, 4C, 4D, 4E:
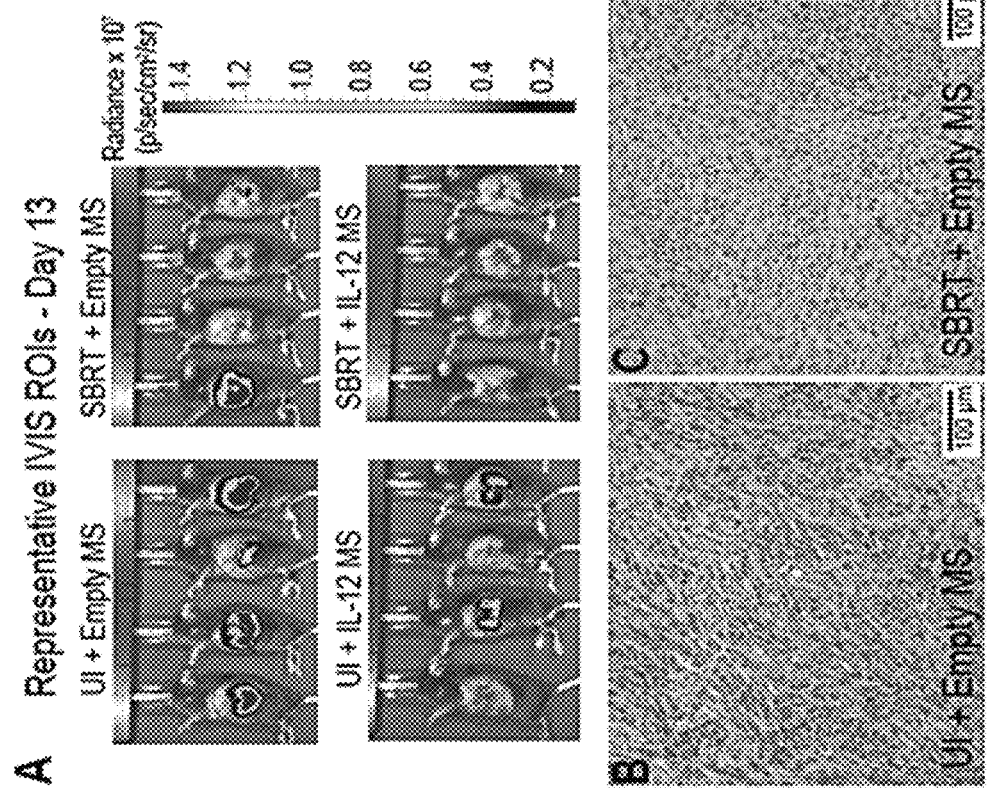
FIG. 4A through FIG. 4E, depicts exemplary data demonstrating representative IVIS ROIs and histology of orthotopic luciferase-expressing PDA model; KPC GEMM Initial Tumor Volumes and Long-Term Survivor Images.

Moderate reductions in tumor burden were observed following SBRT and IL12 MS treatments alone in the KCKO-luc mouse model (FIG. 4 and FIG. 5). Remarkably, the combination of SBRT+IL12 MS eradicated tumors by day 20 post-implantation, and lesions remained undetectable by IVIS bioluminescent imaging until measurements were terminated at day 60 (FIG. 2B and FIG. 4A). Histological analyses of day 11 tumors corroborated these antitumor effects, depicting regions of marked cell death and overwhelming immune infiltration in the SBRT/IL-12 MS group (FIGS. 4B-4E). Treatment with SBRT alone increased overall survival, with 20% demonstrating long-term survival greater than 120 days; however, SBRT/IL-12 MS treatment resulted in a significant benefit, with 100% of mice achieving long-term survival (FIG. 2C). To generalize these findings across other PC models, the analyses were repeated in the Pan02-luc model, a chemically induced and radioresistant cell line. Like KCKO-luc tumor-bearing mice, IL-12 MS delivery alone resulted in only minor reductions in tumor burden. Interestingly, combination therapy maintained synergistic antitumor effects even in the absence of strong monotherapy responses, as represented by both significantly decreased tumor burden and increased survival (FIGS. 2D and 2E, respectively). Furthermore, 10% of SBRT/IL-12 MStreated Pan02-luc mice resulted in long-term survival.

The investigation was expanded to the KPC genetically engineered mouse model (GEMM) (P48-Cre; LSL-$Kras^{G12D}$; $Tp53^{L/L}$) KPC mice were enrolled in treatment at 6-8 weeks of age after the development of prominent lesions. All mice used in the study had similar tumor volume measurements at the time of fiducial marker placement (FIG. 4F). SBRT/IL-12 MS, but neither treatment alone, significantly increased overall survival, demonstrating nearly triple the survival of untreated controls (FIG. 2F). Histological analysis of the day 11 SBRT/IL-12 MS-treated tumor (4 days post-IL-12 MS) revealed regions of pronounced cell death and immune infiltration relative to the untreated control (FIGS. 4G and 4H, respectively). Of note, this model results in the malignant transformation of all P48-expressing pancreatic ductal cells, eliminating the potential for cure. Even so, one SBRT/IL-12 MS-treated mouse was afforded marked survival benefit and, upon autopsy, was found to have cleared much of the pretreatment tumor mass and displayed splenomegaly, suggesting the development of a robust antitumor immune response (FIG. 4I). Taken together, these findings demonstrate a generalizable antitumor capacity of SBRT/IL-12 MS therapy that elicits survival benefits in multiple preclinical PDA models.

SBRT/IL12 MS Therapeutic Efficacy is Dependent Upon IFNγ Function

Figures 5A, 5B, 5C:
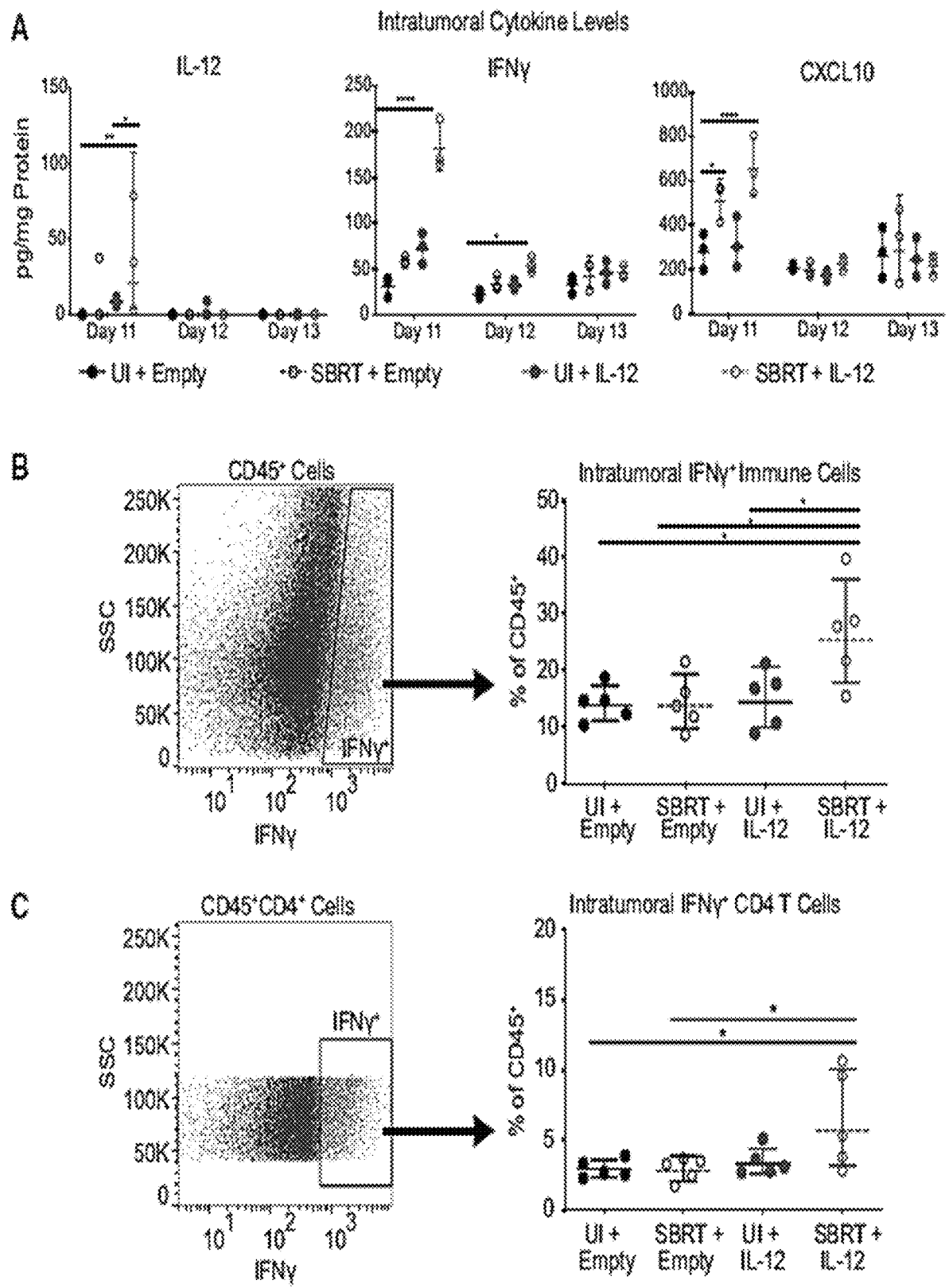
Figures 5D, 5E:
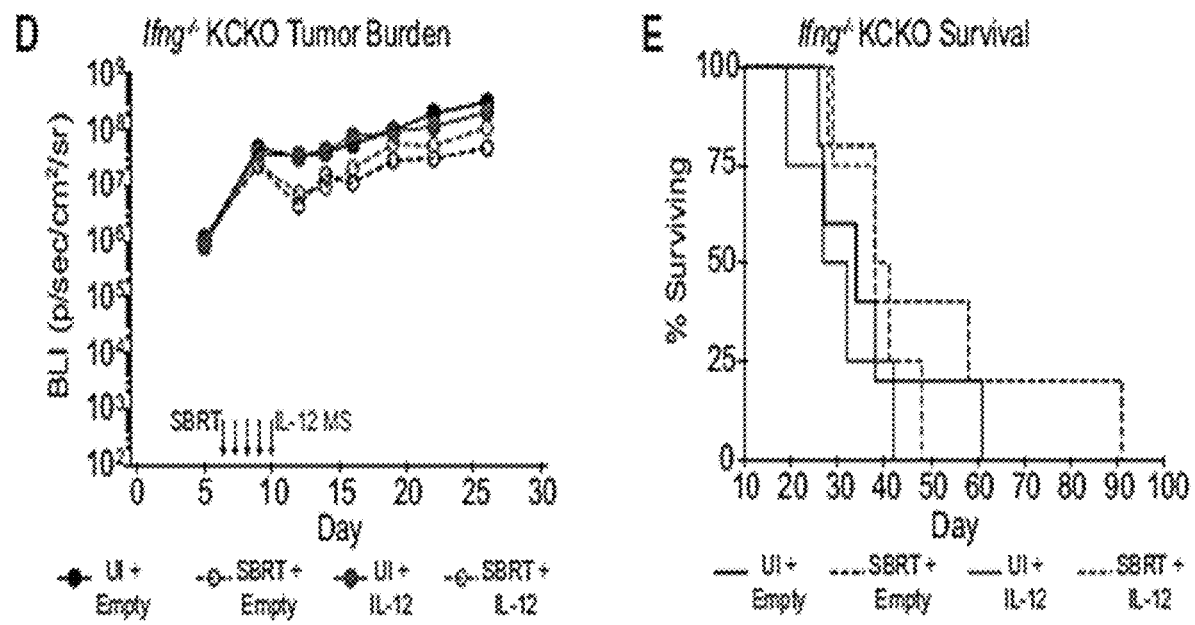
FIG. 5D and FIG. 5E SBRT/IL-12 MS-treated KCKO-luc orthotopic tumors (n=5) implanted in Ifng$^{-/-}$ mice were measured over time using IVIS bioluminescent imaging to track tumor growth (FIG. 5D), as well as survival analysis (FIG. 5E). For IVIS imaging analysis, values are presented as the geometric mean of maximum photon emissions within ROIs; Holm-Sidak test. For survival analyses, a Grehan-Breslow-Wilcoxon test was performed. Representative of one experiment. Significance relative to UI/empty MS group. *p<0.05, p<0.01, **p<0.0001.

Many of the proinflammatory biological effects of IL12 are mediated by IFNγ. The amount of intratumoral IFNγ was assayed following IL-12 MS treatment in the KCKO-luc orthotopic model. Luminex cytokine analysis of tumors following SBRT/IL-12 MS administration revealed significant inductions of IL-12 and IFNγ proteins only in the combination treatment group, for up to 24 (day 11) and 48 hours (day 12) following MS delivery, respectively. Interestingly, the highest levels of IFNγ production were observed within the first 24 hours (day 11) post-treatment. Concurrent analysis of CXCL10 levels corroborated IFNγ findings (FIG. 5A). Furthermore, flow cytometric analysis of day 11 tumors confirmed a significant increase in the percent of IFNγ-positive CD45+ immune cells (FIG. 5B) and CD4 T cells (FIG. 5C) in the SBRT/IL-12 MS treatment group.

To determine if the SBRT/IL-12 MS therapeutic effect was dependent upon IFNγ signaling, KCKO-luc orthotopic tumors were implanted in IFNγ null, $Ifng^{tm1Ts}$ ($Ifng^{-/-}$) mice. As expected, IVIS growth and overall survival measurements demonstrated a general increase in baseline tumor growth upon loss of the cytokine. IFNγ deletion also resulted in the complete abatement of the IL12 MS therapeutic response (FIG. 5D and FIG. 5E; compare to FIG. 2B and FIG. 2C). Altogether, these data demonstrate the therapeutic dependence of SBRT/IL12 MS treatment on robust intratumoral production of IFNγ.

Figure 6A:
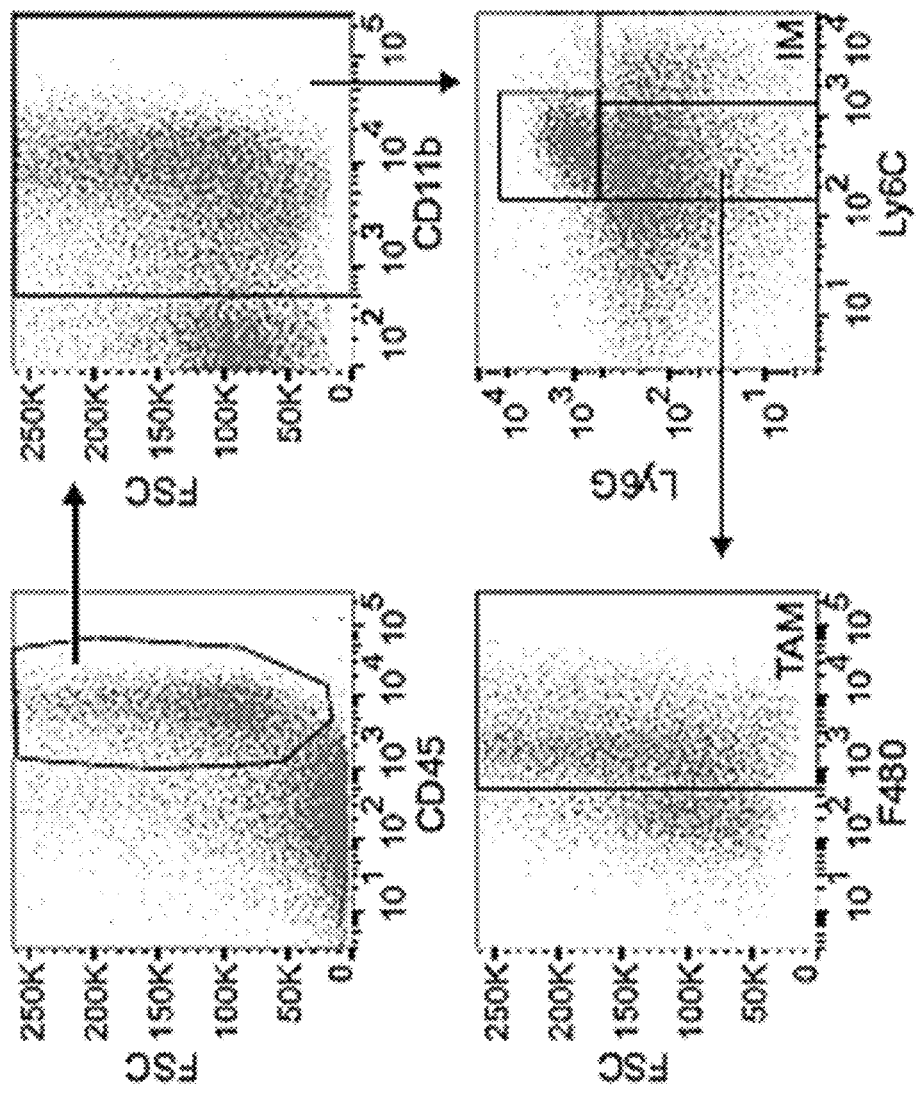
FIG. 6A through FIG. 6E, depicts exemplary data demonstrating that PDA myeloid populations are reprogrammed by SBRT/IL-12 MS treatment. SBRT/IL-12 MS-treated KCKO-luc orthotopic tumors were harvested on days 11 and 14 and digested into single cell suspensions for flow cytometry (n=4-5) and RNA-seq analyses.
Figure 6B:
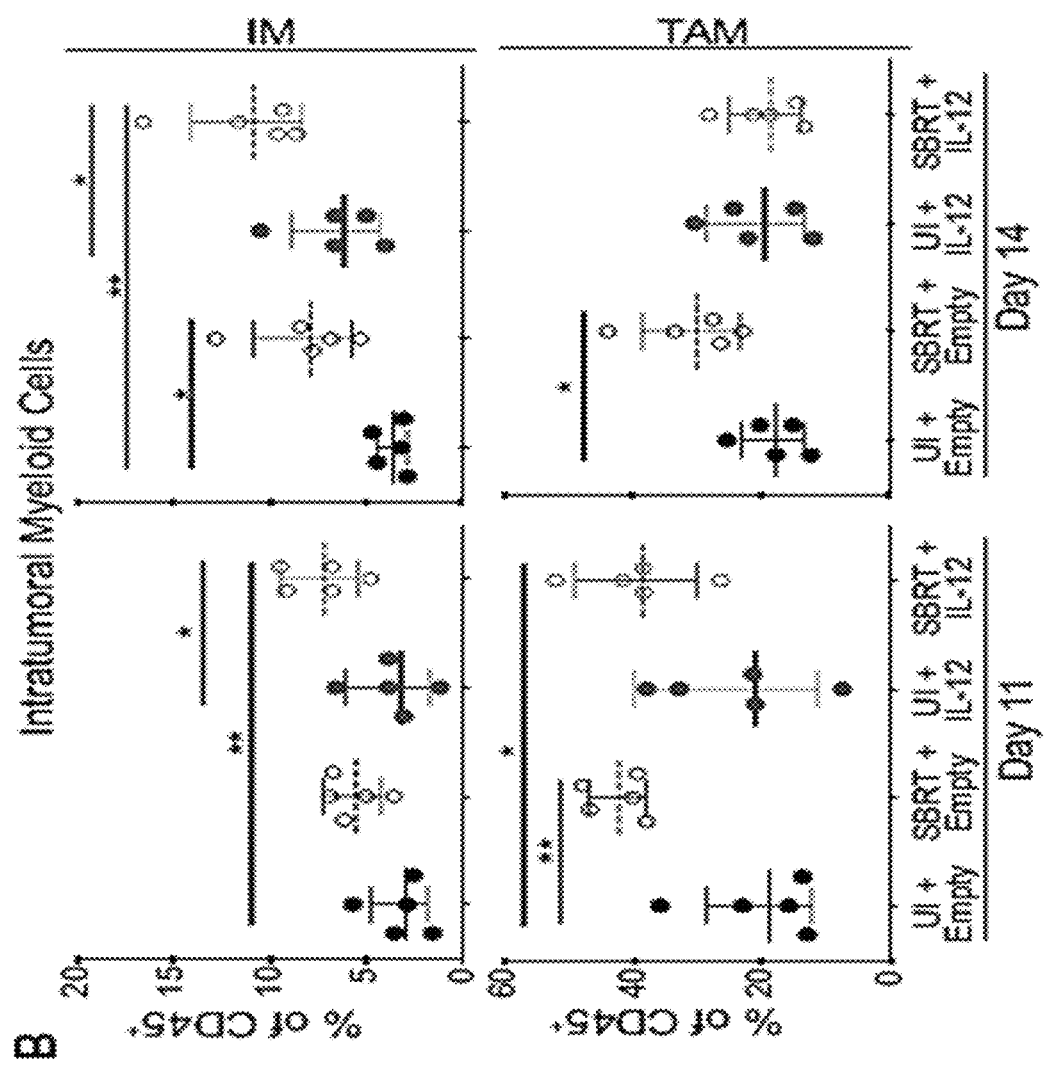

PC Myeloid Populations are Polarized Toward a Pro-Inflammatory M1 Phenotype by SBRT/IL12 MS Treatment Radiotherapy can bolster intratumoral immunosuppressive myeloid populations in the days following treatment (Walle et al., 2018, Ther Adv Med Oncol, 10:1758834017742575; Connolly et al., 2016, Oncotarget, 7, 86522-86535). To assess SBRT/IL-12 MS effects on myeloid suppressor recruitment, flow cytometry was performed on day 11 KCKO-luc tumors. Analyses revealed SBRT-dependent increases in $CD11b^+Ly6C^+Ly6G''$ IMs, $CD11b^+Ly6C^{mod}Ly6G^-F480^+$ TAMs, and $CD11b^+Ly6C^{mod}Ly6G^+$ tumor-associated neutrophils (TANs). These responses were also generally unaffected by IL-12 MS treatment alone or SBRT/IL-12 MS (FIGS. 6A, 6B, left panels, and 7A). Interrogation of the day 14 time point revealed similar treatment effects on IMs; however, interestingly, SBRT-dependent increases in TAMs were found to be abrogated by the addition of IL-12 MS (FIG. 6B, right panels).

Figure 6C:
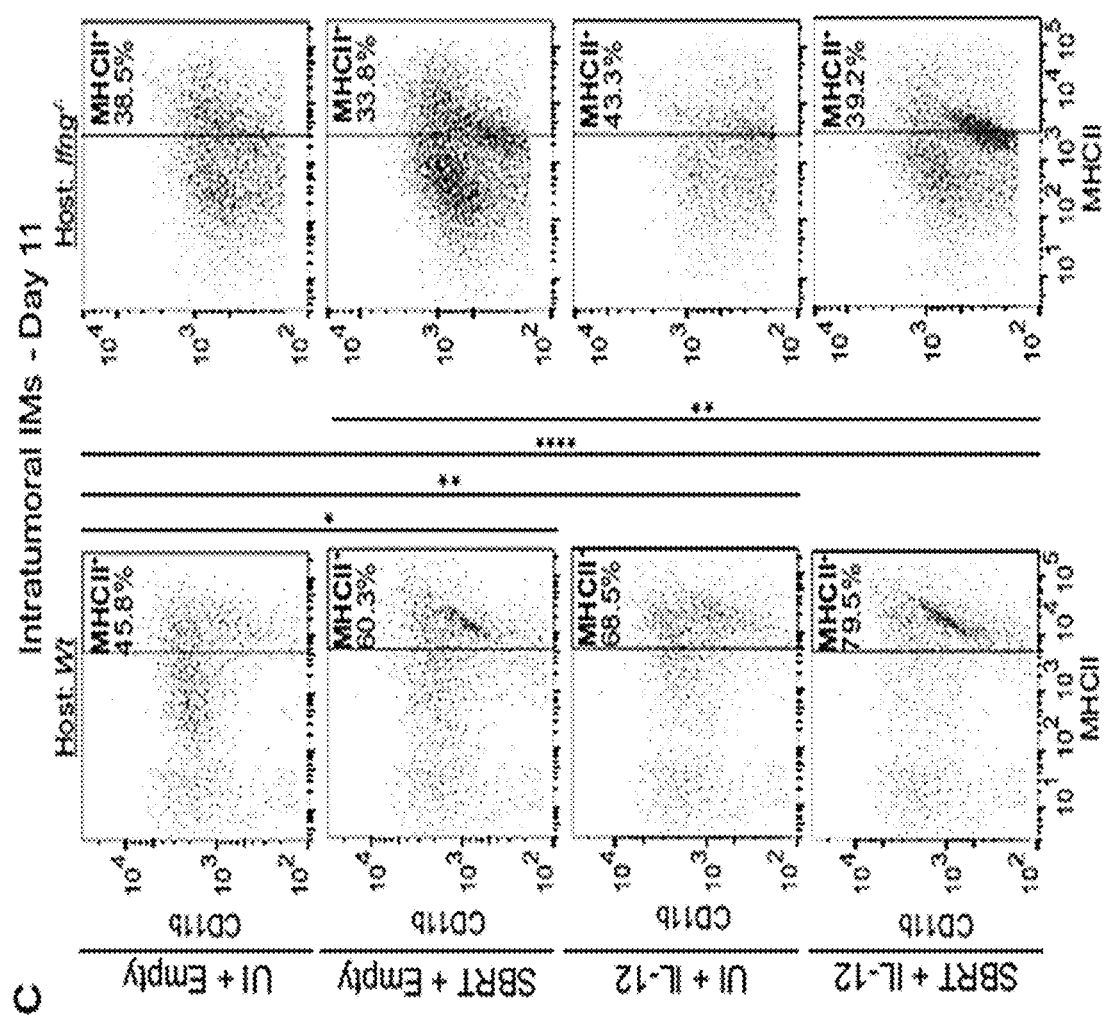
Figures 7A, 7B:
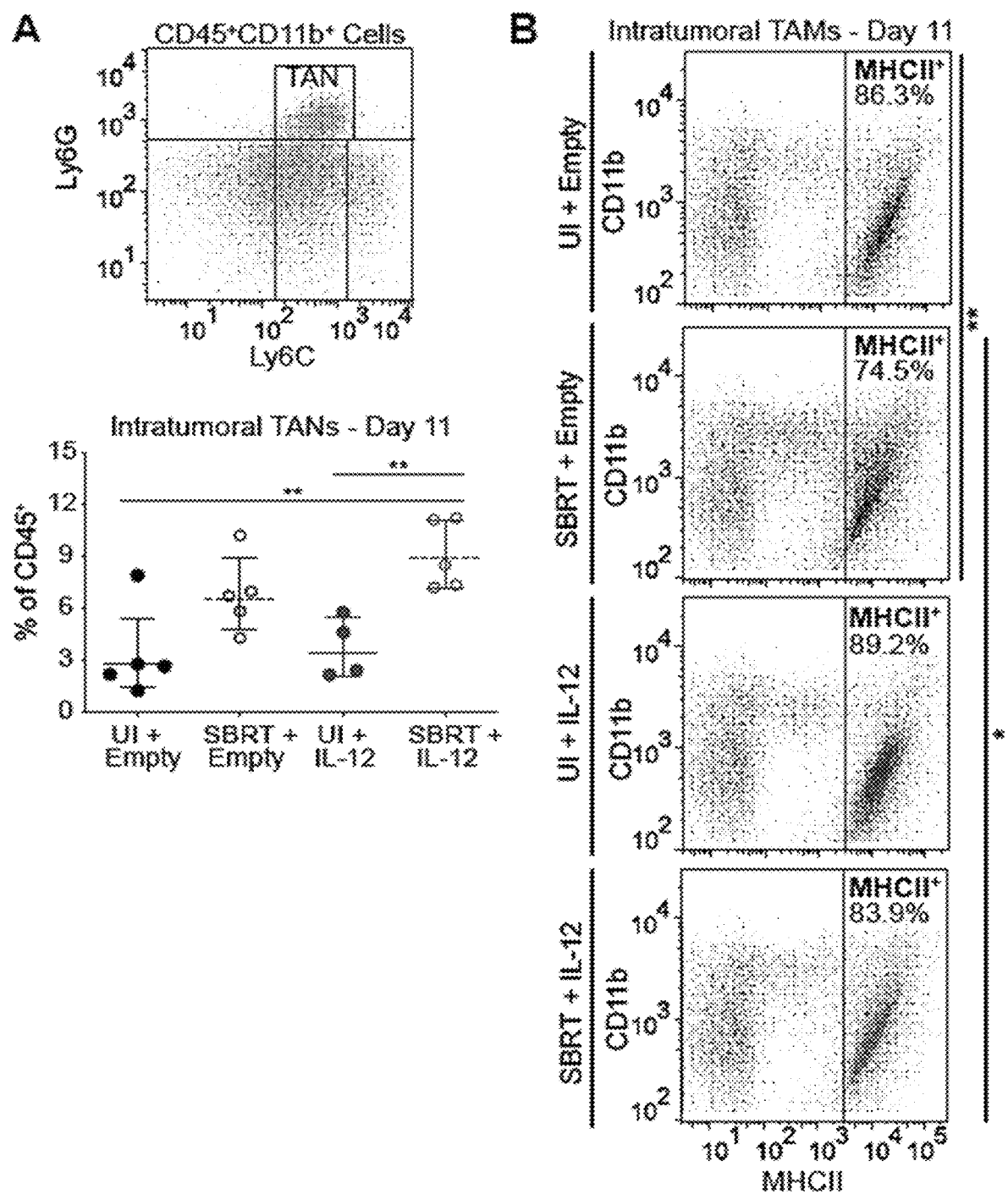
FIG. 7A through FIG. 7C, depicts exemplary experimental results demonstrating the expanded intratumoral myeloid suppressor analyses. SBRT/IL-12 MS-treated KCKO-luc orthotopic tumors were harvested on days 11 and 14 and digested into single cell suspensions for flow cytometry (n=4-5) and RNA-seq (n=3) analyses.

Having observed a robust increase in intratumoral IFNγ protein levels upon SBRT/IL12 MS treatment, evidence of inflammatory monocyte and/or tumor-associated macrophage reprogramming in the KCKO-luc model was sought. Day 11 flow cytometric analysis demonstrated significantly increased percentages of $MHCII^+$ IMs upon IL-12 MS and SBRT/IL-12 MS treatments, indicative of reprogramming (FIG. 6C, left panels). Repeated analyses in the IFNγ' background identified this increase in myeloid immune cells as IFNγ-independent (FIG. 6C, right panels). TAMs that arise from circulating IMs are almost exclusively MHCII+, and reductions in MHCII expression have been shown to promote tumor progression (Zhu et al., 2017, Immunity 47:597; Wang et al., 2011, BMC Immunol, 12:43). SBRT was found to reduce the percentage of MHCII+ TAMs in KCKO-luc tumors, whereas the addition of IL-12 MS rescued the MHCII+ phenotype (FIG. 7B).

Figure 7C:
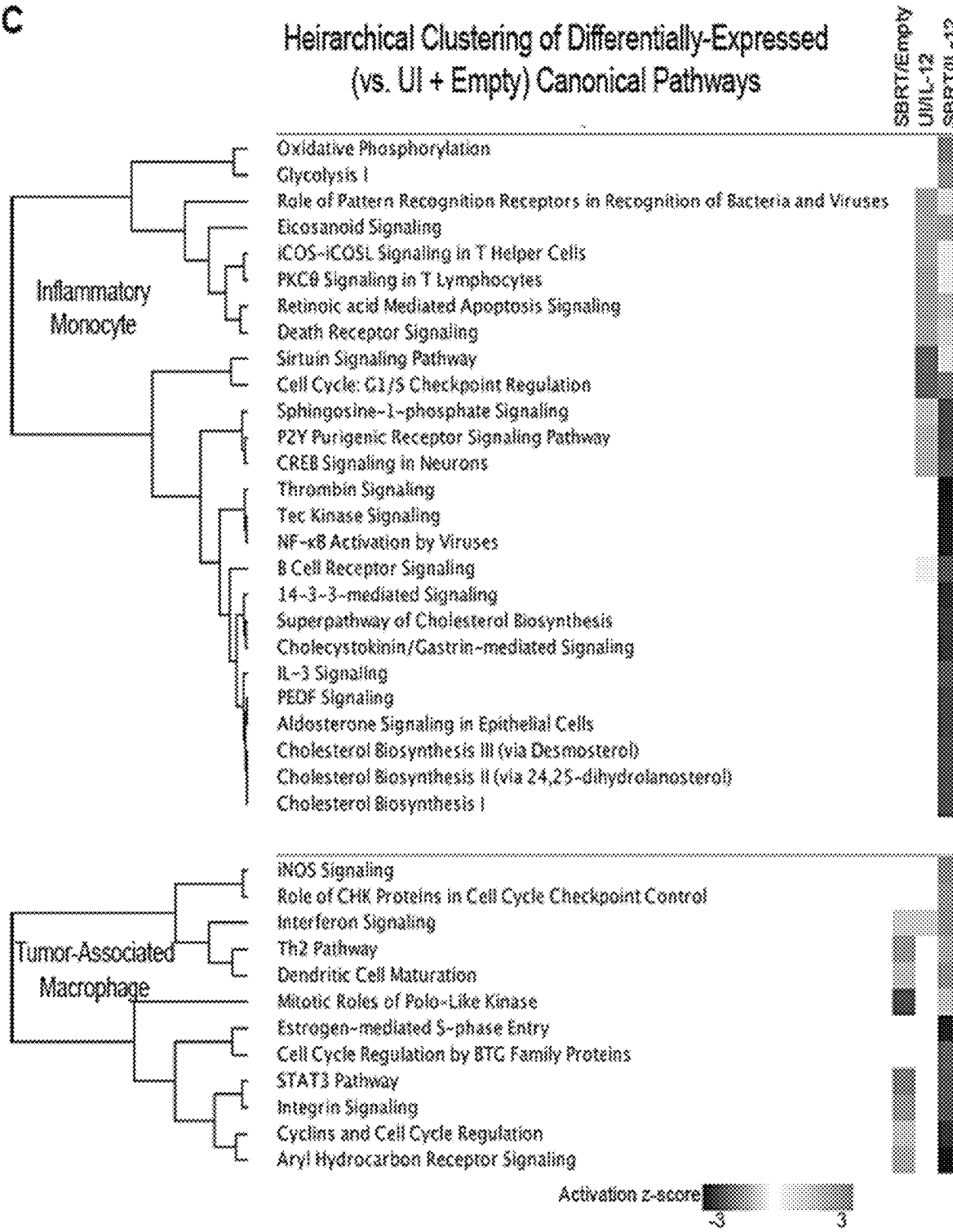
Figures 8A, 8B, 8C, 8D:
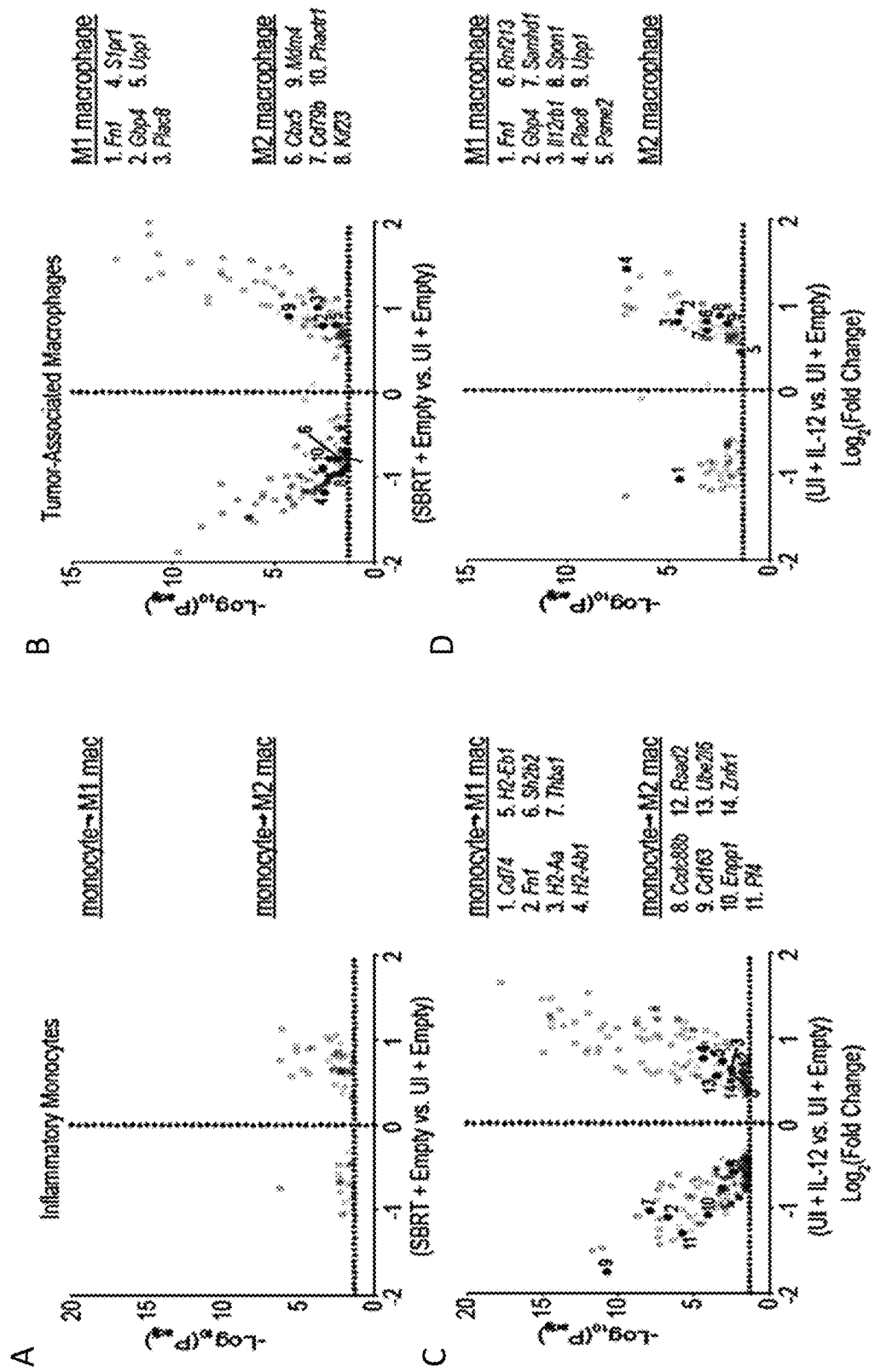
FIG. 8A through FIG. 8D, depicts exemplary experimental data demonstrating the inflammatory monocyte and TAM DEGs following SBRT/Empty MS (FIG. 8A and FIG. 8B, respectively) and UI/IL-12 MS treatments (FIG. 8C and FIG. 8D, respectively) (vs. UI/Empty MS controls) were compared to monocyte, classical M1, and alternative M2 macrophage genesets from the Broad Institute MSigDB (GSE5099) and gene matches are presented in volcano plots. left=downregulated, right=upregulated. Representative of one experiment. *p<0.05, **p<0.01.

For added confirmation of myeloid reprogramming, RNA sequencing (RNA-seq) analysis was performed on IM and TAM populations sorted from KCKO-luc tumors. Ingenuity pathway analysis of differentially expressed genes (DEGs; versus unirradiated/empty MS;_1.5<z<1.5) demonstrated the upregulation of activation pathways (eicosanoid and inducible nitric oxide synthase [iNOS]) accompanied by the downregulation of immunosuppressive pathways (sphingosine-1, P2Y purinergic receptor, thrombin, and STAT3)

across both populations (Norris et al., 2014, Adv Biol Regul, 54:99-110; MacMicking et al., 1997, Annu Rev Immunol, 15:323-350; Park et al., 2014, Cell Signal, 26(10):2249-2258; Barbera et al., 2016, J Leukoc Biol, 99(2):289-299; White et al., 2015, PloS one, 10(9):e0138748; Mu et al., 2018, Cell Cycle, 17(4):428-38). Interestingly, only SBRT/IL-12 MS treatment resulted in the differential regulation of metabolic pathways in IMs involving glycolysis (pro-activation, upregulated), and cholesterol biosynthesis (pro-suppression, downregulated) (FIG. 7C) (Freemerman et al., 2014, The Journal of biological chemistry, 289(11):7884-7896; Wei et al., 2015, J Lipid Res, 56(12):2337-2347). In both IMs and TAMs, IFNγ activation was identified as a top upstream regulator of differential expression upon SBRT/IL-12 MS treatment (Tables 1 and Table 2).

TABLE 1

Top Upstream Regulators of Intratumoral Inflammatory Monocyte Response to SBRT/IL-12 MS. SBRT/IL-12 MS-treated KCKO-luc orthotopic tumors were harvested on day 11 and digested into single cell suspensions. Lysates were flow sorted to isolate CD11b+Ly6C+Ly6G− IMs for RNA-seq analysis. Differentially expressed genes (versus unirradiated + empty MS controls) were analyzed using Ingenuity Pathway Analysis comparing each of the 3 treatment groups to unirradiated + empty MS controls (n = 3). Top activated and inhibited upstream regulators (p-values of overlap <10-20) of differentially-expressed pathways are represented. Representative of one experiment.

| Upstream Regulator | Molecule Type | Predicted Activation State | Activation z-score | p-value of overlap |
|---|---|---|---|---|
| IFNG | cytokine | Activated | 7.511 | 4.93E−51 |
| IL10RA | transmembrane receptor | Inhibited | −8.128 | 1.24E−41 |
| STAT1 | transcription regulator | Activated | 6.682 | 2.11E−38 |
| TNF | cytokine | Activated | 2.005 | 8.53E−31 |
| IL1B | cytokine | | 0.816 | 8E−30 |
| TRIM24 | transcription regulator | Inhibited | −5.28 | 1.2E−28 |
| APP | other | Activated | 4.556 | 4.24E−27 |
| STAT3 | transcription regulator | | −1.822 | 4.92E−27 |
| IFNB1 | cytokine | Activated | 5.313 | 4.36E−26 |
| IFNAR1 | transmembrane receptor | Activated | 4.039 | 8.94E−26 |
| IL4 | cytokine | | −0.474 | 3.33E−24 |
| IRF7 | transcription regulator | Activated | 6.624 | 7.85E−24 |
| TGFB1 | growth factor | Inhibited | −2.469 | 1.5E−23 |
| IL6 | cytokine | | 0.663 | 6.41E−23 |
| IRF1 | transcription regulator | Activated | 4.431 | 2.31E−21 |
| IL21 | cytokine | Activated | 4.723 | 2.36E−21 |
| IFNAR | group | Activated | 5.254 | 1.38E−20 |
| CD40LG | cytokine | Activated | 2.515 | 2.61E−20 |

TABLE 2

Top Upstream Regulators of Intratumoral Tumor-Associated Macrophage Response to SBRT/IL-12 MS. SBRT/IL-12 MS-treated KCKO-luc orthotopic tumors were harvested on day 11 and digested into single cell suspensions. Lysates were flow sorted to isolate CD11b+Ly6C−Ly6G−F480+ TAMs for RNA-seq analysis. Differentially-expressed genes (versus unirradiated + empty MS controls) were analyzed using Ingenuity Pathway Analysis comparing each of the 3 treatment groups to unirradiated + empty MS controls (n = 3). Top activated and inhibited upstream regulators (p-values of overlap <10-20) of differentially-expressed pathways are represented. Representative of one experiment.

| Upstream Regulator | Molecule Type | Predicted Activation State | Activation z-score | p-value of overlap |
|---|---|---|---|---|
| TP53 | transcription regulator | Activated | 4.691 | 1.21E−43 |
| IL10RA | transmembrane receptor | Inhibited | −7.1 | 1.14E−36 |
| IFNG | cytokine | Activated | 7.545 | 5.61E−34 |
| IRF7 | transcription regulator | Activated | 6.316 | 7.96E−34 |
| STAT1 | transcription regulator | Activated | 6.442 | 1.07E−33 |
| IFNB1 | cytokine | Activated | 5.792 | 1.16E−33 |
| CDKN1A | kinase | Activated | 2.97 | 1.41E−29 |
| TRIM24 | transcription regulator | Inhibited | −4.59 | 8.89E−28 |
| IL4 | cytokine | Inhibited | −3.205 | 3.83E−26 |
| IL6 | cytokine | | 0.93 | 3.67E−25 |
| IFNA | group | Activated | 5.431 | 1.17E−24 |
| ERBB2 | kinase | Inhibited | −4.055 | 1.84E−24 |
| TGFB1 | growth factor | | −1.674 | 1.05E−23 |
| TNF | cytokine | Activated | 3.817 | 2.32E−23 |
| E2F4 | transcription regulator | | 0.391 | 6.89E−23 |
| TBX2 | transcription regulator | Inhibited | −5.053 | 1.76E−22 |
| IFNA/B | group | Activated | 3.677 | 7.99E−22 |
| STAT3 | transcription regulator | Inhibited | −2.388 | 1.38E−21 |
| CDKN2A | transcription regulator | Activated | 4.415 | 5.19E−21 |
| IFNAR | group | Activated | 5.009 | 1.25E−20 |
| CSF2 | cytokine | Inhibited | −2.488 | 1.4E−20 |
| IRF3 | transcription regulator | Activated | 5.666 | 2.85E−20 |
| IRF1 | transcription regulator | Activated | 4.257 | 7.53E−20 |
| mir-21 | microma | Inhibited | −2.54 | 7.84E−20 |

Figure 6D:
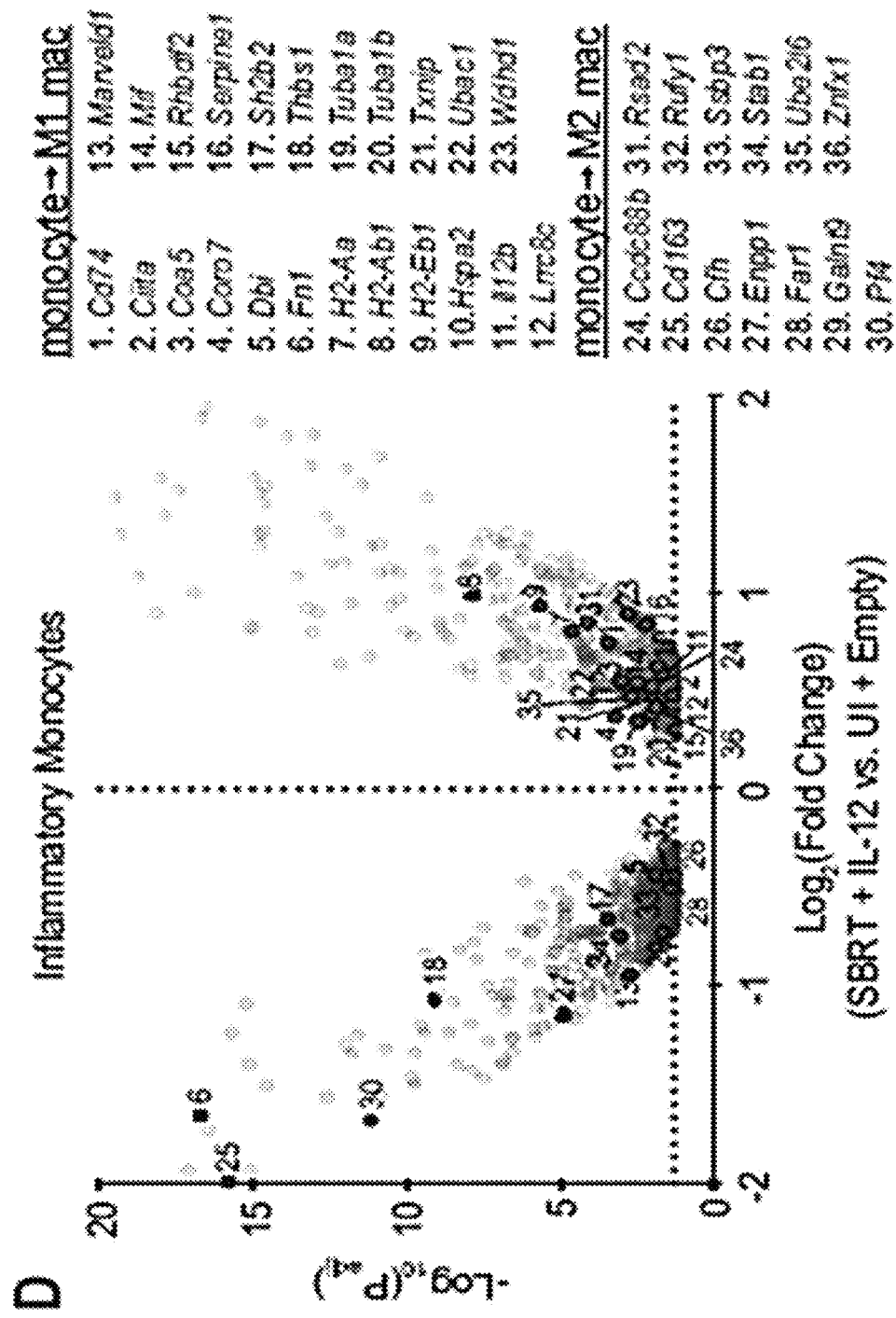
Figure 6E:
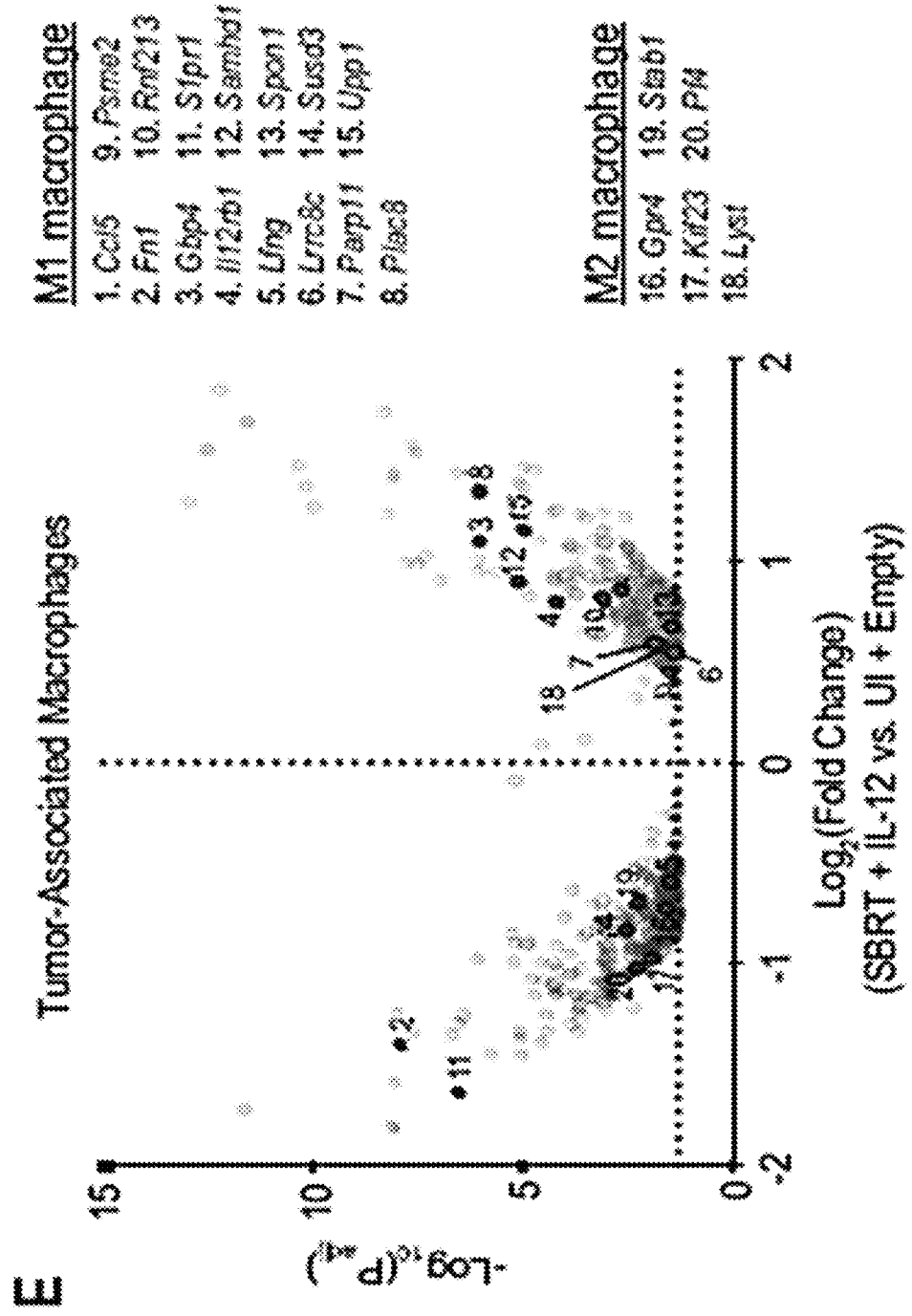

Expression patterns were analyzed at the individual gene level by dichotomizing DEGs ($|\log_2[\text{fold-change}]|>0.5$ versus unirradiated/empty MS; $p<0.05$) into monocyte, M1, and M2 macrophage subsets by using immunologic gene sets from the Molecular Signatures Database (MSigDB) provided by the Broad Institute (MSigDB: GSE5099). Using this classification strategy, an M1-skewed gene upregulation was identified after SBRT/IL-12 MS treatment in both myeloid cell types (IM: monocyte/M1=31, monocyte/M2=7; TAM: M1=13, M2=3), in addition to the predominant downregulation of M2-like genes (IM: monocyte/M2=9 genes, monocyte/M1=4 genes; TAM: M2=4, M1=1) (FIGS. 6D and 6E, respectively). Monotherapy treatment with SBRT or IL-12 MS was insufficient to activate comparable levels of differential gene expression in IMs or TAMs (FIGS. 8A-8D).

Figure 6F:
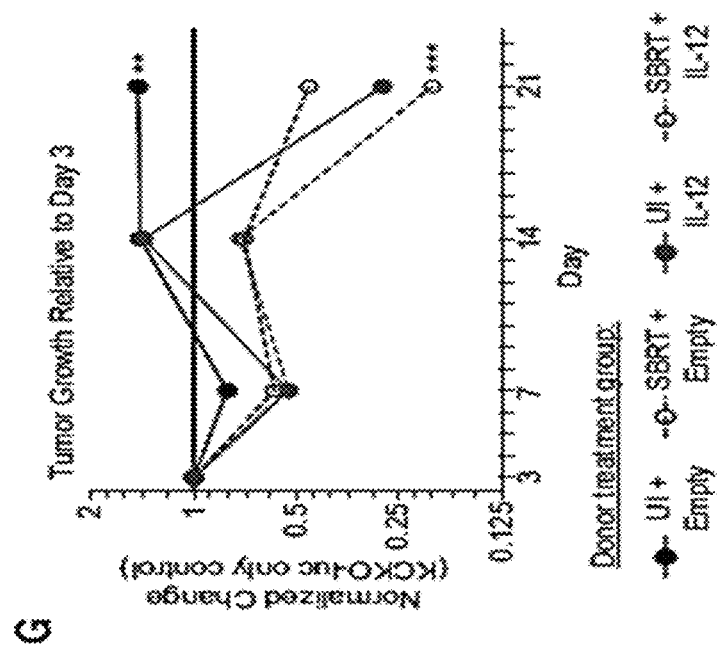
FIG. 6F and FIG. 6G depict a schematic (FIG. 6F) of IM/TAM transplant experiment. KCKO-luc tumors (n=4-5) from each SBRT/IL-12 MS treatment group were harvested and IMs and TAMs were flow sorted. IMs/TAMs from each group were pooled with fresh KCKO-luc cells and orthotopically implanted into naive mice (n=4-5). No further treatment was administered.
Figure 6G:
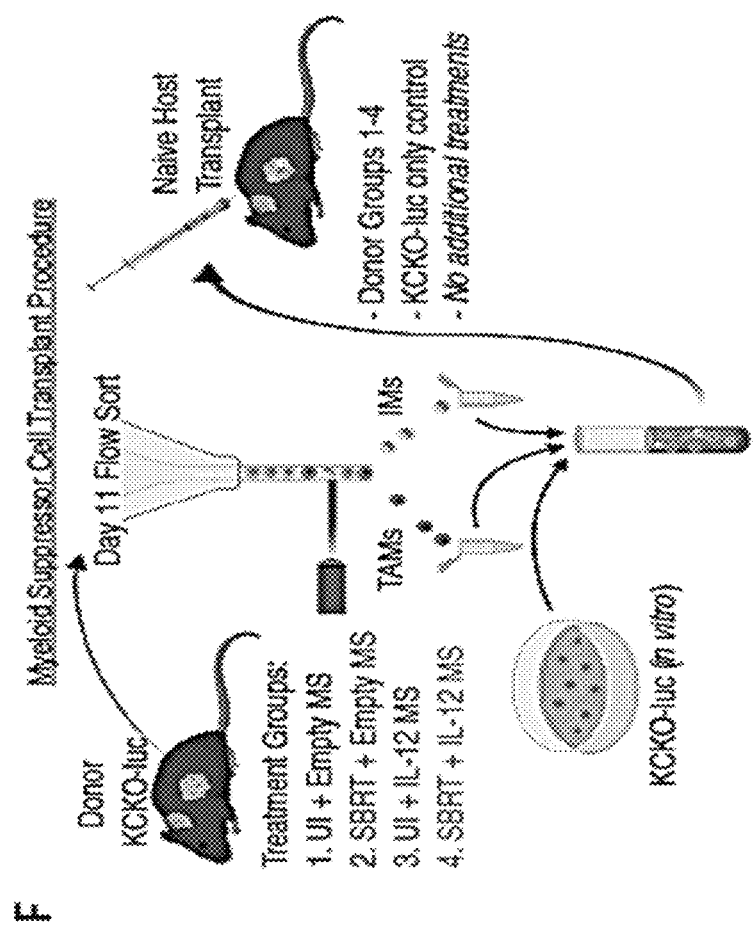

To assess the functional impact of myeloid polarization on KCKO-luc tumors, IM/TAM transplants of SBRT/IL-12 MS-treated populations were performed (FIG. 6F). Briefly, IMs and TAMs were sorted from KCKO-luc tumors, and pooled together with freshly cultured KCKO-luc cells. Cell mixtures from each SBRT/IL-12 MS treatment group were orthotopically implanted into naive hosts that received no further treatment. Compared to control KCKO-luc-only tumors, the addition of untreated IM/TAM pools promoted significant increases in relative tumor growth, demonstrating the well-documented protumor capacities of myeloid suppressors. Conversely, the transplantation of SBRT/IL-12 MS-treated IM/TAM pools significantly suppressed tumor outgrowth (FIG. 6G). Altogether, these findings demonstrate that SBRT/IL-12 MS treatment induces a cumulative repolarization of the intratumoral myeloid compartment toward an activated, antitumor state.

IFNγ Production is Necessary to Drive Antitumor T Cell Ratios

Figure 9A:
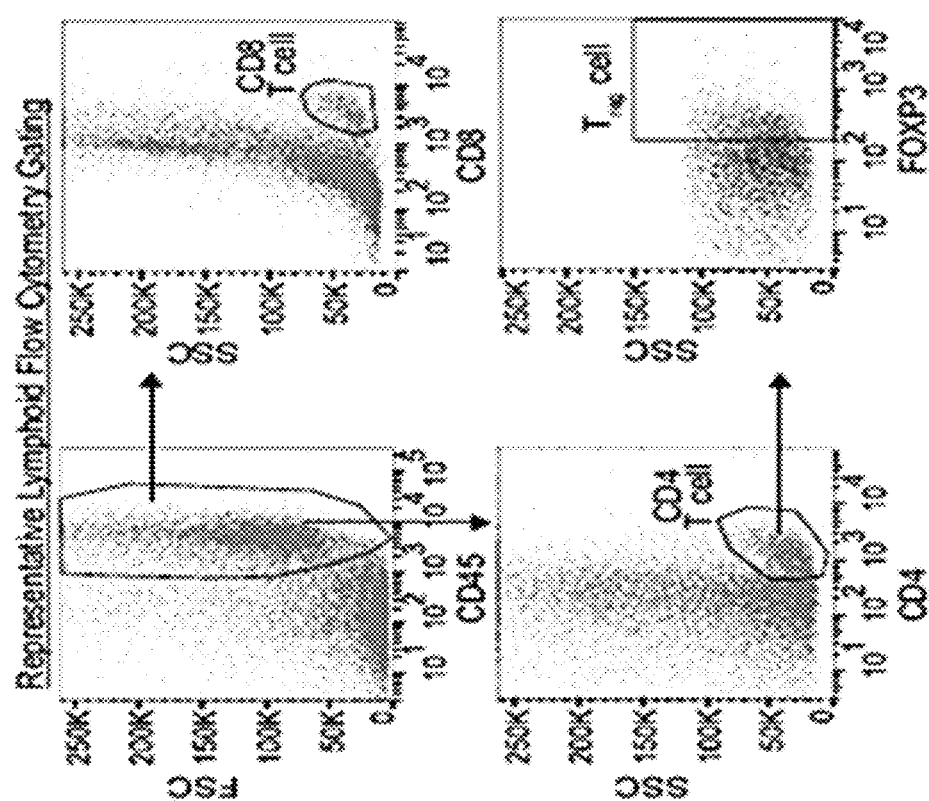
FIG. 9A through FIG. 9D, depicts exemplary experimental data demonstrating that SBRT/IL-12 MS therapeutic efficacy is dependent upon IFNγ-driven antitumor T cell ratios and robust CD8 T cell activation. SBRT/IL-12 MS-treated KCKO-luc orthotopic tumors were harvested on days 11 and 14 and digested into single cell suspensions for flow cytometric analysis (n=4-5).
Figure 9B:
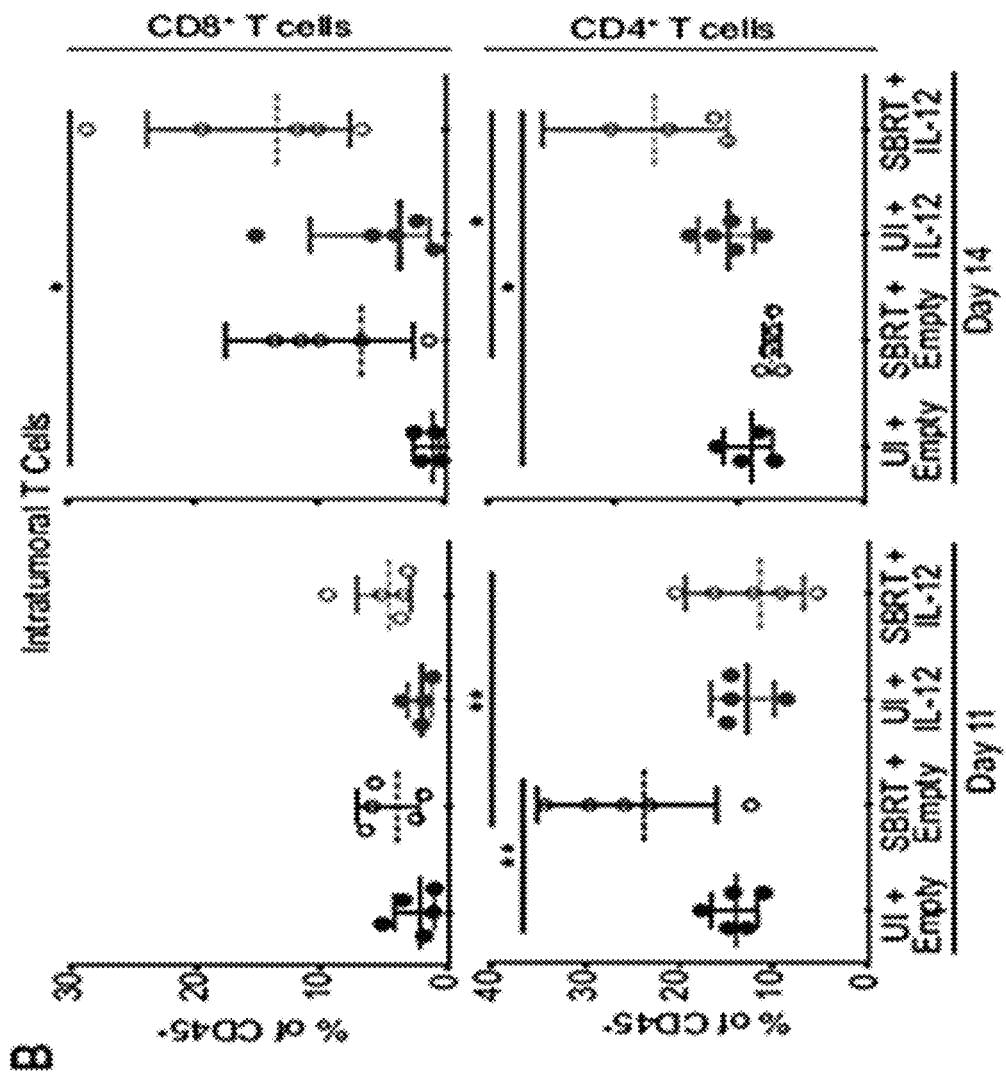

To validate the human PDAC findings of increased T cell infiltrate following SBRT therapy (FIG. 1), flow cytometry analysis was performed on KCKO-luc tumors using a lymphoid marker panel (FIG. 9A). Analysis of tumors at day 11 demonstrated modest increases in the percentage of CD8 T cells following SBRT and SBRT/IL-12 treatments; however, by day 14, SBRT-dependent CD8 increases were more pronounced, reaching significance in the SBRT/IL-12 MS group (FIG. 9B, top panels). CD4 T cells were significantly increased by SBRT treatment at day 11, and interestingly, the effect was abrogated by the addition of IL-12 MS. Conversely, by day 14, SBRT/IL-12 MS combination had elicited a significant increase in the CD4 compartment (FIG. 9B, bottom panels). Antigen-presenting cells (APCs) and other lymphocyte lineages, including B, natural killer (NK), and CD8$^+$NK1.1$^+$ cells, were found to be unchanged or decreased following SBRT/IL-12 MS treatments (FIGS. 10B-10D).

Figure 9C:
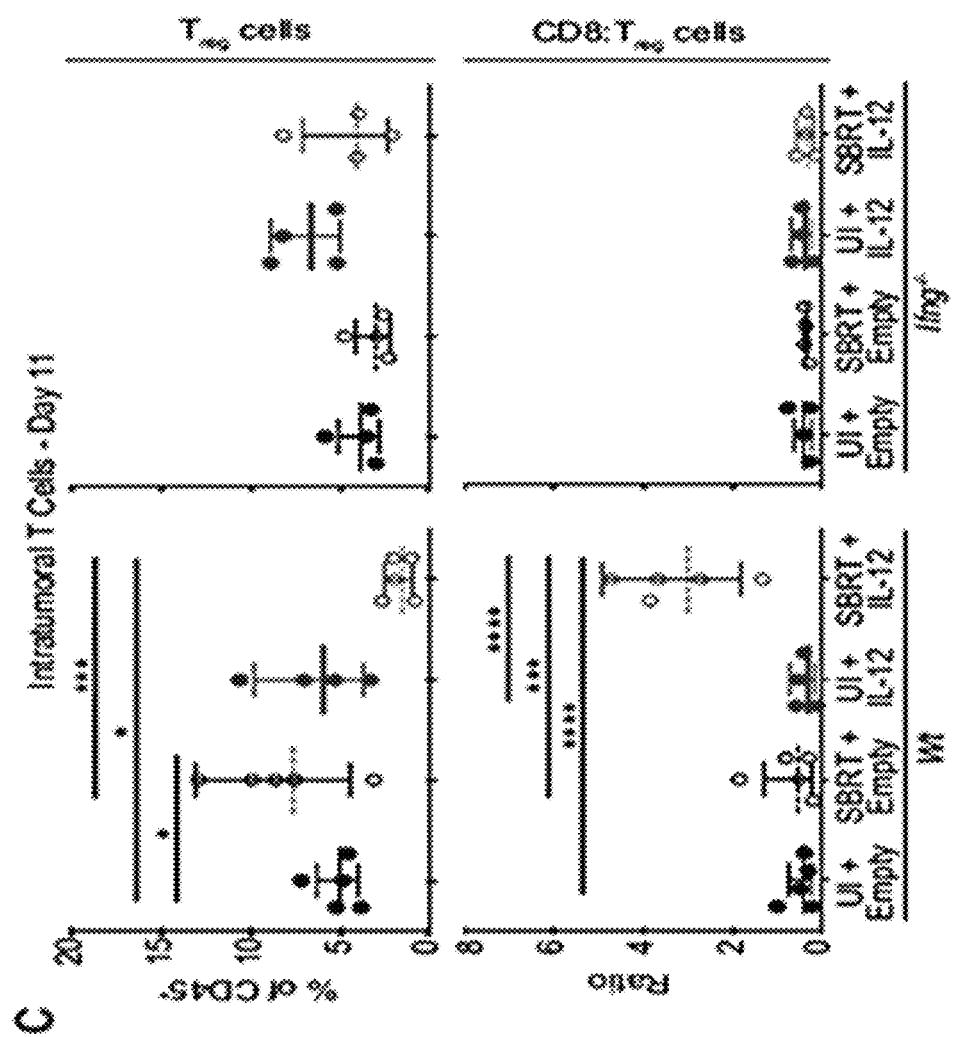
Figures 11A, 11B, 11C:
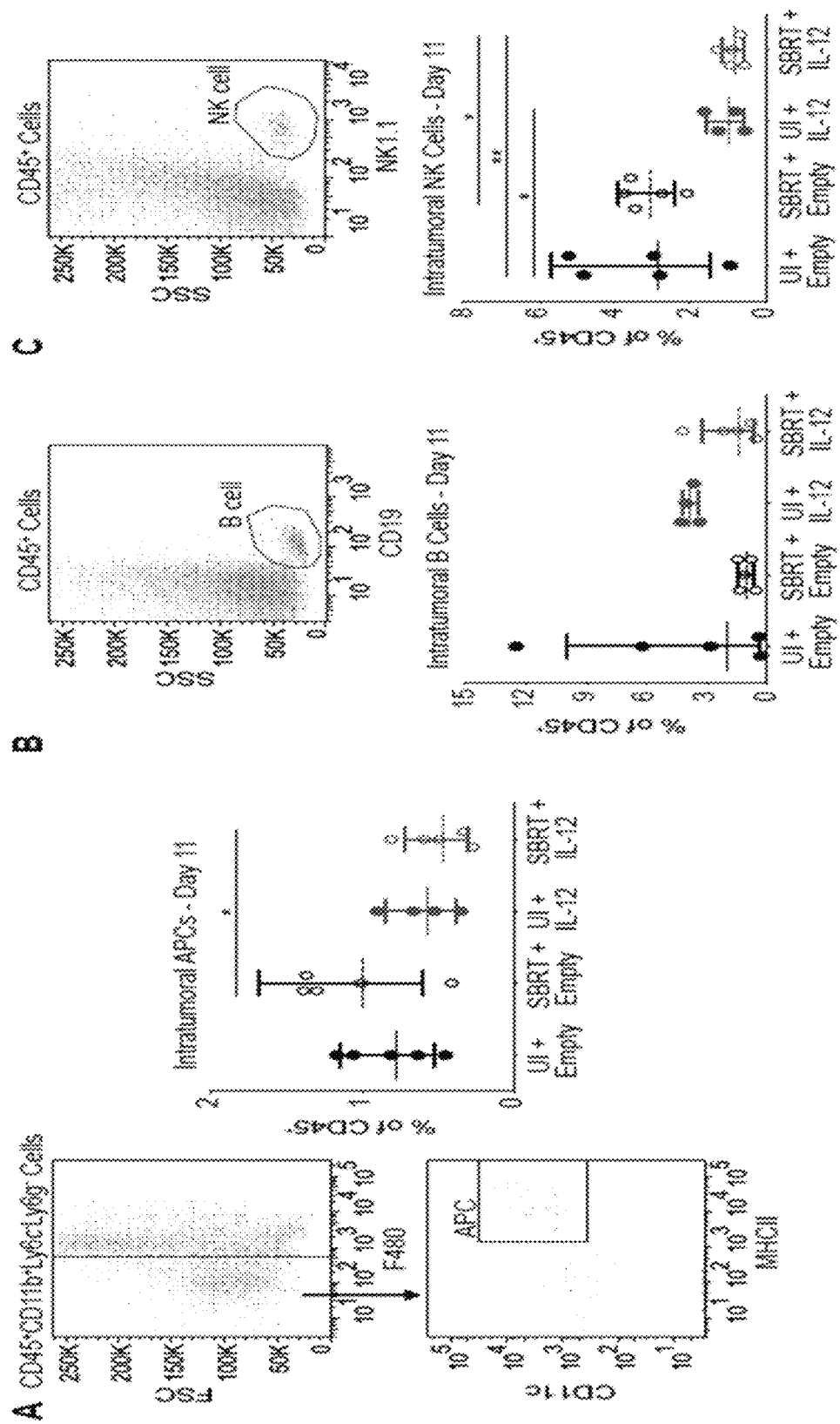
FIG. 11A through FIG. 11E, depicts exemplary experimental data demonstrating a comprehensive analysis of KCKO-luc tumor immune infiltration following SBRT/IL-12 MS therapy. SBRT/IL-12 MS-treated KCKO-luc orthotopic tumors (n=4-5) were harvested on day 11 and digested into single cell suspensions for flow cytometric analysis.
Figures 11D, 11E:
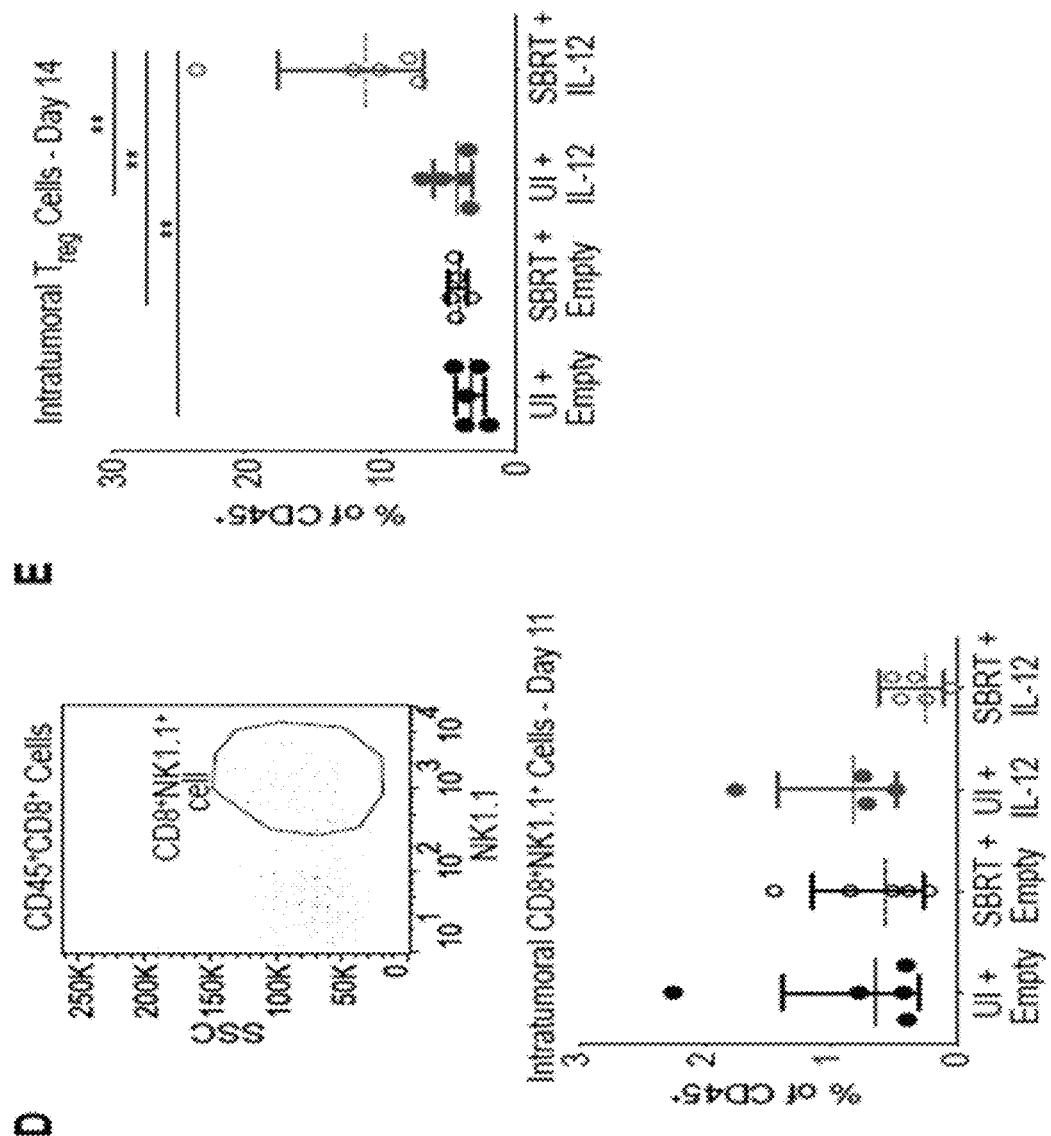

Much like the M1/M2 paradigm, IFNγ drives CD4$^+$ T cells toward a proinflammatory T helper type 1 ($T_h1$) program (Zhou et al., 2009, Immunity, 30(5):646-655). To assess the inflammatory status of intratumoral CD4+ T cells at day 11, staining of the $T_{reg}$ transcription factor Foxp3 was performed, and a significant increase in CD4+/Foxp3+$T_{reg}$ cells was observed with SBRT treatment. Interestingly, the addition of IL12 MS resulted in a reduced percentage of $T_{reg}$ cells, and repeating this experiment in IFNγ' mice confirmed the dependence of this effect on the proinflammatory cytokine (FIG. 9C, top panels). Interestingly, an analysis of day 14 KCKO-luc tumors demonstrated a significant rebound in Treg cells with SBRT/IL-12 MS treatment, suggesting that CD4 reprogramming was a transient event (FIG. 11E). Combining CD8 T cell and $T_{reg}$ cell distributions to assess the ratio of activated T cells, a significant increase in the CD8/$T_{reg}$ ratio was observed only in the SBRT/IL12 MS treatment group that was again lost in the IFNγ$^{-/-}$ host background (FIG. 9C, bottom panels). These findings suggest that SBRT and IL-12 MS treatments cooperatively increase immunogenic T cell ratios in KCKO tumors by recruiting T cells from the periphery, and subsequently eliminating immunosuppressive regulatory programming.

Figure 9D:
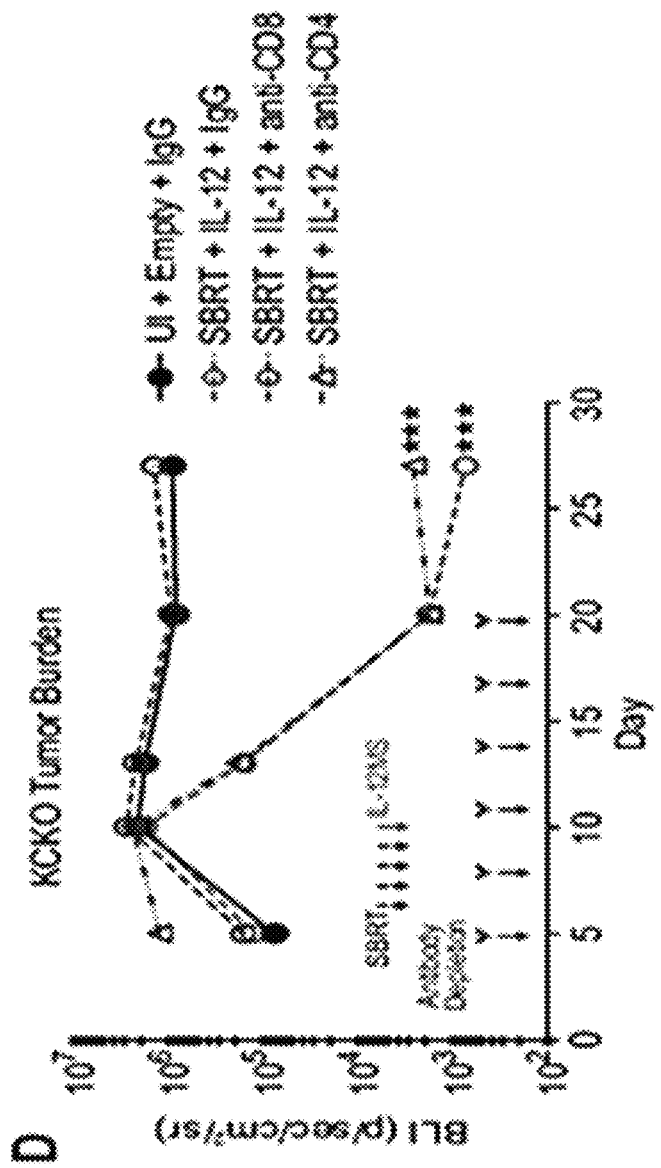
Figure 12A:
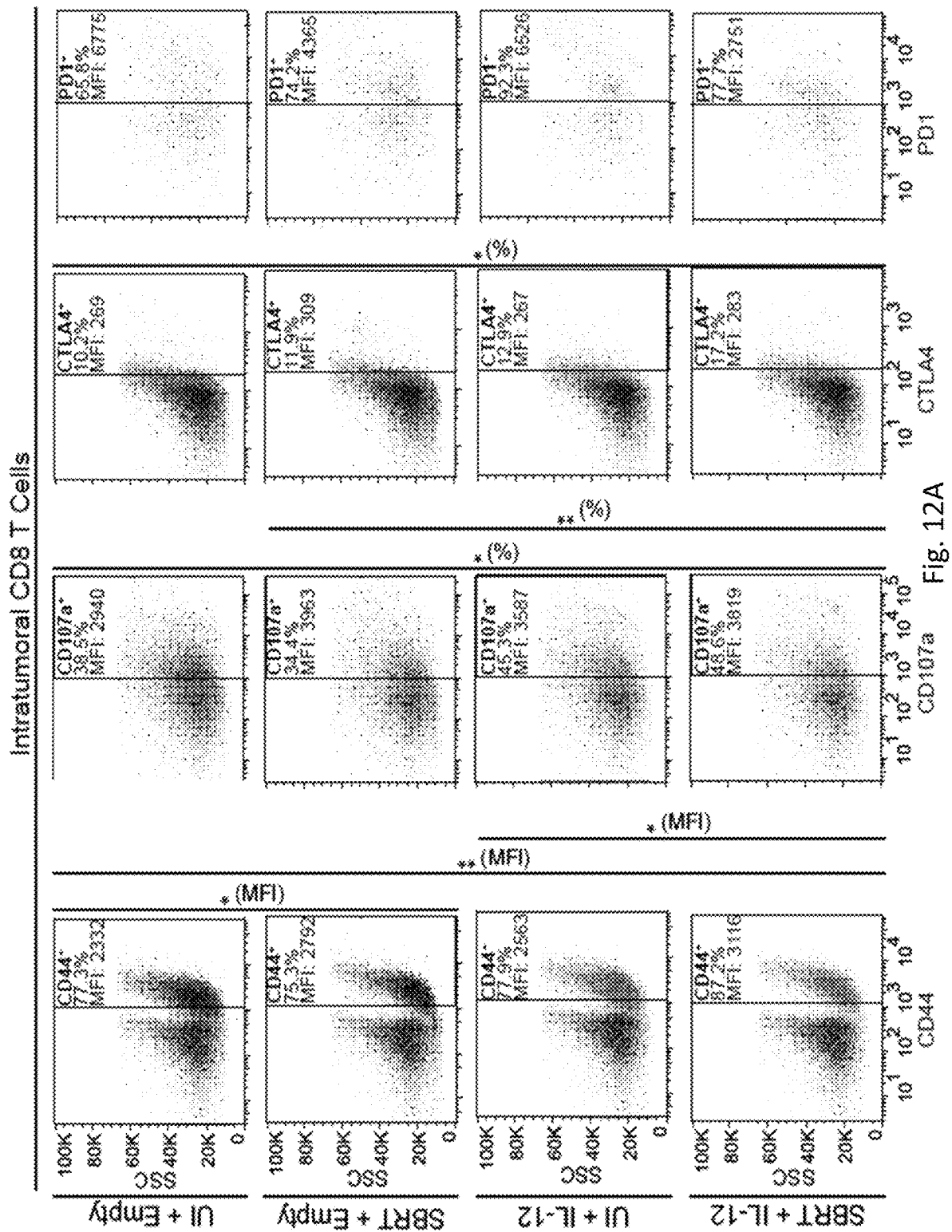
FIG. 12A through FIG. 12C, depicts exemplary experimental data demonstrating expanded intratumoral CD8 T cell activation analyses. SBRT/IL-12 MS-treated KCKO-luc orthotopic tumors (n=4-5) were harvested on day 11 for flow cytometric analysis (n=4-5), Luminex cytokine profiling (n=4-5), or RNA-seq analysis (n=3).
Figure 12B:
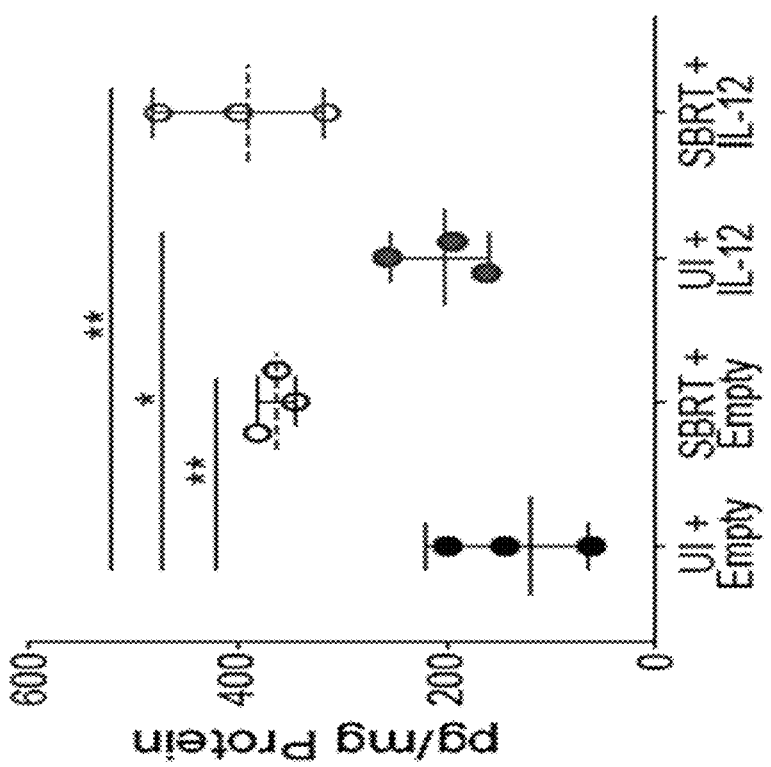

Tumoricidal Effect of SBRT/IL-12 MS Therapy is Dependent Upon Activated CD8 T Cells To determine if CD8 T and/or CD4 $T_h1$ cells were necessary for therapeutic efficacy, CD8- or CD4-depleting antibodies were administered one day prior to SBRT treatment (day 5) of KCKOluc tumors and repeated dosing every three days for two weeks. Strikingly, IVIS bioluminescent imaging demonstrated the complete abrogation of antitumor effects upon CD8$^+$ depletion, whereas CD4$^+$ depletion showed no effect (FIG. 9D). To assess CD8 T cell activation status, flow cytometric and Luminex analyses were performed of day 11 KCKO-luc tumors. Following SBRT/IL-12 MS, an upregulated expression of the CD44 activation marker was observed and a greater percentage of degranulating CD107a+ cells (FIG. 12A, far-left and mid-left panels, respectively). Corroborating increased CD107a degranulation, heightened intratumoral levels of granzyme B (GZMB) were observed in SBRT and SBRT/IL-12 MS groups (FIG. 12B). CD8 T cells did not demonstrate increased levels of the exhaustion markers CTLA4 and PD1 on a per cell basis; however, there was a greater percentage of cells expressing these markers, suggesting a greater overall number of activated, but not exhausted, CD8 T cells (FIG. 12A, mid-right and far-right panels, respectively).

Figure 10:
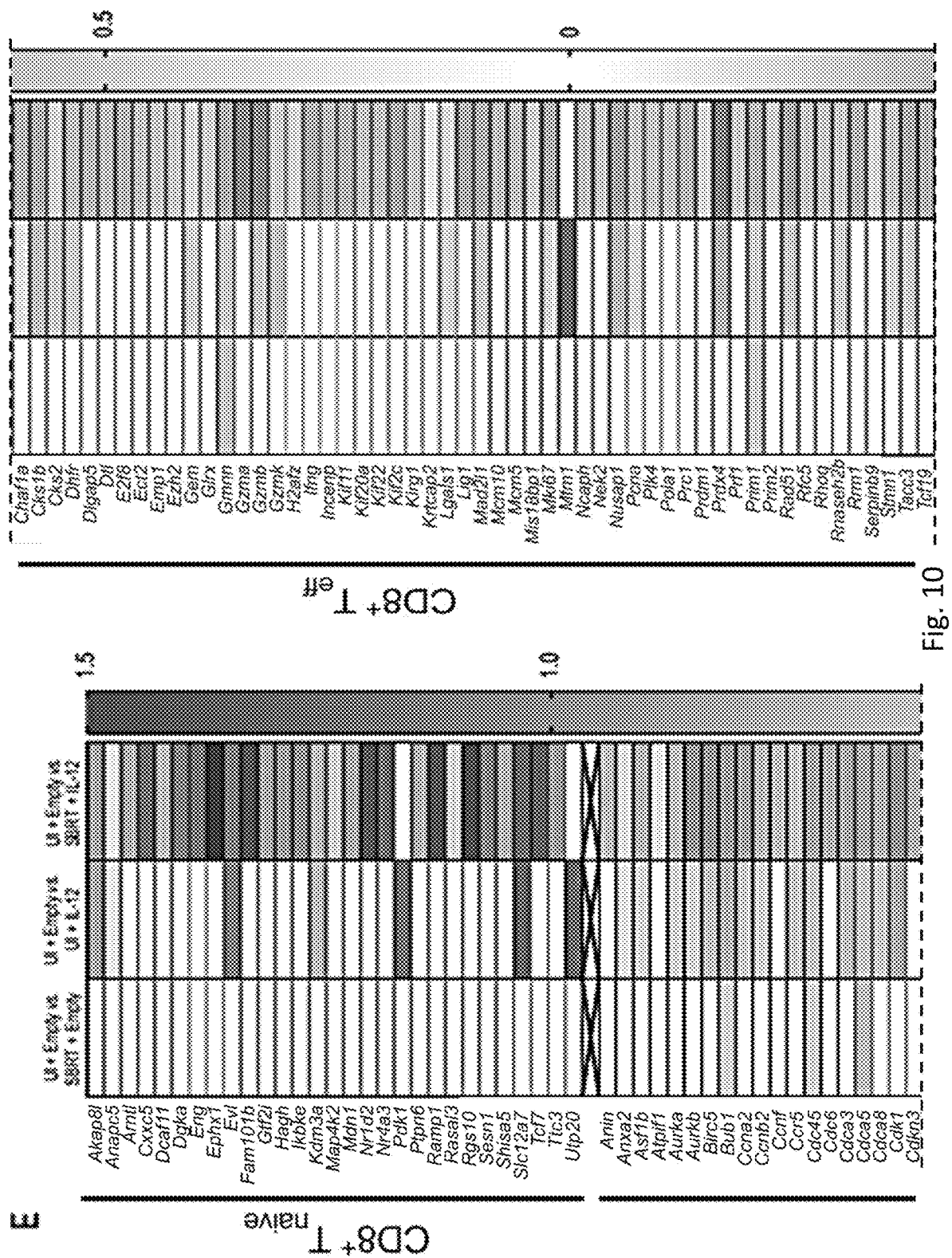
FIG. 10 depicts exemplary experimental data demonstrating the transcriptome profile of CD8$^+$ T cells. CD8$^+$ T cells were flow sorted prior to RNA-seq analysis. SBRT/empty MS, UI/IL-12 MS, and SBRT/IL-12 MS DEGs (versus UI/empty MS controls) were compared to naive ($T_{naive}$), effector ($T_{eff}$), effector-memory ($T_{em}$), and exhausted ($T_{ex}$) T cell genesets from the Broad Institute MSigDB (MSigDB: GSE1000002), and gene matches are presented in heatmaps. Representative of one experiment.
Figure 10:
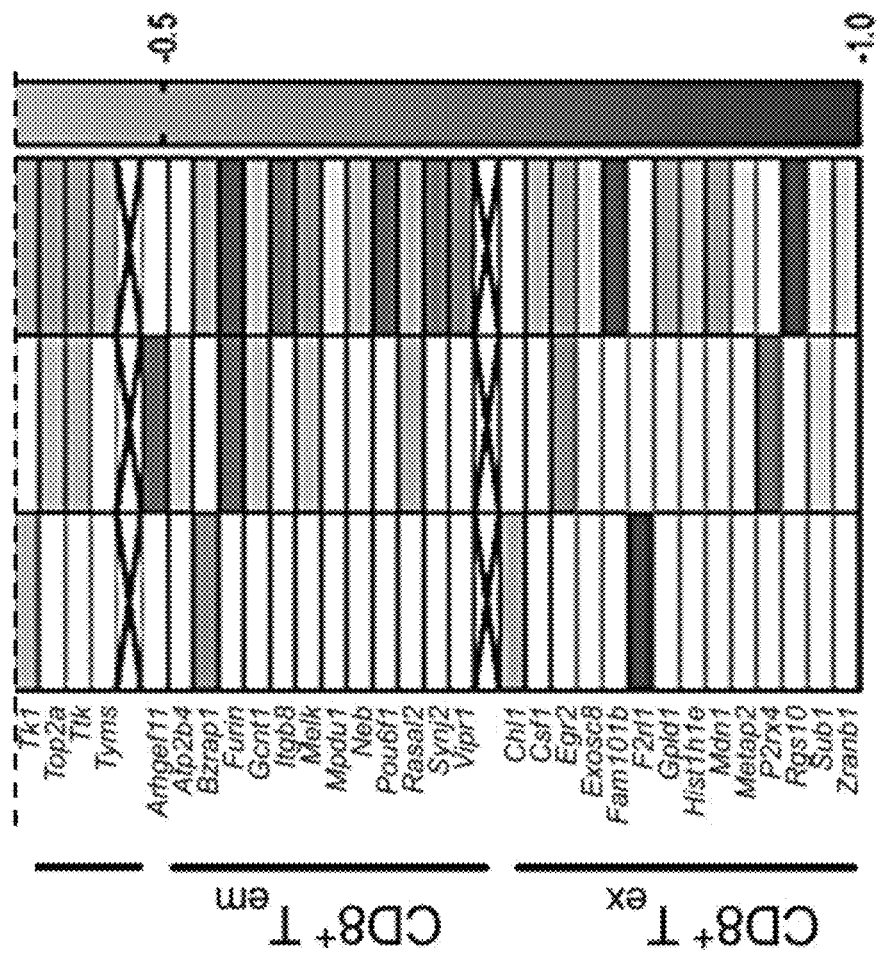
Figure 12C:
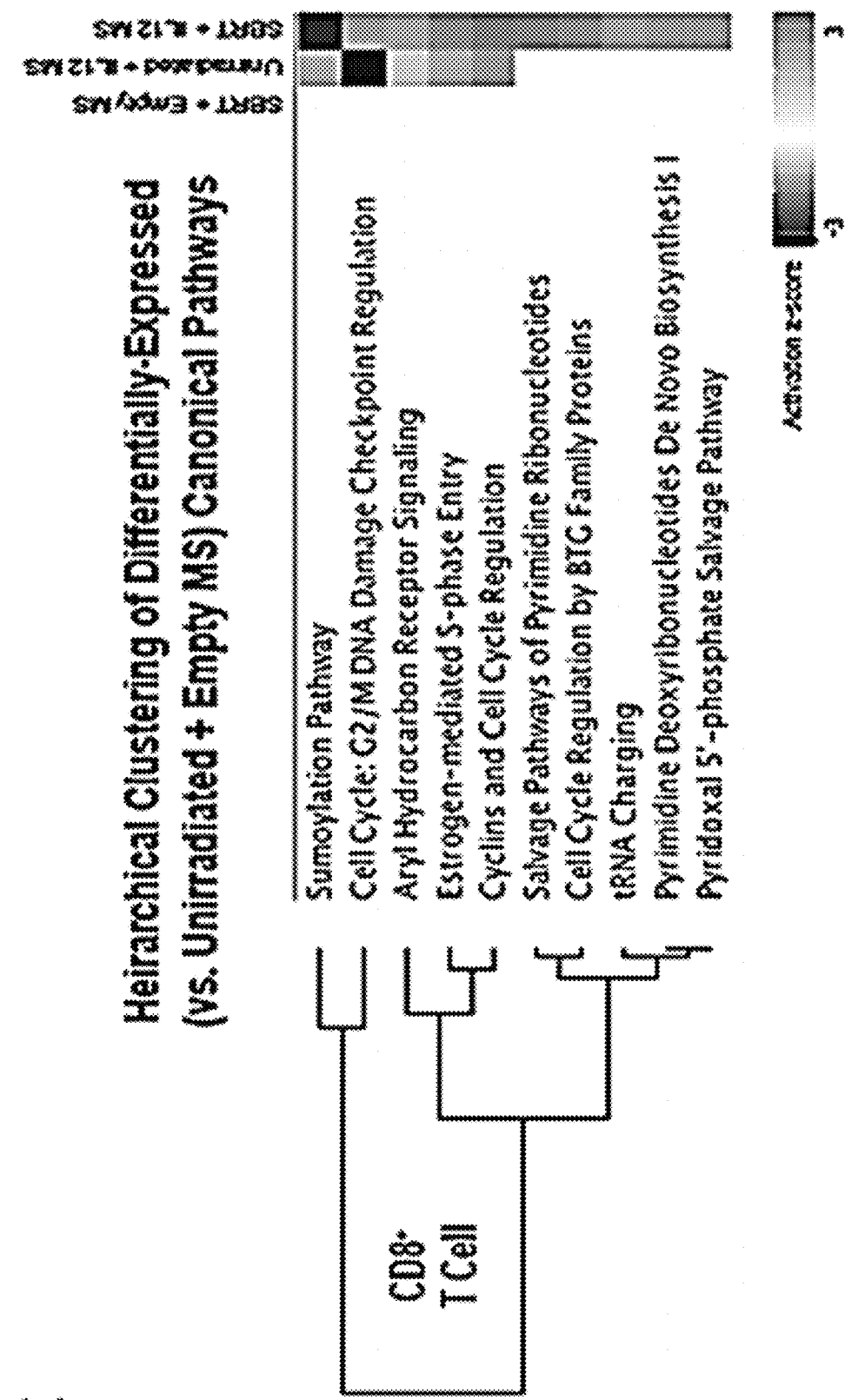

For further assessment of the T cell activation status in the KCKO-luc orthotopic tumor model, RNA-seq analysis was performed on sorted CD8 cells from each of the four experimental groups. Ingenuity pathway analysis of DEGs (versus unirradiated/empty MS; $-1.5<z<1.5$) identified the activation of proliferative functions, including 5-phase entry and cyclin regulation, alongside the deactivation of G2/M checkpoint regulation in IL-12 MS and SBRT/IL-12 MS groups. The SBRT/IL-12 MS group demonstrated the upregulation of protein translation (tRNA charging and pyridoxal 50-phosphate salvage) and nucleotide biosynthesis pathways (pyrimidine salvage and pyrimidine de novo biosynthesis), which are chief to clonal expansion and effector and memory differentiation of CD8+ T cells (FIG. 12C) (Quemeneur et al., 2004, The Journal of Immunology, 173(8):4945-4952). At the individual gene level, differential expressers (|log$_2$[fold-change]|>0.5 versus unirradiated/empty MS; p<0.05) were classified into subsets using the MSigDB (MSigDB: GSE1000002). Upon sorting DEGs into naive ($T_{naive}$), effector ($T_{eff}$), effectormemory ($T_{em}$), and exhausted ($T_{ex}$) T cell groups, an overwhelming downregulation of naive (26 down, 2 up) and upregulation of effector genes (76 up, 1 down) was observed with SBRT/IL-12 MS treatment. Furthermore, 70% of differentially expressed effector-memory genes were upregulated, and only 6 of 13 exhaustion transcripts identified were augmented. SBRT and IL-12 MS monotherapies demonstrated similar patterns in differential expression; however, the quantity of DEGs was greatly reduced compared to SBRT/IL-12 MS (FIG. 10). Interferon g was not identified as a top upstream regulator of differential expression in any treatment group, emphasizing its indirect effects by repolarization of suppressor cells (Table 3). Collectively, these findings demonstrate the augmentation of intratumoral T cell activation and memory formation elicited by SBRT/IL-12 MS combination treatment and illustrate the significance of this process for therapeutic response.

TABLE 3

Top Upstream Regulators of Intratumoral CD8+ T Cell Response to SBRT/IL-12 MS SBRT/IL-12 MS-treated KCKO-luc orthotopic tumors were harvested on day 11 and digested into single cell suspensions. Lysates were flow sorted to isolate CD8+ T cells for RNA-seq analysis. Differentially-expressed genes (versus unirradiated + empty MS controls) were analyzed using Ingenuity Pathway Analysis comparing each of the 3 treatment groups to unirradiated + empty MS controls (n = 3). Top activated and inhibited upstream regulators (pvalues of overlap <10-20) of differentially-expressed pathways are represented. Representative of one experiment.

| Upstream Regulator | Molecule Type | Predicted Activation State | Activation z-score | p-value of overlap |
| --- | --- | --- | --- | --- |
| TP53 | transcription regulator | Inhibited | −3.089 | 6.21E−51 |
| E2F4 | transcription regulator | | −0.391 | 1.22E−48 |
| CDKN1A | kinase | Inhibited | −3.727 | 1.13E−47 |
| E2F1 | transcription regulator | Activated | 4.526 | 8.41E−40 |
| RABL6 | other | Activated | 6.164 | 1.11E−36 |
| TCF3 | transcription regulator | Inhibited | −2.426 | 1.07E−35 |
| TBX2 | transcription regulator | Activated | 5.6 | 3.5E−33 |
| RB1 | transcription regulator | Inhibited | −3.762 | 8.68E−32 |
| ERBB2 | kinase | Activated | 7.342 | 1.49E−31 |
| CSF2 | cytokine | Activated | 7.626 | 2.98E−31 |
| E2F | group | Activated | 4.888 | 2.41E−30 |
| CCND1 | transcription regulator | Activated | 4.282 | 2.42E−30 |
| EP400 | other | Activated | 3.973 | 1.04E−29 |
| PTGER2 | g-protein coupled receptor | Activated | 6.245 | 6.54E−28 |

TABLE 3-continued

Top Upstream Regulators of Intratumoral CD8+ T Cell Response
to SBRT/IL-12 MS SBRT/IL-12 MS-treated KCKO-luc orthotopic
tumors were harvested on day 11 and digested into single cell
suspensions. Lysates were flow sorted to isolate CD8+
T cells for RNA-seq analysis. Differentially-expressed genes
(versus unirradiated + empty MS controls) were analyzed
using Ingenuity Pathway Analysis comparing each of the 3 treatment
groups to unirradiated + empty MS controls (n = 3).
Top activated and inhibited upstream regulators (pvalues of
overlap <10-20) of differentially-expressed pathways are
represented. Representative of one experiment.

| Upstream Regulator | Molecule Type | Predicted Activation State | Activation z-score | p-value of overlap |
|---|---|---|---|---|
| TCF4 | transcription regulator | | | 2.19E-26 |
| let-7 | microrna | Inhibited | -6.041 | 8.95E-26 |
| MITF | transcription regulator | Activated | 5.691 | 2.85E-25 |
| CDKN2A | transcription regulator | Inhibited | -5.46 | 1.41E-24 |
| FOXO3 | transcription regulator | | -1.623 | 1.79E-24 |
| HGF | growth factor | Activated | 5.525 | 4.92E-24 |
| E2F3 | transcription regulator | Activated | 4.969 | 3.69E-23 |
| RRP1B | transcription regulator | | | 2.14E-22 |
| RB | group | Inhibited | -4.468 | 7.29E-22 |
| FOXM1 | transcription regulator | Activated | 4.971 | 1.65E-21 |
| E2F2 | transcription regulator | Activated | 2.433 | 4.78E-21 |
| YY1 | transcription regulator | | -1.048 | 2E-20 |
| CDK4 | kinase | | | 2.54E-20 |
| VEGF | group | Activated | 5.628 | 4.61E-20 |

Figures 13A, 13B, 13C, 13D:
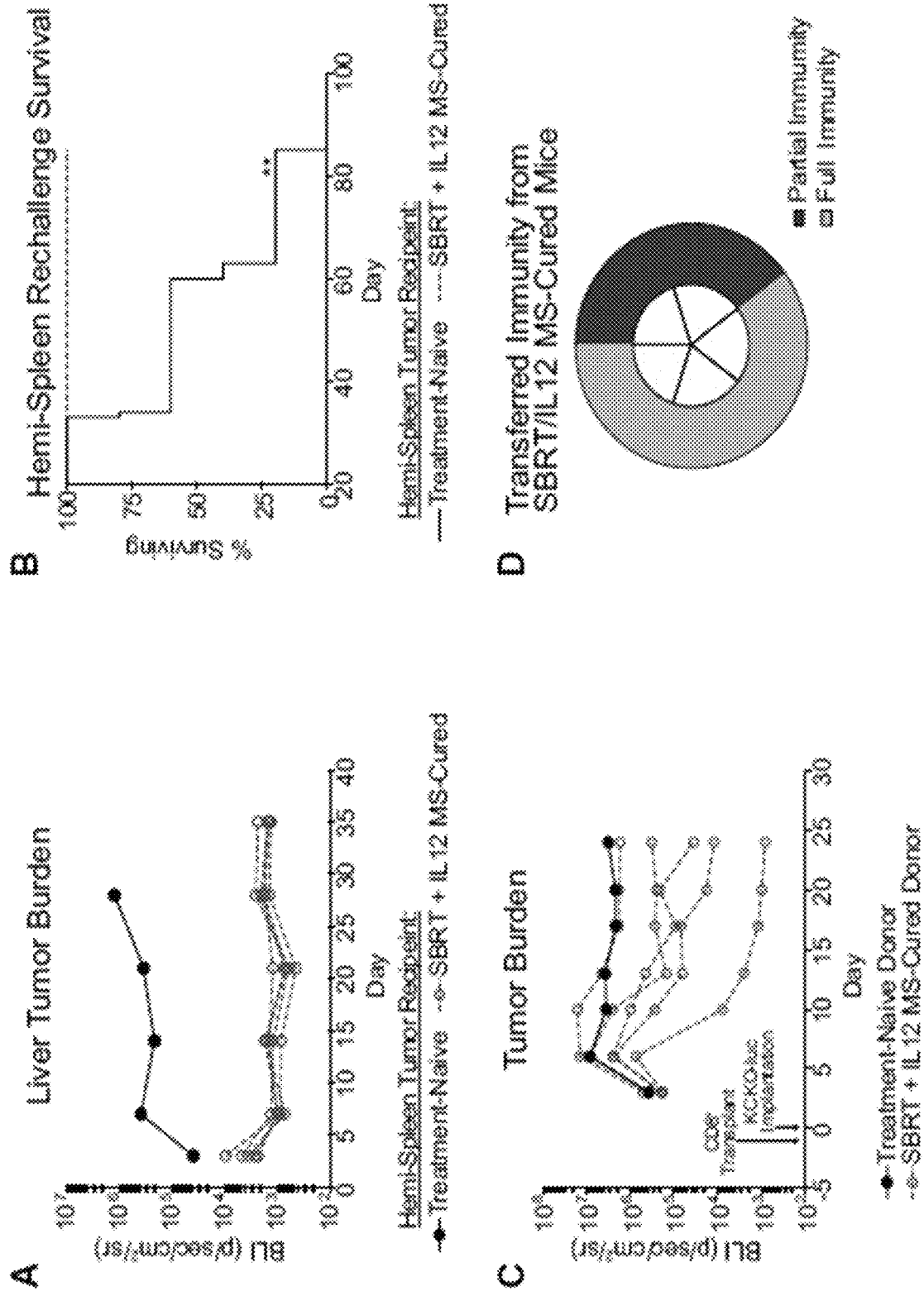

SBRT/IL12 MS Therapy Provides Systemic Anti-Tumor Immunity that Drives an Abscopal Effect SBRT/IL-12 MS treatment of KCKO-luc tumors lead to long-term survival in 100% of mice. Accordingly, without being bound by theory, it was hypothesized that immunological memory had been established. To test for longterm immunity, SBRT/IL-12 MS-cured mice were rechallenged with metachronous KCKO-luc tumors approximately 6 months after the treatment of primary tumors. The hemi-spleen tumor model recapitulates metastatic tumor formation in the liver, the most common site of PDA dissemination. Tumor cells were injected into the spleen where they passively diffused to the liver by the hepatic portal vein. Hemi-splenectomy was performed post-implantation to prevent non-specific tumor formation. Three days following rechallenge, decreased KCKO-luc seeding was observed in SBRT/IL-12 MS-cured mice relative to age-matched naive controls, as measured by tumor bioluminescence. By day 7 post-implantations, SBRT/IL-12 MS-cured mice demonstrated no evidence of liver tumor burden, which was corroborated by a significant survival benefit (FIGS. 13A and 13B). For additional confirmation of long-term antitumor immunity, CD8 T cells were transferred from rechallenged mice into naive mice, hypothesizing that cells from SBRT/IL-12 MS-cured donor mice would protect naive recipients during tumor challenge. Nine months following primary tumor eradication, CD8 T cells were purified from the remaining spleen and lymph nodes of SBRT/IL-12 MS-treated mice. Donor mice were not primed in any way prior to T cell isolation, and naive donor controls were age-matched. T cells were intravenously injected into recipient mice 16 hours prior to orthotopic KCKO-luc implantation. As early as day 5 post-implantations, reduced tumor seeding was observed in recipient mice infused with CD8 T cells from SBRT/IL-12 MS-cured donors, and by day 24, antitumor responses were evident in all 5 mice, as demonstrated by IVIS bioluminescent analysis (FIG. 13C). Subsequent analyses at day 40 revealed no evidence of tumor (by palpation) in 60% of mice infused with CD8 T cells from the SBRT/IL-12 MS-cured group, indicating the transferal of full antitumor immunity to naive recipients (FIG. 13D). Comprehensively, these results demonstrate the formation of a targeted immune response against KCKO-luc tumors upon SBRT/IL-12 MS treatment that generates tumor-specific memory CD8 T cells.

Figure 14A:
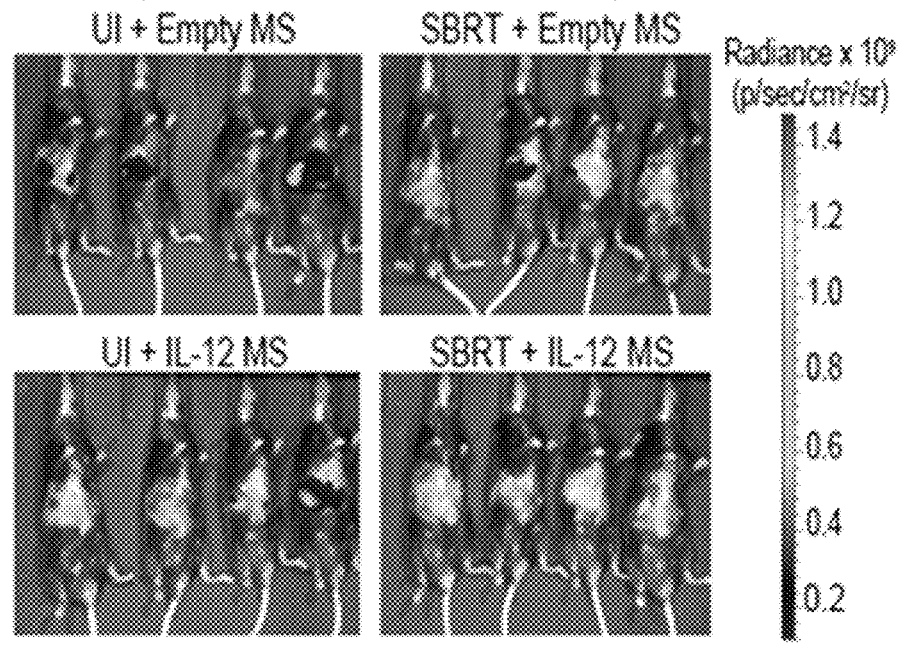
FIG. 14A through FIG. 14F, depicts exemplary experimental data demonstrating an expanded analysis of abscopal effect. (A and B) KCKO-luc cells were implanted on day 0 (n=3) into the liver using the hemi-spleen model, while KCKO cells were simultaneously injected into the pancreas. The SBRT/IL-12 MS treatment paradigm was followed for the treatment of pancreas tumors only. KCKO-luc liver tumor bioluminescence was tracked over time IVIS imaging.
Figure 14B:
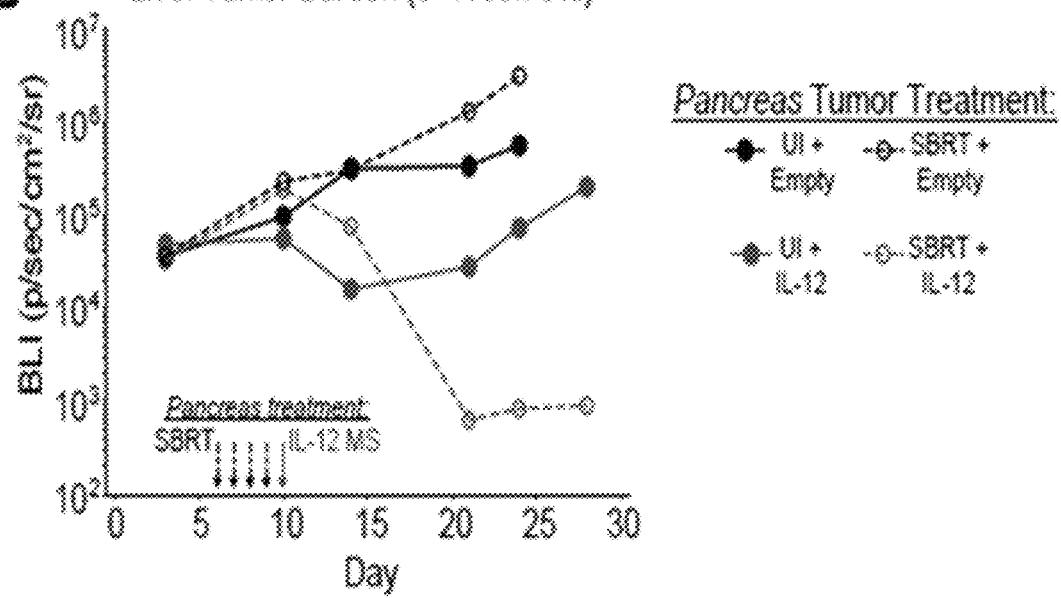
Figure 14C:
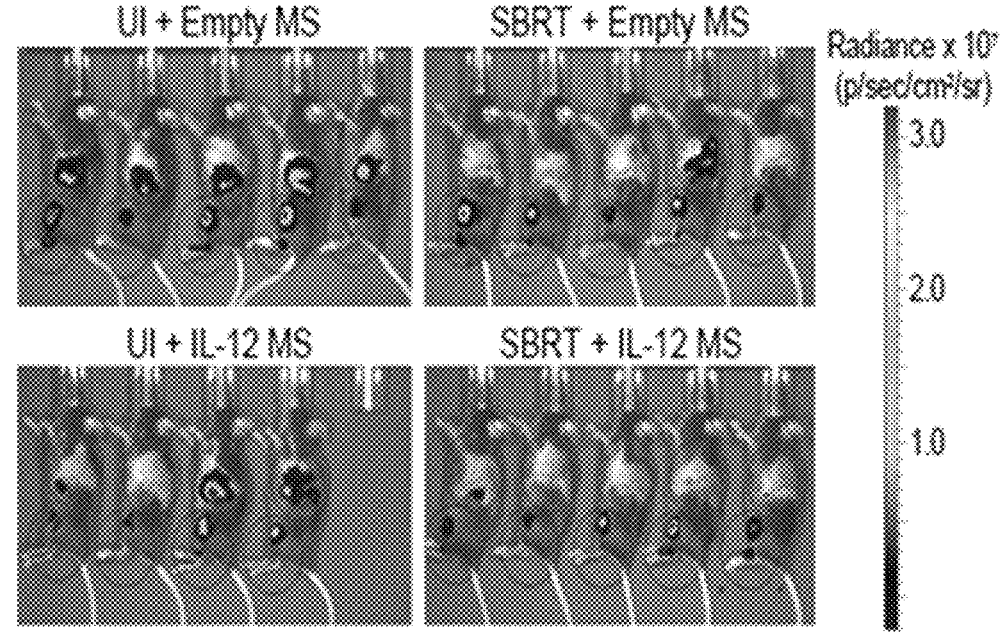
Figure 14D:
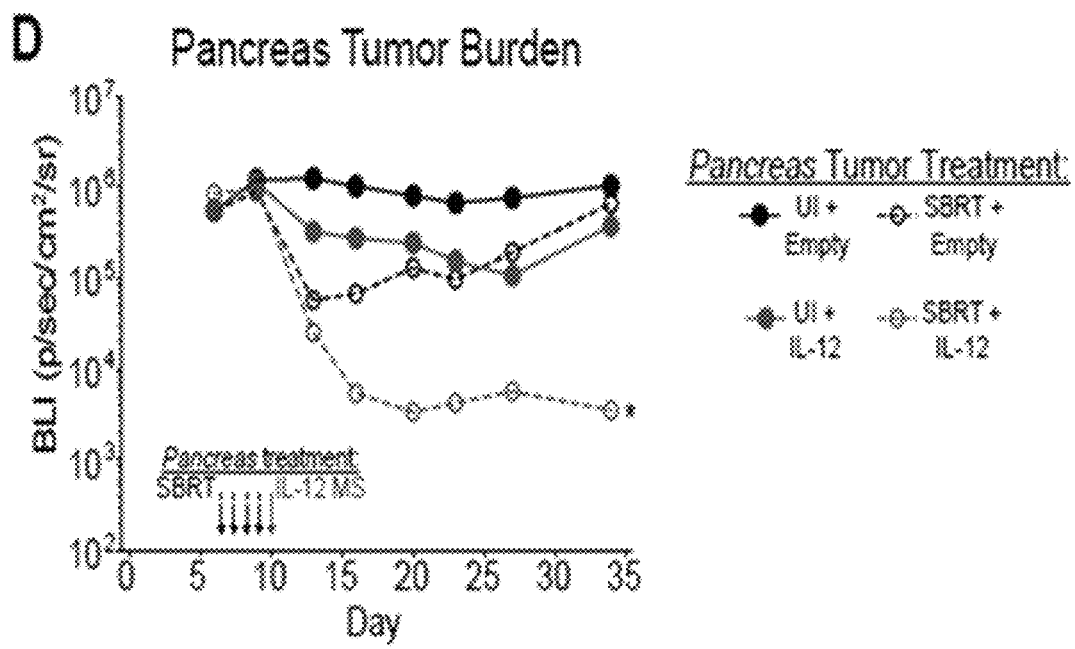
Figure 14E:
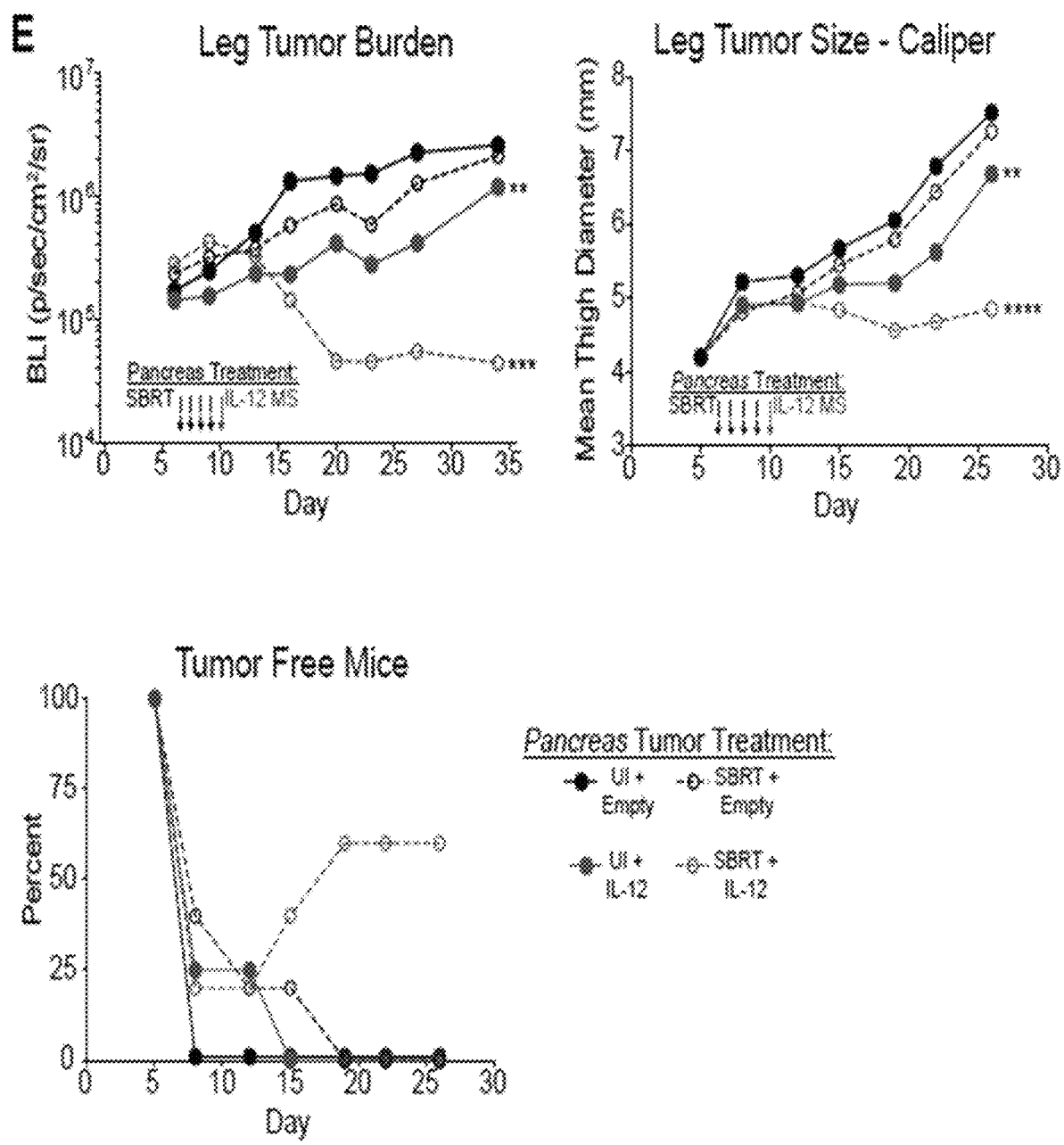
Figure 14F:
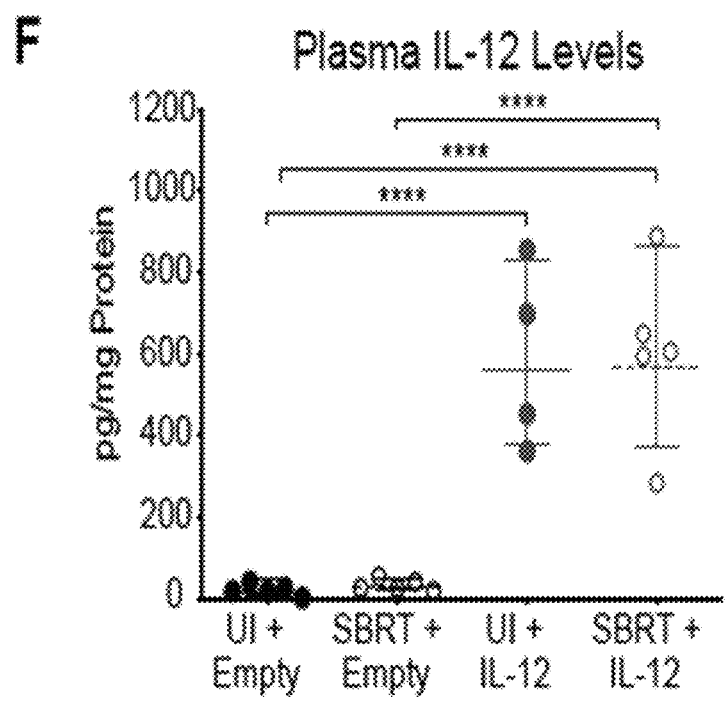

Greater than 50% of locally advanced pancreatic malignancies present with metastatic disease that precludes patients from surgery (Hidalgo et al., 2015, Pancreatology, 15(1):8-18). It has been postulated that the abscopal effect induced by RT is driven by the activation of a systemic immune response, characteristic of an in situ tumor vaccination (de la Cruz Merino et al., 2014, Front Immunol, 5:102). Unfortunately, the abscopal effect following RT monotherapy is rarely observed clinically, suggesting the need for optimization by targeting the immune system (e.g., IL-12 MS). Having shown that SBRT/IL-12 MS elicited potent local effects on orthotopic pancreas tumors, next it was tested whether combination therapy could elicit an abscopal effect on a synchronous secondary tumor. Primary KCKO (luciferase null) tumors were injected in the pancreas alongside simultaneous implantation of secondary KCKO-luc metastases in the liver by using the hemi-spleen technique (FIG. 13E). SBRT and IL-12 MS therapeutic scheduling was not modified, and treatments were delivered only to the primary pancreas tumor. IVIS bioluminescent imaging was used to track luciferase-expressing liver metastases, and although untreated and monotherapy-treated controls developed aggressive metastatic disease (FIGS. 14A and 13F), SBRT/IL-12 MS treatment resulted in the elimination of established liver metastases (FIG. 13F) and significantly improved survival (FIG. 13G). These experiments also demonstrated the therapeutic potency of SBRT/IL-12 MS in aged mice (30 weeks old); however, similar results were observed when the experiment was repeated in 6- to 8-week-old mice (FIG. 14B). Additionally, the abscopal effect elicited by SBRT/IL-12 MS was not limited to the liver. A distant metastasis model was also used in which KCKO-luc tumor cells were synchronously implanted in the pancreas (primary lesion) and leg muscle (secondary lesion) and both were measured using IVIS imaging (FIG. 14C). Although no difference in the therapeutic response of primary tumors was observed, both bioluminescent and caliper measurements confirmed a significant size reduction of untreated leg tumors upon SBRT/IL-12 MS treatment of the pancreas, resulting in 60% of mice being tumorfree at 25 days post-implantation (FIGS. 14D and 14E, respectively). By monitoring plasma IL-12 concentrations, it could be determined if systemic increases were generating the observed abscopal effect. Plasma IL-12 levels were found to be uniformly upregulated in both IL-12 MS and SBRT/IL-12 MS groups following treatment (FIG. 14F); however, the abscopal effect was only observed in the SBRT/IL-12 MS treatment group. These data suggest that although systemic increases in IL-12 may contribute to the therapeutic effect on secondary lesions, only the combination of SBRT with IL-12 MS generates a systemic antitumor effect that is capable of destroying established metastases.

The development of conRT for PDA has lost initiative in recent years after clinical trials demonstrated ineffectual overall survival and local tumor control outcomes (Neoptolemos et al., 2004, N. Engl. J. Med. 350:1200-1210.; Rich et al., 2004, Am. J. Clin. Oncol. 27:51-56; Hammel et al., 2016, JAMA 315:1844-1853.) Studies over the last decade have characterized the importance of an intact immune response for tumor resolution following radiotherapy, and immune attenuation could be a chief contributor to these clinical shortcomings. This work examined two emerging therapeutic strategies for PDA, SBRT and immunotherapy, hypothesizing that the combination would stimulate an immunogenic response capable of downsizing locally advanced lesions. The PDA tumor microenvironment (TME) is highlighted by a profoundly immunosuppressive stroma that accompanies PDA transformation and prevents the establishment of CD8 T effector responses (Feig et al., 2012, Clin. Cancer Res. 18:4266-4276.) Furthermore, commonly utilized conRT scheduling can also impart lymphopenia in addition to promoting an immunosuppressive cellular milieu (Schrek, 1961, Ann. N Y Acad. Sci. 95:839-848; Rech et al., 2018, Cancer Res. 78:282-4291; Xu et al., 2013, Cancer Res. 73:2782-2794.) The immunohistochemistry (IHC) findings (FIG. 1) highlighted the core benefit of SBRT, namely, increased intratumoral CD8 T cell load, and accordingly, SBRT scheduling was approached as a means of delivering acute tumor damage to amplify the antigen-specific adaptive immune response. Conversely, abundant myeloid suppressor cell densities were observed in both untreated and SBRT-treated patient samples, suggesting that the presence of immunosuppressor cells remained a central therapeutic obstacle. These results prompted the development of an immunotherapy combination (IL-12 MS) that could both stimulate the activation of recruited CD8 T cells, as well as reprogram the abundance of immunosuppressor cells throughout the tumor.

Figures 15A, 15B, 15C, 15D:
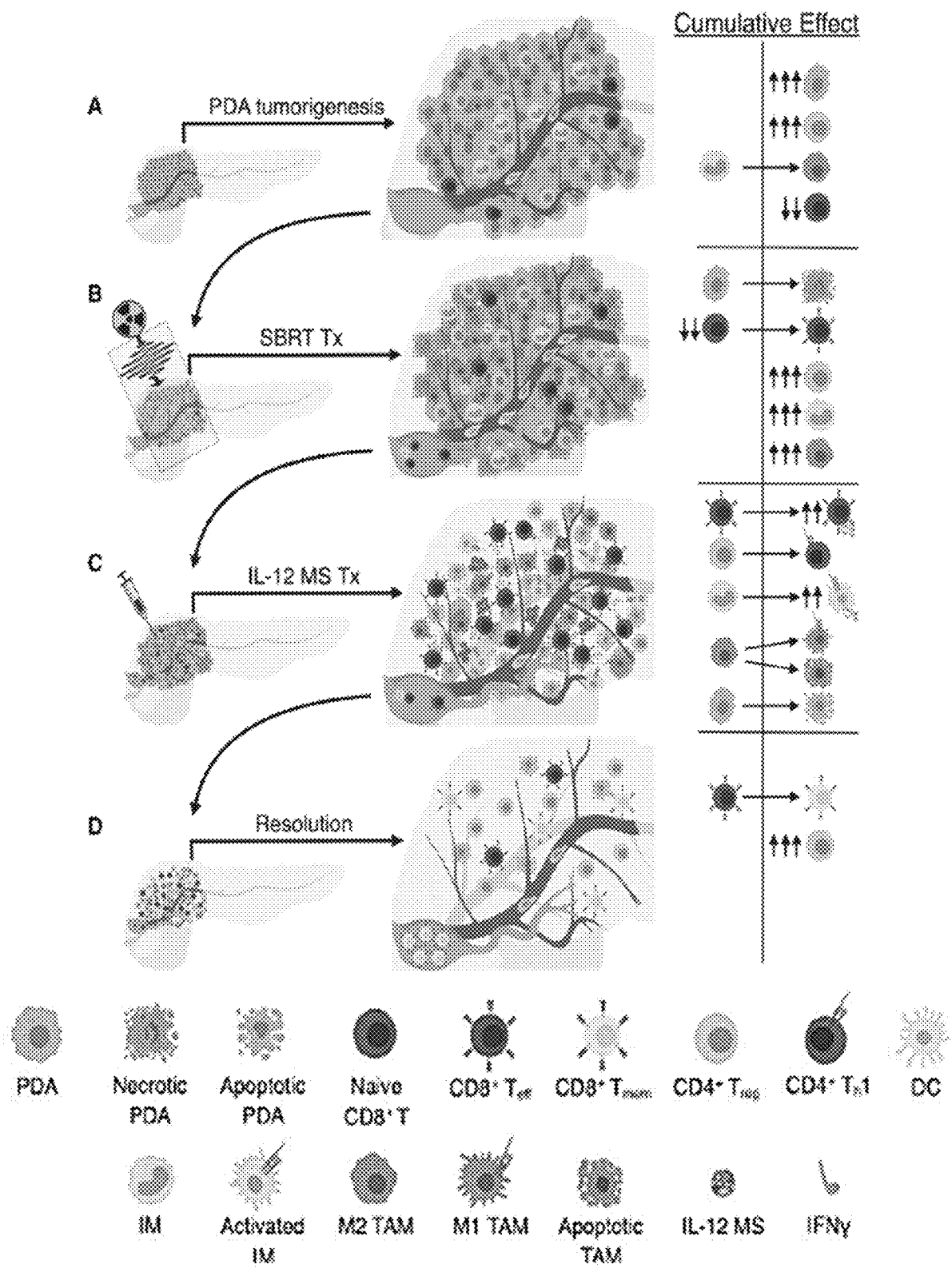
FIG. 15A through FIG. 15D, depicts schematics of SBRT/IL-12 MS therapeutic mechanism in PDA.

PDA is underscored by a diverse protumor landscape that includes a predominance of $T_{reg}$ and myeloid suppressor cells, the exclusion or exhaustion of cytotoxic T cells, and a desmoplastic and/or avascular extracellular matrix. Each of these characteristics contribute to an immune imbalance favoring the immunosuppression inherent to PDA (Feig et al., 2012, Clin. Cancer Res. 18:4266-4276). The development of an antitumor immune response in this setting requires a multifaceted intervention that comprehensively repolarizes the stromal component. For this reason, the pleiotropic activity of IL-12 made it an attractive candidate for intervention. This work demonstrates a robust antitumor effect in recalcitrant PDA tumors by using SBRT/IL-12 MS treatment. Furthermore, therapeutic efficacy was demonstrated across three aggressive preclinical models, with the KCKO-luc orthotopic model resulting in 100% cures (FIG. 2). The ability of SBRT/IL-12 MS therapy to reprogram and commandeer the diverse immunosuppressive stroma in PDA may explain why there were powerful immune responses across characteristically cold tumor models. The synergistic IFNγ induction following SBRT/IL-12 MS combination is striking, and leads to speculation that SBRT-driven increases in IFNγ-producing cells is a crucial precursor event. Although NK cells and APCs are common contributors to IFNγ production, their relative abundances were found to be unaffected by SBRT treatment alone (FIGS. 11A and 11C). Rather, a SBRT/IL-12 MS-treated CD8 T cell transcriptome was observed that was primed for IFNγ production (FIG. 10). Surprisingly, coordinate studies investigating intratumoral IFNγ levels under CD8+ T cell depletion demonstrated increased cytokine amounts with SBRT/IL-12 MS treatment, underscoring both CD4 T cell and myeloid contributions and compensatory potential. Although robust IFNγ induction was observed, the expression was transient (similar to the profile of IL-12 release; FIG. 5), and the mechanism by which acute IFNγ priming can initiate a sustained antitumor response is not completely understood. One contributing factor may be the coordination of IFNγ and tumor necrosis factor α (TNFα) stimulation. Synchronous high-level IFNγ/TNFα signaling can initiate an autocrine loop of proinflammatory signaling, leading to the stable reprogramming of myeloid suppressors. IFNγ has been shown to elicit transcriptional feedback on IL-12 through IFN consensus sequence binding protein (ICSBP) activation, driving a feedforward response. Although this signaling architecture can produce powerful proinflammatory events, persistent interferon stimulation has been shown to drive epigenetic changes that promote multiple T cell exhaustion paradigms (Benci et al., 2016, Cell 167:1540-1554.e12.). The intratumoral Luminex profiling (FIG. 5) suggests that feedforward IL-12/IFNγ production occurs following SBRT/IL-12 MS treatment in the KCKO-luc model (FIG. 11A). Importantly, during peak IL-12/IFNγ signaling (day 11), marked CD8 T cell exhaustion was not observed, and heightened cell numbers at day 14 suggest sustained proliferation for multiple days following IL-12 MS delivery (FIGS. 9B and 10). In addition to IM/TAM repolarization events, the CD8 T cell response was likely supported by acute reductions in $T_{reg}$ density mediated by IFNγ; however, $T_{reg}$ restoration approximately 96-hours post-treatment may be of similar therapeutic importance (FIG. 11E). IFNγ-dependent indoleamine 2,3-dioxygenase (IDO) induction has been found to enhance $T_{reg}$ rebound following cytotoxic events, and work by Kalia et al. (2015, Immunity 42:1116-1129) would suggest that $T_{reg}$ signaling through CTLA4 is necessary for the formation of fit and functional $T_{mem}$ populations. The ability of SBRT/IL-12 MS to evoke a dynamic proinflammatory stimulus followed by standard immunomodulatory feedback and memory formation may be essential for therapeutic efficacy. Maintaining an invigorated repertoire of tumor-specific T cells following the SBRT/IL-12 MS response dramatically improves the potential for successful second-round treatment with a tertiary immunotherapy or repeated IL-12 MS administration. This work has uncovered a multifaceted mechanism, illustrated in FIG. 15, through which SBRT/IL-12 MS elicits antitumor effects. PDA tumorigenesis is typically highlighted by marked infiltration of immunosuppressive Treg cells, IMs that seed TAM populations, and a paucity of CD8 T cells in the lesion periphery (FIG. 15A). An antitumor immune response is initiated by SBRT, which likely induces immunogenic tumor cell death producing tumor antigen and presentation, both of which are necessary for $T_{eff}$ formation in the draining lymph node (DLN) (green) (FIG. 15B). However, these increases in intratumoral CD8 $T_{eff}$ cells have modest antitumor effects due to the ancillary recruitment of Treg and IM/TAM suppressors. To overcome this obstacle, local IL-12 MS treatment stimulates intratumoral T effectors to produce IFNγ, which repolarizes both lymphoid and myeloid suppressors (FIG. 15C). The resolution of PDA tumors is highlighted by Treg rebound and $T_{mem}$ formation, resulting in lasting tumor-specific immune memory that can control and/or eliminate distal metastases (FIG. 15D). This proposed summary likely represents the oversimplification of a much more complex antitumor mechanism involving a multitude of cells and pathways not yet defined. For example, the IL-12/IFNγ axis is capable of eliciting effects on non-immune targets, such as tumor cells (increased MHCI expression and cytostatic and/or cytotoxic effects) and endothelial cells (release of antiangiogenic and immune adhesion molecules), that may also contribute to immune-mediated antitumor effects (Suzuki et al., 1998, Tohoku J. Exp. Med. 185:223-226; Strasly et al., 2001, J. Immunol. 166:3890-3899). Intratumoral IL-12 administration was used to mitigate the systemic toxicity of intravenous administration observed in some clinical studies (Jenks, 1996, J. Natl. Cancer Inst. 88:576-577.) Importantly, no mice experienced adverse events or exhibited signs of immune reaction to IL-12 MS treatment, and a phase I clinical trial of SBRT/IL-12 MS in locally advanced PDA is in preparation. Serial surgeries were used to deliver IL-12 in PDA mouse models (FIG. 2); however, translating this approach to the clinic would likely involve endoscopic ultrasound-guided (EUS) techniques. EUS intervention is currently used for PDA diagnosis and staging as well as fiducial marker placement for radiotherapy and would be a safe, minimally invasive approach for i.t. IL-12 MS delivery (Al-Haddad and Eloubeidi, 2010, JOP 11:1-7). It was postulated that MS packaging provides an added level of IL-12 intratumoral sequestration due to the enhanced permeability and retention (EPR) effect. The encapsulation of IL-12 in a 1- to 5-mm polymer coating likely prevents passive clearance by weakened lymphatic drainage while protecting the cytokine from proteolytic degradation or phosphatidylserine capture in the TME (Sevenich and Joyce, 2014, Genes Dev. 28:2331-2347; Oyler-Yaniv et al., 2017, Mol. Cell 66, 635-647.e7). Apart from supporting its sustenance in the TME, MS technology may also affect the cellular uptake and trafficking of IL-12, as work by Champion et al. (2008, Pharm. Res. 25:1815-1821) demonstrated, the phagocytosis and internalization of 2- to 3-mm polystyrene MSs by rat alveolar macrophages. Similar engulfment was not observed following i.p. injection of AF594-labeled MS (FIGS. 3C and 3D). These findings evoke compelling questions surrounding intracellular IL-12 signaling mechanisms, the role of phagocytosis in myeloid reprogramming, and the active cellular transport of IL-12 MS to sites of PDA dissemination, such as the liver- and tumor-draining lymph nodes. Approximately 60% of locally advanced PDA malignancies present with metastatic disease, and furthermore, this value excludes additional cases with undetectable micrometastases (Gillen et al., 2010, PLoS Med, 7(4):e1000267). A therapy that harnesses the capacity for both local and distal tumor control would dramatically increase the number of patients eligible for neoadjuvant intervention and, potentially, surgical candidacy. Similar to other works investigating SBRT and immunotherapy combination (Yasmin-Karim et al., 2018, Front. Immunol. 9:2030), the evaluation of systemic immune memory following SBRT/IL-12 MS therapy (FIG. 13) confirmed its capacity for abscopal control of an untreated synchronous lesion, suppression of outgrowth upon metachronous rechallenge, and transferal of protection to naive recipients. Comprehensively, these findings strongly suggest that SBRT/IL-12 MS treatment initiated a potent in situ vaccination. From this perspective, rather than classifying IL-12 MS as an adjuvant to radiation, SBRT may also be viewed as a tool for producing tumor a neoantigen that primes the IL-12 MS-driven immune response. The capacity of this combination therapy to potentiate a robust systemic immune response expands interventional opportunity beyond the scope of borderline resectable lesions to include advanced metastatic disease. Alongside the potency and durability of SBRT/IL-12 MS in preclinical models of advanced disease, these features strongly advocate the continued clinical translation of this therapeutic approach for PDA.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating an unresectable pancreatic cancer tumor in a subject having pancreatic cancer, comprising:
    a) administering to said unresectable pancreatic cancer tumor a therapeutically effective amount of ionizing radiation, wherein said ionizing radiation is administered as a targeted radiation therapy, wherein said targeted radiation therapy is selected from the group consisting of hypofractionated tumor directed radiotherapy and stereotactic body radiation therapy (SBRT); and
    b) administering to said subject having pancreatic cancer a therapeutically effective amount of a composition comprising an immunomodulatory cytokine, wherein said immunomodulatory cytokine comprises IL-12, wherein said composition is administered subsequent to said ionizing radiation.

2. The method of claim 1, wherein said ionizing radiation comprises X-rays, gamma rays, electrons or high linear energy transfer (LET) radiation.

3. The method of claim 1, wherein said composition comprises a microparticle or nanoparticle.

4. The method of claim 3, wherein the microparticle or nanoparticle comprises a semi-crystalline matrix.

5. The method of claim 4, wherein the immunomodulatory cytokine is entrapped in the semi-crystalline matrix.

6. The method of claim 1, wherein the targeted radiation therapy is administered by way of a regimen selected from the group consisting of: 3-8Gy/fraction given in 3-8 fractions.

7. The method of claim 1, wherein said composition is administered by intra-tumoral injection.

8. The method of claim 1, comprising administering a single dosage comprising 0.5 μg to 1000 mg of said composition.

9. The method of claim 1, comprising administering multiple dosages of said composition, wherein each dosage comprises 0.5 μg to 1000 mg of said composition.

10. The method of claim 1, wherein the unresectable pancreatic cancer tumor is a locally advanced pancreatic cancer tumor (LAPC) or a metastatic advanced pancreatic cancer tumor.

11. The method of claim 1, wherein said subject is a mammal.

12. The method of claim 11, wherein said subject is a human.

* * * * *